US010017827B2

(12) United States Patent
Sala et al.

(10) Patent No.: US 10,017,827 B2
(45) Date of Patent: Jul. 10, 2018

(54) HERBICIDE-RESISTANT SUNFLOWER PLANTS WITH MULTIPLE HERBICIDE RESISTANT ALLELES OF AHASL1 AND METHODS OF USE

(71) Applicants: BASF AGROCHEMICAL PRODUCTS B.V., Arnhem (NL); NIDERA S.A., Buenos Aires (AR)

(72) Inventors: Carlos Sala, Santa Fe (AR); Mariano Bulos, Santa Fe (AR); Sherry R. Whitt, Raleigh, NC (US); Brigitte J. Weston, Wake Forest, NC (US); Bijay K. Singh, Cary, NC (US); Adriana M. Echarte, Santa Fe (AR)

(73) Assignees: Nidera S.A., Buenos Aires (AR); BASF Agrochemical Products B.V., Arnhem (NL)

( * ) Notice: Subject to any disclaimer, the term of this patent is extended or adjusted under 35 U.S.C. 154(b) by 0 days.

(21) Appl. No.: 14/087,041

(22) Filed: Nov. 22, 2013

(65) Prior Publication Data

US 2015/0147754 A1    May 28, 2015

Related U.S. Application Data

(63) Continuation of application No. 12/594,289, filed as application No. PCT/US2008/059125 on Apr. 2, 2008.

(60) Provisional application No. 60/910,041, filed on Apr. 4, 2007, provisional application No. 61/029,737, filed on Feb. 19, 2008.

(51) Int. Cl.
    *C12Q 1/6895*    (2018.01)
(52) U.S. Cl.
    CPC ..... *C12Q 1/6895* (2013.01); *C12Q 2600/156* (2013.01); *C12Q 2600/172* (2013.01)
(58) Field of Classification Search
    None
    See application file for complete search history.

(56) References Cited

U.S. PATENT DOCUMENTS

| | | |
|---|---|---|
| 4,443,971 A | 4/1984 | Chaleff |
| 4,761,373 A | 8/1988 | Anderson et al. |
| 4,774,381 A | 9/1988 | Chaleff et al. |
| 5,013,659 A | 5/1991 | Bedbrook et al. |
| 5,084,082 A | 1/1992 | Sebastian |
| 5,116,402 A | 5/1992 | Dutka et al. |
| 5,141,870 A | 8/1992 | Bedbrook et al. |
| 5,198,599 A | 3/1993 | Thill |
| 5,304,732 A | 4/1994 | Anderson et al. |
| 5,331,107 A | 7/1994 | Anderson et al. |
| 5,378,824 A | 1/1995 | Bedbrook et al. |
| 5,478,789 A | 12/1995 | Hattori et al. |
| 5,478,798 A | 12/1995 | Mayer et al. |
| 5,488,029 A | 1/1996 | Hamprecht et al. |
| 5,539,092 A | 7/1996 | Haselkorn et al. |
| 5,545,822 A | 8/1996 | Croughan |
| 5,595,890 A | 1/1997 | Newton et al. |
| 5,597,717 A | 1/1997 | Guerireau et al. |
| 5,605,011 A | 2/1997 | Bedbrook et al. |
| 5,633,437 A | 5/1997 | Bernasconi et al. |
| 5,633,444 A | 5/1997 | Guerineau et al. |
| 5,643,779 A | 7/1997 | Ehrlich et al. |
| RE35,661 E | 11/1997 | Thill |
| 5,718,079 A | 2/1998 | Anderson et al. |
| 5,719,046 A | 2/1998 | Guerieneau et al. |
| 5,731,180 A | 3/1998 | Dietrich |
| 5,736,629 A | 4/1998 | Croughan |
| 5,767,361 A | 6/1998 | Dietrich |
| 5,767,366 A | 6/1998 | Sathasivan et al. |
| 5,773,702 A | 6/1998 | Penner et al. |
| 5,773,703 A | 6/1998 | Croughan |
| 5,773,704 A | 6/1998 | Croughan |
| 5,821,126 A | 10/1998 | Durzan |
| 5,853,973 A | 12/1998 | Kakefuda et al. |
| 5,858,652 A | 1/1999 | Laffler et al. |
| 5,859,348 A | 1/1999 | Penner et al. |

(Continued)

FOREIGN PATENT DOCUMENTS

| | | |
|---|---|---|
| CA | 1335412 | 3/1988 |
| CA | 2340282 | 10/2001 |

(Continued)

OTHER PUBLICATIONS

Ellis, J.T., "Polymerase chain reaction approaches for the detection of Neospora caninum and Toxoplasma gondii," International Journal for Parasitology, vol. 28, pp. 1053-1060. (Year: 1998).*

Al-Khatib, K., et al., "Survey of Common Sunflower (*Helianthus annuus*) Resistance to ALS-inhibiting Herbicides in Northeast Kansas". Proceedings of the 21st Sunflower Research Workshop. National Sunflower Association, pp. 210-215; Bismark, ND (Jan. 14-15, 1999).

Al-Khatib, K., et al., "Imazethapyr resistance in common sunflower (*Helianthus annuus*)" Weed Science, 46:403-407 (1998).

Avila, L. A., et al., "Assessment of Acetolactate Synthase (ALS) tolerance to Imazethapyr in Red Rice Ecotypes (Oryza spp) and Imidazolinone Tolerant/Resistant Rice (*Oryza sativa*) Varietites". Pest Management Science, vol. 61, No. 2, pp. 171-178 (2005).

(Continued)

*Primary Examiner* — Young J Kim

(74) *Attorney, Agent, or Firm* — Mintz Levin Cohn Ferris Glovsky & Popeo, P.C.

(57) ABSTRACT

Herbicide resistant sunflower plants comprising two different herbicide-resistant alleles of the sunflower acetohydroxyacid synthase large subunit 1 (AHASL1) gene are described. Methods for making these sunflower plants and methods for controlling weeds or other undesired vegetation growing in the vicinity of these sunflower plants are disclosed. Such methods involve the use of acetohydroxyacid synthase-inhibiting herbicides. Methods for controlling parasitic weeds growing on sunflower plants are also described. Additionally provided are methods for determining the genotype of sunflower plants for AHASL1 gene.

12 Claims, 12 Drawing Sheets

(56) References Cited

U.S. PATENT DOCUMENTS

| | | |
|---|---|---|
| 5,876,932 A | 3/1999 | Fischer |
| 5,928,937 A | 7/1999 | Kakefuda et al. |
| 5,952,553 A | 9/1999 | Croughan |
| 6,043,196 A | 3/2000 | Mayer et al. |
| 6,100,030 A | 8/2000 | McCasky Feazel et al. |
| 6,114,116 A | 9/2000 | Lemieux et al. |
| 6,175,065 B1 | 1/2001 | Schmidt et al. |
| 6,207,425 B1 | 3/2001 | Liu et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,225,105 B1 | 5/2001 | Sathasivan et al. |
| 6,274,796 B1 | 8/2001 | Croughan |
| 6,339,184 B1 | 1/2002 | Smith |
| 6,348,643 B1 | 2/2002 | Kakefuda et al. |
| 6,358,686 B1 | 3/2002 | Lemieux et al. |
| 6,475,736 B1 | 11/2002 | Stanton, Jr. |
| 6,492,582 B2 | 12/2002 | Johnson |
| 6,613,963 B1 | 9/2003 | Gingera et al. |
| 6,627,401 B2 | 9/2003 | Ralhan |
| 6,696,294 B1 | 2/2004 | Konzak |
| 6,943,280 B2 | 9/2005 | Croughan |
| 7,109,196 B2 | 9/2006 | Wang et al. |
| 7,345,221 B2 | 3/2008 | Croughan |
| 7,399,905 B2 | 7/2008 | Croughan |
| 7,495,153 B2 | 2/2009 | Croughan |
| 7,595,177 B2 | 9/2009 | Barnes et al. |
| 7,754,947 B2 | 7/2010 | Croughan |
| 7,786,360 B2 | 8/2010 | Linscombe |
| 7,807,882 B2 | 10/2010 | Leon et al. |
| 2001/0044939 A1 | 11/2001 | Abell et al. |
| 2002/0120962 A1 | 8/2002 | Charne et al. |
| 2002/0138866 A1 | 9/2002 | Gingera et al. |
| 2002/0138881 A1 | 9/2002 | Charne et al. |
| 2003/0087272 A1 | 5/2003 | Kambara et al. |
| 2003/0096277 A1 | 5/2003 | Chen |
| 2003/0097692 A1 | 5/2003 | Jander et al. |
| 2003/0138780 A1 | 7/2003 | Gill et al. |
| 2003/0180929 A1 | 9/2003 | Kafefuda et al. |
| 2003/0217381 A1 | 11/2003 | Croughan |
| 2004/0142353 A1 | 7/2004 | Cheung et al. |
| 2004/0171027 A1 | 9/2004 | Barnes et al. |
| 2004/0172729 A1 | 9/2004 | Moldenhauer et al. |
| 2004/0187178 A1 | 9/2004 | Slinkard et al. |
| 2004/0219675 A1 | 11/2004 | Sainz et al. |
| 2004/0237134 A1 | 11/2004 | Pozniak et al. |
| 2004/0244080 A1 | 12/2004 | Hucl |
| 2005/0044597 A1 | 2/2005 | Konzak |
| 2005/0198705 A1 | 9/2005 | Croughan |
| 2005/0208506 A1 | 9/2005 | Zhao et al. |
| 2005/0283858 A1 | 12/2005 | Yao et al. |
| 2006/0010514 A1 | 1/2006 | Birk et al. |
| 2006/0095992 A1 | 5/2006 | Bowran et al. |
| 2007/0028318 A1 | 2/2007 | Livore et al. |
| 2007/0033670 A1 | 2/2007 | Konzak et al. |
| 2007/0118920 A1 | 5/2007 | Leon et al. |
| 2008/0167186 A1 | 7/2008 | Croughan |
| 2008/0276329 A1 | 11/2008 | Moldenhauer |
| 2009/0025108 A1 | 1/2009 | Croughan |

FOREIGN PATENT DOCUMENTS

| | | |
|---|---|---|
| EP | 0154204 | 11/1985 |
| EP | 0257993 | 3/1988 |
| EP | 0360750 | 3/1990 |
| EP | 0364580 | 4/1990 |
| EP | 0375875 | 7/1990 |
| EP | 0461355 | 12/1991 |
| EP | 0502588 | 9/1992 |
| EP | 0508161 | 10/1992 |
| EP | 0525384 | 2/1993 |
| EP | 1754786 | 4/1996 |
| EP | 0730030 | 9/1996 |
| EP | 0965265 | 12/1999 |
| EP | 1033405 | 9/2000 |
| EP | 1061135 A2 | 12/2000 |
| JP | 8214882 | 8/1996 |
| JP | 2001-057892 | 3/2001 |
| JP | 2003-135098 | 5/2003 |
| JP | 2005-245272 | 9/2005 |
| JP | 2006-515982 | 6/2006 |
| WO | WO9014000 | 11/1990 |
| WO | WO9113159 | 9/1991 |
| WO | WO9208794 | 5/1992 |
| WO | WO9633270 | 10/1996 |
| WO | WO9774218 | 11/1997 |
| WO | WO9802526 | 1/1998 |
| WO | WO9802527 | 1/1998 |
| WO | WO9832706 | 7/1998 |
| WO | WO9919493 | 4/1999 |
| WO | WO9953081 | 10/1999 |
| WO | WO9965292 | 12/1999 |
| WO | WO9965314 | 12/1999 |
| WO | WO0026390 | 5/2000 |
| WO | WO0027182 | 5/2000 |
| WO | WO0053763 | 9/2000 |
| WO | WO0121821 | 3/2001 |
| WO | WO0165922 | 9/2001 |
| WO | WO0182685 | 11/2001 |
| WO | WO0183818 | 11/2001 |
| WO | WO0185970 | 11/2001 |
| WO | WO0192512 | 12/2001 |
| WO | WO0200915 | 1/2002 |
| WO | WO0208794 | 1/2002 |
| WO | WO02092820 | 11/2002 |
| WO | WO03012115 | 2/2003 |
| WO | WO03013225 | 2/2003 |
| WO | WO03014356 | 2/2003 |
| WO | WO03014357 | 2/2003 |
| WO | WO03076574 | 9/2003 |
| WO | WO2004007691 | 1/2004 |
| WO | WO 2004/011908 A2 | 2/2004 |
| WO | WO2004016073 | 2/2004 |
| WO | WO2004022715 | 3/2004 |
| WO | WO2004040012 | 5/2004 |
| WO | WO2004106529 | 12/2004 |
| WO | WO2005020673 | 3/2005 |
| WO | WO2005093093 | 10/2005 |
| WO | WO2006007373 | 1/2006 |
| WO | WO2006024351 | 3/2006 |
| WO | WO2006060634 | 6/2006 |
| WO | WO2006094084 | 9/2006 |
| WO | WO2007005581 | 1/2007 |
| WO | WO2007032807 | 3/2007 |
| WO | WO2007140451 | 12/2007 |
| WO | WO2008124495 | 10/2008 |
| WO | WO2009046334 | 4/2009 |

OTHER PUBLICATIONS

Ayyadevara, S., et al., "Discrimination of Primer 3'—Nucleotide Mismatch by Taq DNA Polymerase during Polymerase Chain Reaction". Analytical Biochemistry, vol. 284, pp. 11-18 (2000); Academic Press.

Barbosa Filho, M.P., et al., "Upland Rice Production in Brazil," Better Crops International, vol. 16, pp. 43-47, Special Supplement, May 2002.

Barrett, M., "Protection of Grass Crops from Sulfonylurea and Imidazolinone Toxicity". Crop Safeners for Herbicides, pp. 195-220 (1990); Academic Press Inc.

Bennett, Full Complement of Clearfield rice varieties: 2009, Delta Farm Press, Feb. 25, 2008 [online]. [Retrieved on Jan. 3, 2010]. Retrieved from the internet: <URL:http://deltafarmpress.com/rice/clearfield-update-0225/> p. 1, paragraph 14, in 1.

Bernasconi, P., et al., "A Naturally Occurring Point Mutation Confers Broad Range Tolerance to Herbicides That Target Acetolactate Synthase". Journal of Biological Chemistry, vol. 270, No. 29, pp. 17381-17385 (1995).

Boutsalis, P., et al., "Molecular Basis of Resistance to Acetolactate Synthase-Inhibiting Herbicides in Sisymbrium Orientale and Bassica Tournefortii". Pesticide Science, vol. 55, pp. 507-516 (1999).

(56) References Cited

OTHER PUBLICATIONS

Brown, M., et al., "Hydrolytic Activation versus Oxidative Degradation of Assert Herbicide, an Imidazolinone Aryl-carboxylate, in Susceptible Wild Oat versus Tolerant Corn and Wheat". Pesticide Biochemistry and Physiology, vol. 27, pp. 24-29 (1987); Academic Press Inc.

Buchheim, J., et al., "Maturation of Soybean Somatic Embryos and the Transition to Plantlet Growth". Plant Physiol., vol. 89, pp. 768-775 (1989).

Chamovitz, D., et al., "The Molecular Basis of Resistance to the Herbicide Norflurazon". Plant Moleculat Biology, vol. 16, pp. 967-974 (1991).

Chang, et al., "Herbicide-resistant forms of Arabidopsis thaliana acetohydroxyacid synthase: characterization of the catalytic properties and sensitivity to inhibitors of four defined mutants". Biochem. J., vol. 333, pp. 765-777 (1998).

Chong, C, et al., "Amino Acid Residues Conferring Herbicide Tolerance in Tobacco Acetolactate Synthase". Biochemical and Biophysical Research Communications, vol. 279, pp. 462-467 (2000); Academic Press Inc.

De Battista, Juan Jose. "Rice Management and Fertilization in Entre Rios Province"; Special Supplement Publication; Better Crops International, vol. 16, pp. 40-42 (May 2002).

Delrio-Lafreniere SA et al., "Simultaneous allele-specific amplification: a strategy using modified primer-template mismatches for SNP detection—application to prothrombin 20210A (factor II) and factor V Leiden (1691A) gene mutations". Molecular Diagnostics, vol. 6, No. 3, pp. 201-209 (2001).

Doberman, A., et al., "Rice Straw Management", Better Crops International, vol. 16, pp. 7-11, Special Supplementa, May 2002.

Duggleby, R. G., et al., "Acetohydroxyacid Synthase". Journal of Biochemistry and Molecular Biology, Korean Society for Biochemistry and Molecular Biology, KR, vol. 33, No. 1, pp. 1-36 (Jan. 2000).

Duggleby, R., "Identification of an Acetolactate Synthase Small Subunit Gene in Two Eukaryotes". Gene, vol. 190, pp. 245-249 (1997).

Fairhurst, et al., "Rice in the Global Food Supply," Better Crops International, vol. 16, pp. 3-6, Special Supplement May 2002.

Finer, J., et al., "Apical Proliferation of Embryogenic Tissue of Soybean [*Glycine max* (L.) Merrill]". Plant Cell Reports, vol. 7, pp. 238-241(1988).

Finer, J.J., et al., "Development of an Embryogenic Suspension Culture of Soybean (*Glycine max*Merill)". Plant Cell, Tissue, and Organ Culture, vol. 15, pp. 125-146 (1988). Kluwer Academic Publishers, Dordrecht Netherlands.

Gallie, D. R., et al., "The Regulation of Gene Expression in Transformed Maize Aleurone and Endosperm Protoplasts: Analysis of Promoter Activity, Intron Enhancement, and mRNA Untranslated Regions on Expression". Plant Physiol., vol. 106, pp. 929-939 (1994).

Gang, Pan et al., "Map-based cloning of a novel rice cytochrome P450 gene CYP81A6 that confers resistance to two different classes of herbicides". Plant Molecular Biology, Kluwer Academic Publishers, DO, vol. 61, No. 6, pp. 933-943 (Aug. 2006).

Hattori, J., et al., "An Acetohydroxyacid Synthase Mutant Reveals a Single Site Involved in Multiple Herbicide Resistance". Molecular and General Genetics, vol. 246, pp. 419-425 (1995); Springer Verlag, Berlin, Germany.

Hattori, J., et al., "Multiple resistance to sulfonylureas and imidazolinones conferred by an acetohydroxyacid synthase gene with separate mutation for selective resistance". Molecular Genetics, vol. 232, pp. 167-173 (1992).

Hershey, H., et al., "Cloning and Functional Expression of the Small Subunit of Acetolactate Synthase from Nicotiana plumbaginifolia". Plant Molecular Biology, vol. 40, pp. 795-806 (1999); Kluwer Academic Publishers; Netherlands.

Inui, Hideyuki, et al., "Herbicide resistance in transgenic plants with mammalian P450 monooxygenase genes". Pest Management Science, vol. 61, No. 3, pp. 286-291 (Mar. 2005).

Jacq, B., et al., "Efficient Production of Uniform Plants from Cotyledon Explants of Sugarbeets (*Beta vulgaris* L.)". Plant Breeding, vol. 110, pp. 185-191 (1993).

Ji-Yun, J., et al., "Rice Production and Fertilization in China," Better Crops International, vol. 16, pp. 26-29, Special Supplement, May 2002.

Kadaru, S., et al., "Development and application of allele-specific PCR assays for imazethapyr resistance in rice (*Oryza sativa*)," Euphytica, vol. 160, pp. 431-438, (2008).

Kaneda, Y., et al., Combination of Thidiazuron and Basal Media with Low Salt Concentrations Increases the Frequency of Shoot Organogenesis in Soybeans [*Glycine max* (I.) Merr.]. Plant Cell Reports, vol. 17, pp. 8-12 (1997).

Kolkman, J. M., et al., Acetohydroxyacid synthase mutations conferring resistance to imidazolinone or sulfonylurea herbicides in sunflower. Theor. Appl. Genet, vol. 109, pp. 1147-1159 (2004).

Koziel, M. G., et al., "Optimizing expression of transgenes with an emphasis on post-transcriptional events". Plant Molecular Biology, vol. 32, pp. 393-405 (1996).

Kulshreshtha, S., et al., "Direct Somatic Embryogenesis and Plant Regeneration from Mature Sugarbeet (*Beta vulgaris* L.) Zygotic Cotyledons". Plant Growth Regulation, vol. 22, pp. 87-92 (1997).

Lai, F. M., et al., "Scale-up of Somatic Embryogenesis in Alfalfa (*Medicago sativa* L.) I Subculture and Indirect Secondary Somatic Embryogenesis". Plant Cell, Tissue and Organ Culture, vol. 37, pp. 151-158 (1994).

Lee, I., et al., "Guidelines for incorporating non-perfectly matched oligonucleotides into target-specific hybridization probes for DNA microarray". Nucleic Acids Research, vol. 32, pp. 681-690 (2004); Oxford University Press.

Lee, Y., et al., "Effect of Mutagenesis at Serine 653 of Arabidopsis thaliana Acetohydroxyacid Synthase on the Sensitivity to Imidazolinone and Sulfonylurea Herbicides". FEBS Letters, vol. 452, pp. 341-345 (1999); Federation of European Biochemical Societies.

Lee, Y., et al., "Identification of the Regulatory Subunit of Arabidopsis thaliana Acetohydroxyacid Synthase and Reconstitution with its Catalytic Subunit". Biochemistry, vol. 40, pp. 6836-6844 (2001).

Lenzner, S., et al., "Plant Regeneration form Protoplasts of Sugar Beet (*Beta vulgaris*)". Physiologia Plantarum, vol. 94, pp. 342-350 (1995); Denmark.

Li D., et al., "A mutation at the Ala122 position of acetohydroxyacid synthase (AHAS) located on chromosome 6D of wheat: improved resistance to imidazolinone and a faster assay for marker assisted selection". Mol. Breeding, vol. 22, pp. 217-225 (2008).

Li, L.,. et al., "An improved rice transformation system using the biolistic method". Plant Cell Reports, vol. 12, pp. 250-255 (1993).

Liu, W., et al., "Somatic Embryo Cycling: Evaluation of a Novel Transformation and Assay System for Seed-Specific Gene Expression in Soybean". Plant Cell, Tissue and Organ Culture, vol. 47, pp. 33-42 (1996).

Mazur, et al., "Isolation and Characterization of Plant Genes Coding for Acetolactate Synthase, the Target Enzyme for Two Classes of Herbicides". Plant Physiol., vol. 85, pp. 1110-1117 (1987).

McGranahan, G. H., et al., "Improved Efficiency of the Walnut Somatic Embryo Gene Transfer System". Plant Cell Reports, vol. 8, pp. 512-516 (1990).

Miki et al., "Transformation of Brassica napus canola cultivars with Arabidopsis thaliana Acetohydroxyacid Synthase Genes and Analysis of Herbicide Resistance". Theor. Appl. Genet., vol. 80, pp. 449-458 (1990).

Miller, J.F., et al., "Registration of Two Oilseed Sunflower Genetic Stocks, SURES-1 and SURES-2 Resistant to Tribenuron Herbicide," Crop Science Society of America, vol. 44 No. 3, pp. 1037-1038 (May 2004).

Milliman, L D., et al., "Characterization of two biotypes of imidazolinone-resistant eastern black nightshade (*Solanum ptycanthum*)". Weed Science, vol. 51, pp. 139-144 (2003).

Moghaddam, B., et al., "The Effect of in Planta TIBA and Proline Treatment on Somatic Embryogenesis of Sugar Beet (*Beta vulgaris* L.)". Euphytica, vol. 112, No. 2, pp. 151-156 (Jan. 2000).

(56) References Cited

OTHER PUBLICATIONS

Mutert, E., et al., "Developments in Rice Production in Southeast Asia", Better Crops International, vol. 15, pp. 12-17, Special Supplement, May 2002.
Newhouse, K., et al., "Mutations in corn (Zea mays L.) Conferring Resistance to Imidazolinone Herbicides". Theor. Appl. Genet., vol. 83, pp. 65-70 (1991); Springer-Verlag.
Newhouse, K., et al., "Tolerance to Imidazolinone Herbicides in Wheat". Plant Physiology, vol. 100, pp. 882-886 (1992).
Nielsen, J. M., et al., "Synergism of Thidiazuron and Benzyladenine in Axillary Shoot Formation Depends on Sequence of Application in Miscanthus X ogiformis 'Giganteus'". Plant Cell, Tissue and Organ Culture, vol. 41, pp. 165-170 (1995).
Odell, et al., "Comparision of Increased Expression of Wild-Type and Herbicide-Resistant Acetolactate Synthase Genes in Transgenic Plants, and Indication of Posttranscriptional Limitation on Enzyme Activity". Plant Physiol., vol. 94, pp. 1647-1654 (1990).
Ott, K., et al., "Rational Molecular Design and Genetic Engineering of Herbicide Resistant Crops by Structure Modeling and Site-directed Mutagenesis of Acetohydroxyacid Synthase". J. Mol. Biol., vol. 263, pp. 359-368 (1996); Academic Press Limited.
Owens, L. D., et al., "Sugarbeet Leaf Disc Culture: An Improved Procedure for Inducing Morphogenesis". Plant Cell, Tissue and Organ Culture, vol. 31, pp. 195-201 (1992).
Pettersson, M., et al., "Molecular haplotype determination using allele-specific PCR and Pyrosequencing technology". Genomics, vol. 82, pp. 390-396 (2003); Reed Elsevier Science.
Pozniak, C. J., et al., "Physiological and Molecular Characterization of Mutation-Derived Imidazolinone Resistance in Spring Wheat". Crop Science, vol. 44, No. 4, pp. 1434-1443 (2004).
Ray et al., "Mutant Acetolactate Synthase Gene is an Efficient in vitro Selectable Marker for the Genetic Transformation of Brassica Juncea (Oilseed Mustard)". Journal of Plant Physiology, vol. 161, pp. 1079-1083 (2004).
Repellin, et al., "Genetic Enrichment of Cereal Crops via Alien Gene Transfer: New Challenges". Plant Cell, Tissue and Organ Culture, vol. 64, pp. 159-183 (2001).
Roesler, K., et. al., "Targeting of the Arabidopsis homomeric acetyl-coenzyme a carboxylase to plastids of rapeseeds". Plant Physiology, vol. 113, pp. 75-81 (1997).
Roussey, I., et al., "In Planta 2,3,5 Triiodobenzoic Acid Treatment Promotes High Frequency and Routine on Vitro Regeneration of Sugarbeet (Beta vulgaris L.) Plant". Plant Cell Reports, vol. 16, pp. 142-146 (1996).
Rutledge, et al. Molecular and General Genetics, vol. 229, pp. 31-40 (1991).
Sathasivan, K., et al., "Molecular Basis of Imidazolinone Herbicide Resistance in Arabidopsis thaliana var. Columbia". Plant Physiology, vol. 97, pp. 1044-1050 (1991).
Sato, S., et al., "Stable Transformation Via Particle Bombardment in Two Different Soybean Regeneration Systems". Plant Cell Reports, vol. 12, pp. 408-413 (1993).
Saxena et al., "Herbicide Resistance in Datura innoxia". Plant Physiol., vol. 86, pp. 863-867 (1988).
Schmitzer, P. R., et al., "Lack of Cross-Resistance of Imazaquin-Resistant Xanthium strumarium Acetolactate Synthase to Flumetsulam and Chlorimuron". Plant Physiol, vol. 103, pp. 281-283 (1993).
Sella, C., et al., "Subunit Association in Acetohydroxy Acid Synthase Isozyme III". Journal of Bacteriology, vol. 175, No. 17, pp. 5339-5343 (Sep. 1993).
Sha, X.Y., "Field Evaluation of Imidazolinone-Tolerant Clearfield Rice (Oryza sativa L.) at Nine Louisiana Locations," CropScience, vol. 47, pp. 1177-1185 (2007).
Shaner, D., et al., "Imidazolinones: Potent Inhibitors of Acetohydroxyacid Synthase". Plant Physiol, vol. 76, pp. 545-546 (1984).
Shivrain, V.K., et al., "Gene flow between Clearfield™rice and red rice," ScienceDirect, Crop Protection, vol. 26 pp. 349-356, (2007).

Snyder, C.S., et al., "Rice Production in the United States—An Overview," Better Crops International, vol. 16, pp. 30-35, Special Supplement, May 2002.
Stein, N., et al., "A new DNA extraction method for high-throughput marker analysis in a large-genome species such as Triticum aestivum'". Plant Breeding, vol. 120, pp. 354-356 (2001).
Swanson, E., et al., "Microspore Mutagenesis and Selection: Canola Plants with Field Tolerance to the Imidazolinones". Theor Appl Genet, vol. 96, pp. 525-530 (1989); Springer-Verlag.
Tan et al., "Herbicidal Inhibitors of Amino Acid Biosynthesis and Herbicide-Tolerant Crops". Amino Acids, vol. 30, pp. 195-204 (2006).
Tan, S., et al., "Imidazolinone-Tolerant Crops: History, Current Status and Future". Pest Managament Science, vol. 61, No. 3, pp. 246-257 (2005).
Tenning, Paul, et al., "Somatic Embryo genesis from zygotic embryos of sugar beet Beta vulgaris". Plant Science, vol. 81, pp. 103-109 (1992).
Tiwari, K.N., "Rice Production and Nutrient Management in India," Better Crops International, vol. 16, pp. 18-22, Special Supplement, May 2002.
Tranel, P. J., et al., "Resistance of Weeds to ALS-Inhibiting Herbicides: What Have We Learned?". Weed Science, Weed Science Society of America, Champaign, IL (US), vol. 50, No. 6, pp. 700-712 (Nov. 2002).
Wagner, J., et al., "Identification of ALS-inhibitor-resistant Amaranthus biotypes using polymerase chain reaction amplification of . . . ". Weed Research, vol. 42, pp. 280-286 (2002).
Warner, Thomas G., "Sweet success with tethered enzyme catalysis". Nature Biotechnology, vol. 16, pp. 720-721 (Aug. 1998).
Weinstock, et al., "Properties of Subcloned Subunits of Bacterial Acetohydroxy Acid Synthases". Journal of Bacteriology, vol. 174, No. 17, pp. 5560-5556 (Sep. 1992); American Society for Microbiology.
Werck-Reichhart, D., et al., "Cytochromes P450 for engineering herbicide tolerance". Trends in Plant Science, Elsevier Science, Oxford, GB, vol. 5, No. 3, p. 116-123 (Mar. 2000).
Werle E., et al., "Convenient single-step, one tube purification of PCR products for direct sequencing". Nucleic Acids Research, vol. 22, No. 20, pp. 4354-4355 (1994).
White, A. D., et al., "Common sunflower resistance to acetolactate synthase-inhibiting herbicides". Weed Science, vol. 50, pp. 432-437 (2002).
White, A.D., et al., "Isolation of Acetolactate Synthase Homologs in Common Sunflowers". Weed Science, Weed Science Society of America, Champaign, IL, vol. 51, No. 6, pp. 845-853 (Nov. 6, 2003).
Wiersma, C., et al., "Isolation, Expression and Phylogenetic Inheiritance of an Acetolactate Synthase Gene from Brassica napus". Mol. Gen. Genet., vol. 219, pp. 413-420 (1989).
Wright, M., et al., "A Simple Method for the Recovery of Multiple Fertile Plants from Individual Somatic Embryos of Soybean [Glycine max (L) Merrill]". In Vitro Cell Dev Bio., vol. 27P, pp. 153-157 (Jul. 1991). Tissue Culture Association.
Wright, T. R., et al., "Cell Selection and Inheritance of Imidazolinone Resistance in Sugarbeet (Beta vulgaris)". Theor. Appl. Genet., vol. 96, pp. 612-620 (1998); Springer-Verlag.
Wu, D., et al., "Allele-specific enzymatic amplification of B-globin genomic DNA for diagnosis of sickle cell anemia". Proceedings of the National Academy of Sciences, vol. 86, pp. 2757-2760 (1989).
Yu Qin et al., "Tolerance to acetolactate synthase and acetyl-coenzyme A carboxylase inhibiting herbicides in Vulpia bromoides is conferred by two co-existing resistance mechanisms". Pesticide Biochemistry and Physiology, vol. 78, No. 1, pp. 21-30 (Jan. 2004).
Zhang, W., et al., "Genetic and agronomic analyses of red rice-Clearfield hybrids and their progeny produced from natural and controlled crosses," Euphytica, vol. 164, pp. 659-668 (2008).
Zhu et al., "Engineering herbicide-resistant maize using chimeric RNA/DNA oligonucleotides". Nature Biotechnology, vol. 18, pp. 555-558 (2000).
Zhu, X. L., "Computational simulations of the interactions between acetyl-coenzyme-A carboxylase and clodinafop: resistance mecha-

(56) References Cited

OTHER PUBLICATIONS nism due to active and nonactive site mutations." J. Chem. Inf. Model., vol. 49, pp. 1936-1843 (Jul. 13, 2009).

Garcia-Torres, et al., "Pre-emergence herbicides for the control of broomrape (*Orobanche cernua* Loefl.) in sunflower (*Helianthus annus* L.)" Weed Research 34(6): 395-402 (Dec. 1994).

Tomlin, C.D.S., ed. The Pesticide Manual, 12th Ed, British Crop Protection Council (2000), pp. 526-535.

Rafael A. Massinga et al., "Gene flow from imidazolinone-resistant domesticated sunflower to wild relatives", Weed Society of America, Weed Science, vol. 51: pp. 854-862 (2003).

Search Report dated Apr. 10, 2017, in Brazilian Patent App. No. PI0809473-0.

* cited by examiner

FIGURE 8

```
            Forward primer
            ─────────────▶
Hap6    TGTTCTCTCCGACTCCAAATCCACCACCACCACCACCACCAC------CACTCAACG  51
Hap1    TGTTCTCTCCGACTCCAAATCCACCACCACCACCACCACCAC------CACTCAACG  51
Hap2    TGTTCTCTCCGACTCCAAATCCACCACCACCACCACCACCAC---------TCAACC  48
Hap4    TGTTCTCTCCGACTCCAAATCCACCACCACCACCAC---------------TCAACC  42
Hap5    TGTTCTCTCCGACTCCAAATCCACCACCACCACCAC---------------TCAACC  42
Hap3    TGTTCTCTCCGACTCCAAATCCACCACCACCACCACCACCACCACCACCACACTCAACC  60
        ************************************               *****

Hap6    ACCGTTACCGGTGCAGCCTTTTGTCTCCCGTTACGCGCCAGATCAACCGAGAAAAGGCGC  111
Hap1    ACCGTTACCGGTGCAGCCTTTTGTCTCCCGTTACGCGCCAGATCAACCGAGAAAAGGCGC  111
Hap2    ACCGTTACAGGCGCAGCCTTTTGTCTCCCGGTACGCGCCAGATCAACCGAGAAAAGGCGC  108
Hap4    ACCGTTACAGGCGCAGCCTTTTGTCTCCCGTTACGCGCCAGATCAACCGAGAAAAGGCGC  102
Hap5    ACCGTTACAGGCGCAGCCTTTTGTCTCCCGTTACGCGCCAGATCAACCGAGAAAAGGCGC  102
Hap3    ACCGTTACAGGCGCAGCCTTTTGTCTCCCGTTACGCGCCTGATCAACCGAGAAAAGGCGC  120
        ******** ** ****************** ******* ********************

Hap6    AGACGTGTTGGTGGAAGCTCTGGAACGGGAAGGTGTCACCGACGTCTTCGCCTACCCCGG  171
Hap1    AGACGTGTTGGTGGAAGCTCTGGAACGGGAAGGTGTCACCGACGTCTTCGCCTACCCCGG  171
Hap2    AGACGTGTTGGTGGAAGCTCTGGAACGGGAAGGTGTCACCGACGTCTTCGCCTACCCCGG  168
Hap4    AGACGTGTTGGTGGAAGCTCTGGAACGGGAAGGTGTCACCGACGTCTTCGCCTACCCCGG  162
Hap5    AGACGTGTTGGTGGAAGCTCTAGAACGGGAAGGTGTCACCGACGTCTTCGCCTACCCCGG  162
Hap3    AGACGTGTTGGTGGAAGCTCTGGAACGGGAAGGTGTCACCGACGTCTTCGCCTACCCCGG  180
        ********************* **************************************
                         ▼
Hap6    CGGCACGTCAATGGAGATCCACCA 195    (SEQ ID NO: 11)
Hap1    CGGCGCGTCAATGGAGATCCACCA 195    (SEQ ID NO: 6)
Hap2    CGGCGCGTCAATGGAGATCCACCA 192    (SEQ ID NO: 7)
Hap4    CGGCGCGTCAATGGAGATCCACCA 186    (SEQ ID NO: 9)
Hap5    CGGCGCGTCAATGGAGATCCACCA 186    (SEQ ID NO: 10)
Hap3    CGGCGCGTCAATGGAGATCCACCA 204    (SEQ ID NO: 8)
        **** *******************
            ◀─────────────
             Reverse primer
```

HERBICIDE-RESISTANT SUNFLOWER PLANTS WITH MULTIPLE HERBICIDE RESISTANT ALLELES OF AHASL1 AND METHODS OF USE

RELATED APPLICATIONS

This application is a division of U.S. patent application Ser. No. 12/594,289, filed Oct. 1, 2009, which is a U.S. national stage application under 35 U.S.C. § 371 of International Application PCT/US2008/059125, filed Apr. 2, 2008, which designates the U.S. and was published by the International Bureau in English as WO 2008/124431 on Oct. 16, 2008, and which claims benefit of priority under 35 U.S.C. § 119 to U.S. Provisional Patent Application No. 60/910,041, filed Apr. 4, 2007 and U.S. Provisional Patent Application No. 61/029,737, filed Feb. 19, 2008; the contents of each which hereby are incorporated by reference herein in their entirety.

FIELD OF THE INVENTION

This invention relates to the field of agriculture, particularly to herbicide-resistant sunflower plants that comprise two different herbicide-resistant alleles of the sunflower acetohydroxyacid synthase large subunit 1 (AHASL1) gene.

BACKGROUND OF THE INVENTION

Acetohydroxyacid synthase (AHAS; EC 4.1.3.18, also known as acetolactate synthase or ALS), is the first enzyme that catalyzes the biochemical synthesis of the branched chain amino acids valine, leucine and isoleucine (Singh (1999) "Biosynthesis of valine, leucine and isoleucine," in *Plant Amino Acid*, Singh, B. K., ed., Marcel Dekker Inc. New York, N.Y., pp. 227-247). AHAS is the site of action of five structurally diverse herbicide families including the sulfonylureas (Tan et al. (2005) *Pest Manag. Sci.* 61:246-57; Mallory-Smith and Retzinger (2003) *Weed Technology* 17:620-626; LaRossa and Falco (1984) Trends Biotechnol. 2:158-161), the imidazolinones (Shaner et al. (1984) *Plant Physiol.* 76:545-546), the triazolopyrimidines (Subramanian and Gerwick (1989) "Inhibition of acetolactate synthase by triazolopyrimidines," in *Biocatalysis in Agricultural Biotechnology*, Whitaker, J. R. and Sonnet, P. E. eds., ACS Symposium Series, American Chemical Society, Washington, D.C., pp. 277-288), the pyrimidinyloxybenzoates (Subramanian et al. (1990) *Plant Physiol.* 94: 239-244) and the sulfonylamino-carbonyltriazolinones (Tan et al. (2005) *Pest Manag. Sci.* 61:246-57; Mallory-Smith and Retzinger (2003) *Weed Technology* 17:620-626). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, flazasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray a herbicide over the top of a wide range of vegetation decreases the costs associated with plant establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone-resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson (1985) *Weed Sci.* 33:469-471). Other crops such as corn (Newhouse et al. (1992) *Plant Physiol.* 100:882-886) and rice (Barrett et al. (1989) *Crop Safeners for Herbicides*, Academic Press, New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al. (1984) *Plant Physiol.* 76:545-546; Brown et al., (1987) *Pestic. Biochem. Physiol.* 27:24-29). Other plant physiological differences such as absorption and translocation also play an important role in sensitivity (Shaner and Robinson (1985) *Weed Sci.* 33:469-471).

Plants resistant to imidazolinones, sulfonylureas, triazolopyrimidines, and pyrimidinyloxybenzoates have been successfully produced using seed, microspore, pollen, and callus mutagenesis in *Zea mays, Arabidopsis thaliana, Brassica napus* (i.e., canola) *Glycine max, Nicotiana tabacum*, sugarbeet (*Beta vulgaris*) and *Oryza sativa* (Sebastian et al. (1989) *Crop Sci.* 29:1403-1408; Swanson et al., 1989 *Theor. Appl. Genet.* 78:525-530; Newhouse et al. (1991) *Theor. Appl. Genet.* 83:65-70; Sathasivan et al. (1991) *Plant Physiol.* 97:1044-1050; Mourand et al. (1993) *J. Heredity* 84:91-96; Wright and Penner (1998) *Theor. Appl. Genet.* 96:612-620; U.S. Pat. No. 5,545,822). In all cases, a single, partially dominant nuclear gene conferred resistance. Four imidazolinone resistant wheat plants were also previously isolated following seed mutagenesis of *Triticum aestivum* L. cv. Fidel (Newhouse et al. (1992) *Plant Physiol.* 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al. (1992) *Plant Physiol.* 100:882-886).

Naturally occurring plant populations that were discovered to be resistant to imidazolinone and/or sulfonylurea herbicides have also been used to develop herbicide-resistant sunflower breeding lines. Recently, two sunflower lines that are resistant to a sulfonylurea herbicide were developed using germplasm originating from a wild population of common sunflower (*Helianthus annuus*) as the source of the herbicide-resistance trait (Miller and Al-Khatib (2004) *Crop Sci.* 44:1037-1038). Previously, White et al. ((2002) *Weed Sci.* 50:432-437) had reported that individuals from a wild population of common sunflower from South Dakota, U.S.A. were cross-resistant to an imidazolinone and a sulfonylurea herbicide. Analysis of a portion of the coding region of the acetohydroxyacid synthase large subunit (AHASL) genes of individuals from this population revealed a point mutation that results in an Ala-to-Val amino acid substitution in the sunflower AHASL protein that corresponds to $Ala_{205}$ in the wild-type *Arabidopsis thaliana* AHASL protein (White et al. (2003) *Weed Sci.* 51:845-853). Earlier, Al-Khatib and Miller ((2000) *Crop Sci.* 40:869) reported the production of four imidazolinone-resistant sunflower breeding lines.

Computer-based modeling of the three dimensional conformation of the AHAS-inhibitor complex predicts several amino acids in the proposed inhibitor binding pocket as sites where induced mutations would likely confer selective resistance to imidazolinones (Ott et al. (1996) *J. Mol. Biol.* 263:359-368). Tobacco plants produced with some of these rationally designed mutations in the proposed binding sites of the AHAS enzyme have in fact exhibited specific resistance to a single class of herbicides (Ott et al. (1996) *J. Mol. Biol.* 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance due to mutations in at least one amino acid in one or more conserved regions. The mutations described therein encode either cross-resistance for imidazolinones and sulfonylureas or sulfonylurea-specific resistance, but imidazolinone-specific resistance is not described. U.S. Pat. No. 5,731,180 and U.S. Pat. No. 5,767,361 discuss an isolated gene having a single amino acid substitution in a wild-type monocot AHAS amino acid sequence that results in imidazolinone-specific resistance. In addition, rice plants that are resistant to herbicides that interfere with AHAS have been developed by mutation breeding and also by the selection of herbicide-resistant plants from a pool of rice plants produced by anther culture. See, U.S. Pat. Nos. 5,545,822, 5,736,629, 5,773,703, 5,773,704, 5,952,553 and 6,274,796.

In plants, as in all other organisms examined, the AHAS enzyme is comprised of two subunits: a large subunit (catalytic role) and a small subunit (regulatory role) (Duggleby and Pang (2000) *J. Biochem. Mol. Biol.* 33:1-36). The AHAS large subunit (also referred to herein as AHASL) may be encoded by a single gene as in the case of *Arabidopsis*, and sugar beet or by multiple gene family members as in maize, canola, and cotton. Specific, single-nucleotide substitutions in the large subunit confer upon the enzyme a degree of insensitivity to one or more classes of herbicides (Chang and Duggleby (1998) *Biochem J.* 333:765-777).

For example, bread wheat, *Triticum aestivum* L., contains three homoeologous acetohydroxyacid synthase large subunit genes. Each of the genes exhibit significant expression based on herbicide response and biochemical data from mutants in each of the three genes (Ascenzi et al. (2003) International Society of Plant Molecular Biologists Congress, Barcelona, Spain, Ref. No. S10-17). The coding sequences of all three genes share extensive homology at the nucleotide level (WO 03/014357). Through sequencing the AHASL genes from several varieties of *Triticum aestivum*, the molecular basis of herbicide tolerance in most IMI-tolerant (imidazolinone-tolerant) lines was found to be the mutation S653(At)N, indicating a serine to asparagine substitution at a position equivalent to the serine at amino acid 653 in *Arabidopsis thaliana* (WO 03/01436; WO 03/014357). This mutation is due to a single nucleotide polymorphism (SNP) in the DNA sequence encoding the AHASL protein.

Multiple AHASL genes are also know to occur in dicotyledonous plants species. Recently, Kolkman et al. ((2004) *Theor. Appl. Genet.* 109: 1147-1159) reported the identification, cloning, and sequencing for three AHASL genes (AHASL1, AHASL2, and AHASL3) from herbicide-resistant and wild type genotypes of sunflower (*Helianthus annuus* L.). Kolkman et al. reported that the herbicide-resistance was due either to the Pro197Leu (using the *Arabidopsis* AHASL amino acid position nomenclature) substitution or the Ala205Val substitution in the AHASL1 protein and that each of these substitutions provided resistance to both imidazolinone and sulfonylurea herbicides.

Given their high effectiveness and low-toxicity, imidazolinone herbicides are favored for agricultural use. However, the ability to use imidazolinone herbicides in a particular crop production system depends upon the availability of imidazolinone-resistant varieties of the crop plant of interest. To produce such imidazolinone-resistant varieties, plant breeders need to develop breeding lines with the imidazolinone-resistance trait. Thus, additional imidazolinone-resistant breeding lines and varieties of crop plants, as well as methods and compositions for the production and use of imidazolinone-resistant breeding lines and varieties, are needed.

SUMMARY OF THE INVENTION

The present invention provides novel, herbicide-resistant sunflower plants that comprise two different herbicide-resistant alleles of the sunflower acetohydroxyacid synthase large subunit 1 (AHASL1) gene. In particular, the sunflower plants of the invention have increased resistance to acetohydroxyacid synthase (AHAS)-inhibiting herbicides, when compared to a wild-type sunflower plant. The herbicide-resistant sunflower plants of the invention comprise a first AHASL1 allele and a second AHASL1 allele, wherein the first and second AHASL1 alleles encode a first and second herbicide-resistant sunflower AHASL1 protein, respectively. The first AHASL1 allele encodes a sunflower AHASL1 protein comprising the A122T amino acid substitution. The second AHASL1 allele encodes a sunflower AHASL1 protein comprising the A205V amino acid substitution or the P197L amino acid substitution. Also provided are sunflower plant parts, tissues, cells, and seeds that comprise the first and second AHASL1 alleles.

The present invention further provides a method for producing a hybrid sunflower plant that comprises resistance to at least one AHAS-inhibiting herbicide. The method involves the cross-pollination of a first sunflower plant with a second sunflower plant so as to produce hybrid sunflower seeds that can be sown and allowed to grow into a hybrid sunflower plant, particularly an F1 hybrid sunflower plant. The first sunflower plant comprises in its genome at least one copy of a first allele of an AHASL1 gene, and the second sunflower plant comprises in its genome at least one copy of a second allele of an AHASL1 gene. Preferably, the first sunflower plant is homozygous for the first allele, and the second sunflower plant is homozygous for the second allele. The first allele encodes a sunflower AHASL1 protein comprising the A122T amino acid substitution. The second allele encodes a sunflower AHASL1 protein comprising the A205V amino acid substitution or the P197L amino acid substitution.

The present invention additionally provides methods for controlling weeds or undesired vegetation in the vicinity of a sunflower plant of the invention. One method comprises applying an effective amount of AHAS-inhibiting herbicide, particularly an imidazolinone or sulfonylurea herbicide, to the weeds and to the sunflower plant. Another method comprises contacting a sunflower seed of the present invention before sowing and/or after pregermination with an effective amount of an AHAS-inhibiting herbicide, particularly an imidazolinone or sulfonylurea herbicide. The present invention further provides the sunflower seeds of the present invention treated with an effective amount of an AHAS-inhibiting herbicide. The sunflower plants and seeds for use in these methods comprise in their genomes a first AHASL1 allele and a second AHASL1 allele. The first AHASL1 allele encodes a sunflower AHASL1 protein comprising the A122T amino acid substitution. The second AHASL1 allele encodes a sunflower AHASL1 protein comprising the A205V amino acid substitution or the P197L amino acid substitution.

The present invention further provides methods for controlling the parasitic weeds Orobanche cumana and Orobanche cernua, also know as broomrape, on infected sunflower plants. The method comprises applying an effective amount of an imidazolinone herbicide to the weeds and to the herbicide-resistant sunflower plant of the present invention, particularly a sunflower plant comprising two A122T alleles or a sunflower plant comprising one AHASL1 A122T allele and one A205V AHASL1 allele.

The present invention provides diagnostic methods for identifying the alleles of the AHASL1 gene in individual sunflower. Such diagnostic methods involve the polymerase chain reaction (PCR) amplification of specific regions of the sunflower AHASL1 gene using primers designed to anneal to specific sites within the sunflower AHASL1 gene such as, for example, sites at or in the vicinity of mutations in the AHASL1 gene. Additionally provided are the primers used in these methods and kits for performing the methods.

BRIEF DESCRIPTION THE DRAWINGS

Figure 4:
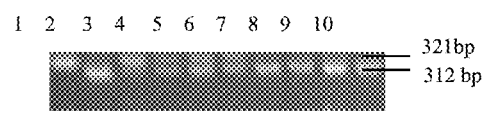

FIG. 4 is a photographic illustration of the products of a PCR amplification reaction using the primers p-AHAS18/pAHAS-19 following agarose gel electrophoresis. Lane 1 GM40 (A122T mutation), Lane 2: L1 (A205V mutation), Lane 3 and 4: H3; Lane 5 and 6: H4; Lane 7 and 8: H1; Lane 9 and 10: L2.

Figure 5:
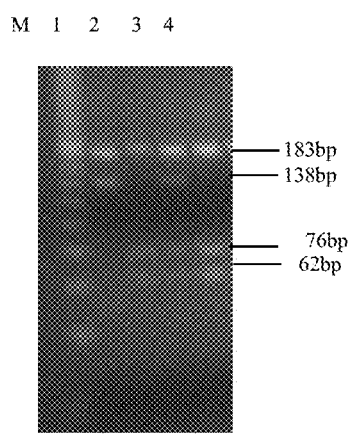

FIG. 5 is a photographic illustration of the products of a restriction enzyme digestion of PCR amplification products with the BmgB I following agarose gel electrophoresis. Lane M, Molecular Weight Marker; Lane 1: BTK47 (Wild type); Lane 2: GM40 (A122T); Lane 3: F1 plant from the cross cmsBTK47×GM40; and Lane 4: cmsGM40 (A122T).

Figure 6:
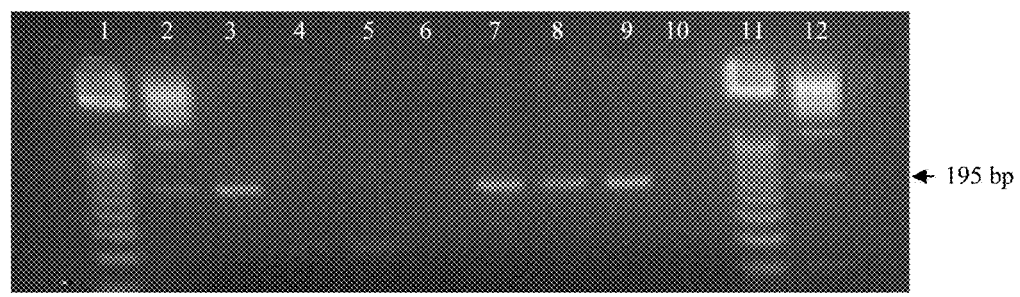

FIG. 6 is a photographic illustration of PCR amplification products obtained using p-AHAS NIDF/AHAS 122 TMU combination. Lane 1, Molecular Weight Marker (25 bp Marker), Lane 2, Molecular Weight Marker (100 bp Marker), Lane 3, 122 Homozygote Individual, Lane 4, 205 Homozygote individual, Lane 5, 197 Homozygote individual, Lane 6, WT (Haplotype 1), Lane 7, 122/WT individual, Lane 8, 122/205 individual, Line 9, 122/197 individual, Line 10, Water (Negative Control), Lane 11, Molecular Weight Marker (25 bp Marker), Lane 12, Molecular Weight Marker (100 bp Marker).

Figure 7:
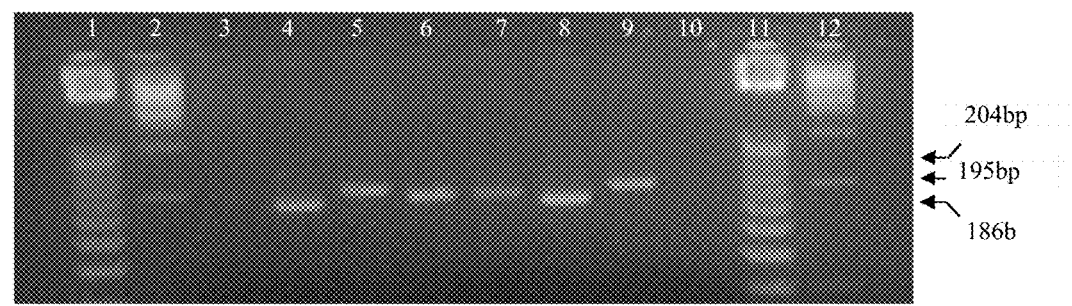

FIG. 7 is a photographic illustration of PCR amplification products obtained using p-AHAS NIDF/AHAS 122 TWT combination. Lane 1, Molecular Weight Marker (25 bp Marker), Lane 2, Molecular Weight Marker (100 bp Marker), Lane 3, 122 Homozygote Individual, Lane 4, 205 Homozygote individual, Lane 5, 197 Homozygote individual, Lane 6, WT (Haplotype 1), Lane 7, 122/WT individual, Lane 8, 122/205 individual, Line 9, 122/197 individual, Line 10, Water (Negative Control), Lane 11, Molecular Weight Marker (25 bp Marker), Lane 12, Molecular Weight Marker (100 bp Marker).

FIG. 8 is a sequence alignment showing differences in the nucleotide sequences of the sunflower AHASL1 haplotypes when sunflower genomic DNA of each haplotype (Hap) is amplified using the primer pairs p-AHAS NIDF/AHAS122TWT or the primer pair p-AHAS NIDF/AHAS 122 TMU. The positions of the primers are shown with arrows. The location of the nucleotide sequence encoding the $(ACC)_n$ repeat (encodes poly-Thr region in putative transit peptide) and INDELs in the AHASL1 nucleotide sequence are in bold type and highlighted, respectively. The $(ACC)_n$ repeat and the INDELS are believed to correspond to the portion of the AHASL1 nucleotide sequence that encodes the transit peptide of AHASL1. The location of the A122T single nucleotide polymorphism (SNP) is indicated by the arrowhead (▼). Numbers at the end of the sequences indicate the expected fragment size of each haplotype when amplified with either the p-AHAS NIDF/AHAS122TWT (Hap1-5) or the p-AHAS NIDF/AHAS 122 TMU (Hap6) primer pair.

Figure 9:
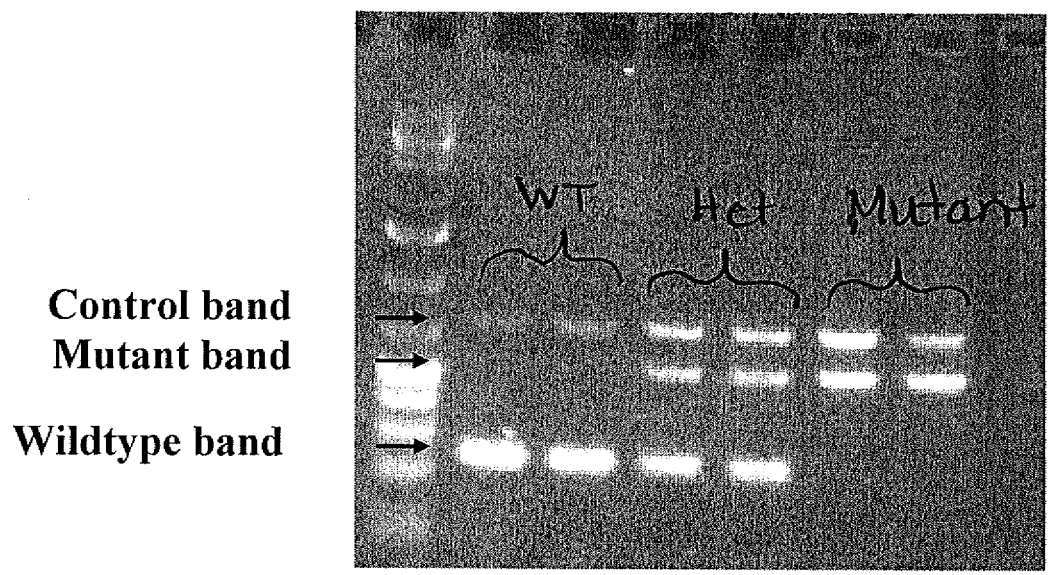

FIG. 9 is a photographic illustration of PCR amplification products obtained using DNA extracts from sunflower tissue from plants that are either heterozygous for the AHASL1 A122T allele (HET), homozygous (MUTANT) for the AHASL1 A122T allele, or wild-type at the AHASL1 locus (WT). PCR amplification was conducted as described in Example 7 and the PCR products separated via gel electrophoresis on a 2% (w/v) agarose gel.

Figure 10:
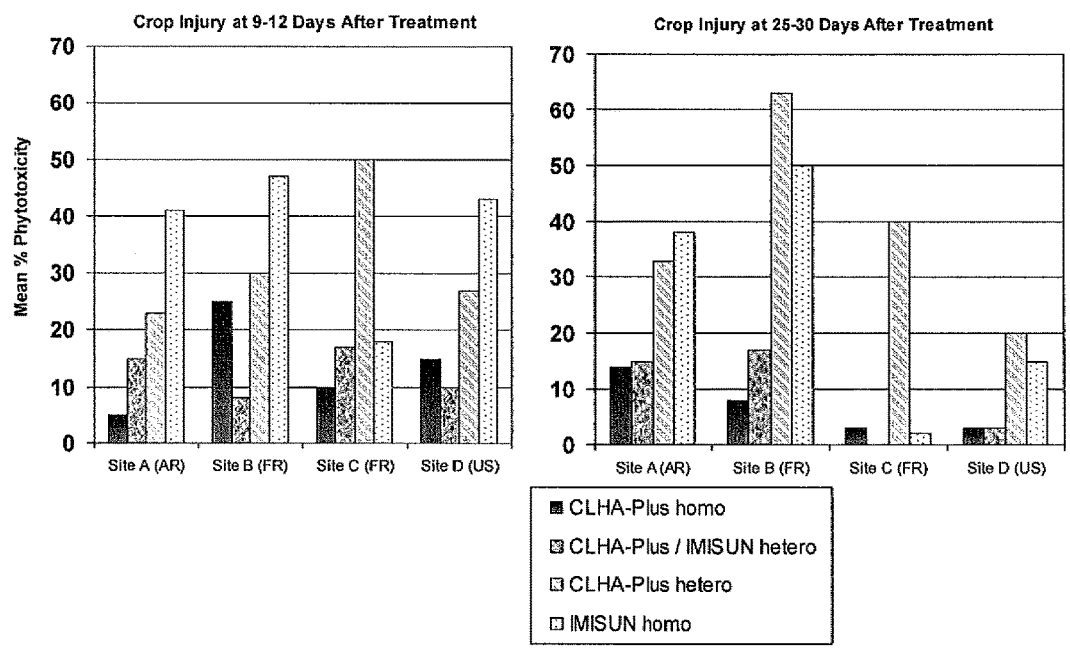
Figure 11:
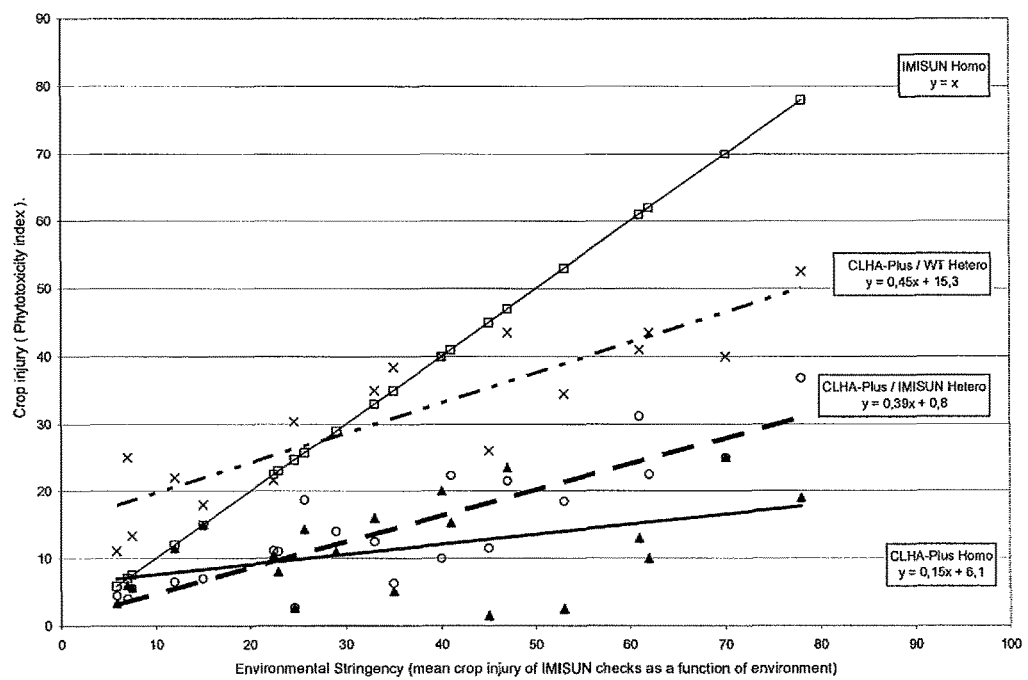

FIG. 10 is a graphical representation of crop injury (Mean % Phytotoxicity) at 200 g ai/ha Imazamox determined at 9-12 days after treatment (left panel) and 25-30 days after treatment (right panel) at four field locations in 2007 for four different types of hybrids. The four sites are: Velva, N. Dak., USA; Angers, FR; Saintes FR; and Formosa, AR. The four different types of hybrids represented in FIG. 10 are A122T homozygous (CLHA-Plus homo), A122T/A205 (CLHA-Plus/IMISUN hetero), A122T heterozygous (CLHA-Plus hetero), and A205V homozygous (IMISUN homo).
The Left Panel FIG. 11 is a graphical representation of crop injury of different types of sunflower hybrids carrying the CLHA-Plus mutation after imazamox application. The four different types of hybrids represented in FIG. 11 are A122T homozygous (CLHA-Plus homo), A122T/A205 (CLHA-Plus/IMI- SUN hetero), A122T heterozygous (CLHA-Plus/WT hetero), and A205V homozygous (IMISUN homo).

Figure 12:
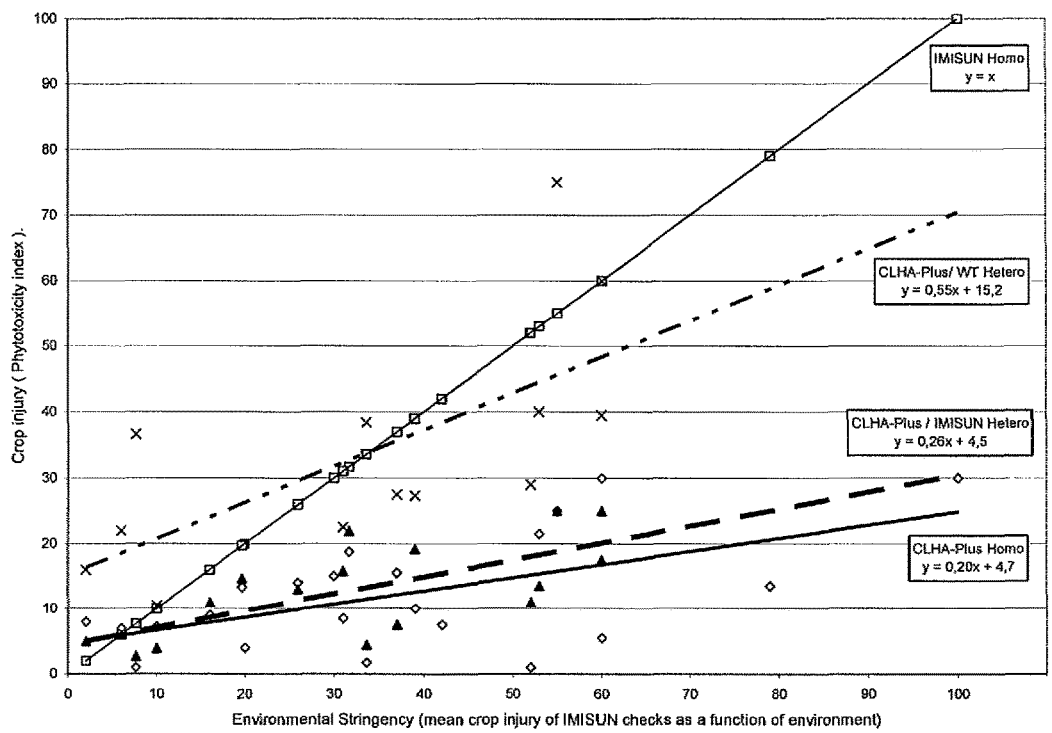

FIG. 12 is a graphical representation of crop injury of different types of sunflower hybrids carrying the CLHA-Plus mutation after imazapyr application (CLHA-Plus homozygous: b=0.20±0.06, P<0.048 CLHA-Plus/IMISUN heterozygous: b: 0.26±0.07, P<0.0019; CLHA-Plus/WT: b: 0.55±0.18, P<0.0109). The four different types of hybrids represented in FIG. 11 are A122T homozygous (CLHA-Plus homo), A122T/A205 (CLHA-Plus/IMISUN hetero), A122T heterozygous (CLHA-Plus/WT hetero), and A205V homozygous (IMISUN homo).

Figure 13:
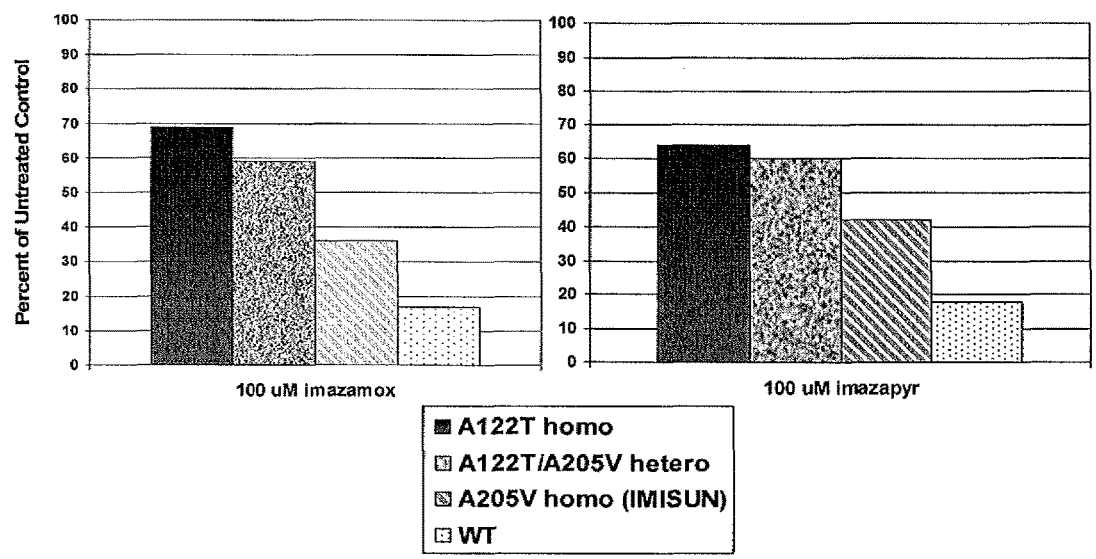

FIG. 13 is a graphical representation of AHAS enzyme activity (expressed as percent of untreated controls) of four sunflower lines in the presence of 100 µM imazamox (left panel) or 100 µM imazapyr (right panel).

Figure 14:
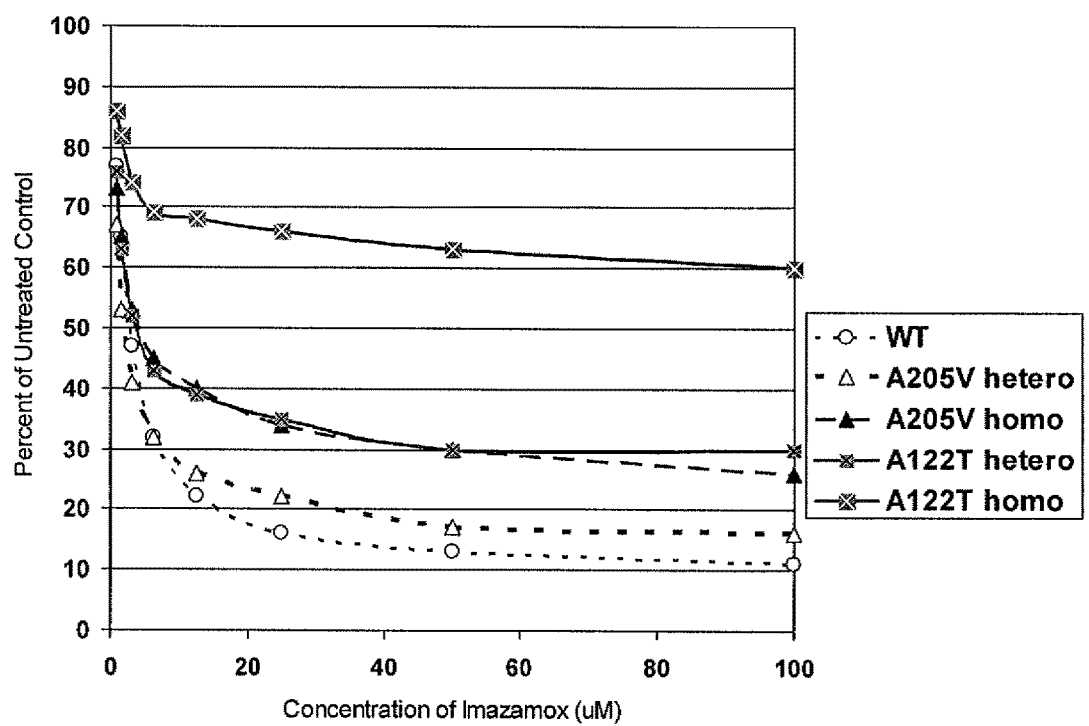

FIG. 14 is a graphical representation of AHAS enzyme activity (expressed as percent of untreated controls) of five sunflower lines in the presence of increasing levels of imazamox.

SEQUENCE LISTING

The nucleic acid and amino acid sequences listed in the accompanying sequence listing are shown using standard letter abbreviations for nucleotide bases, and three-letter code for amino acids. The nucleic acid sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of p-AHAS18.

SEQ ID NO: 2 sets forth the nucleotide sequence of p-AHAS19.

SEQ ID NO: 3 sets forth the nucleotide sequence of p-AHAS NIDF.

SEQ ID NO: 4 sets forth the nucleotide sequence of the AHAS 122 TWT.

SEQ ID NO: 5 sets forth the nucleotide sequence of the AHAS 122 TMU.

SEQ ID NO: 6 sets forth the nucleotide sequence of the portion of AHASL1 from sunflower haplotype 1 (Hap1) that is shown in FIG. 8.

SEQ ID NO: 7 sets forth the nucleotide sequence of the portion of AHASL1 from sunflower haplotype 2 (Hap2) that is shown in FIG. 8.

SEQ ID NO: 8 sets forth the nucleotide sequence of the portion of AHASL1 from sunflower haplotype 3 (Hap3) that is shown in FIG. 8.

SEQ ID NO: 9 sets forth the nucleotide sequence of the portion of AHASL1 from sunflower haplotype 4 (Hap4) that is shown in FIG. 8.

SEQ ID NO: 10 sets forth the nucleotide sequence of the portion of AHASL1 from sunflower haplotype 5 (Hap5) that is shown in FIG. 8.

SEQ ID NO: 11 sets forth the nucleotide sequence of the portion of AHASL1 from sunflower haplotype 6 (Hap6) that is shown in FIG. 8.

SEQ ID NO: 12 sets forth the nucleotide sequence corresponding to the position of the primer p-AHAS NIDF within the AHASL1 nucleotide sequences shown in FIG. 8 (see upper arrow in FIG. 8). Primer p-AHAS NIDF anneals to the nucleotide sequence that is the complement of the nucleotide sequence set forth in SEQ ID NO: 12.

SEQ ID NO: 13 sets forth the nucleotide sequence of the annealing site of the primer AHAS 122 TWT within the AHASL1 nucleotide sequences of Hap1-Hap5 (SEQ ID NOS: 6-10, respectively) shown in FIG. 8 (see lower arrow in FIG. 8).

SEQ ID NO: 14 sets forth the nucleotide sequence of the annealing site of the primer AHAS 122 TMU within the AHASL1 nucleotide sequence of Hap6 (SEQ ID NO: 11) shown in FIG. 8 (see lower arrow in FIG. 8.

SEQ ID NO: 15 sets forth the nucleotide sequence of HA122CF.

SEQ ID NO: 16 sets forth the nucleotide sequence of HA122 wt.

SEQ ID NO: 17 sets forth the nucleotide sequence of HA122mut.

SEQ ID NO: 18 sets forth the nucleotide sequence of HA122CR.

SEQ ID NO: 19 sets forth a partial-length nucleotide sequence encoding a herbicide-resistant AHASL1 protein comprising the A122T amino acid substitution from the sunflower lines S4897 and GM40 as described in WO 2007005581. SEQ ID NO: 19 corresponds to SEQ ID NO: 1 of WO 2007005581.

SEQ ID NO: 20 sets forth a partial-length amino acid sequence of the herbicide-resistant AHASL1 protein encoded by the nucleotide sequence set forth in SEQ ID NO: 19. SEQ ID NO: 20 corresponds to SEQ ID NO: 2 of WO 2007005581.

SEQ ID NO: 21 sets forth the nucleotide sequence encoding a mature, herbicide-resistant AHASL1 protein comprising the P197L amino acid substitution from sunflower line MUT28 as described in WO 2006024351. SEQ ID NO: 21 corresponds to SEQ ID NO: 5 of WO 2006024351.

SEQ ID NO: 22 sets forth the amino acid sequence of the mature, herbicide-resistant AHASL1 protein encoded by the nucleotide sequence set forth in SEQ ID NO: 21. SEQ ID NO: 21 corresponds to SEQ ID NO: 6 of WO 2006024351.

SEQ ID NO: 23 sets forth the nucleotide sequence encoding a mature, herbicide-resistant AHASL1 protein comprising the A205V amino acid substitution from *Helianthus annuus* haplotype 5 as described in GenBank Accession No. AY541455 and Kolkman et al. (2004) Theor. Appl. Genet. 109: 1147-1159. SEQ ID NO: 23 corresponds to nucleotides 244-1959 of the nucleotide sequence of GenBank Accession No. AY541455.

SEQ ID NO: 24 sets forth the amino acid sequence of the mature, herbicide-resistant AHASL1 protein encoded by the nucleotide sequence set forth in SEQ ID NO: 23. SEQ ID NO: 24 corresponds to the amino acids 82-652 of the amino acid sequence encoded by the nucleotide sequence of GenBank Accession No. AY541455.

DETAILED DESCRIPTION OF THE INVENTION

The present invention relates to herbicide-resistant sunflower plants comprising in their genomes two different alleles of the sunflower AHASL1 gene. Each of the two different alleles encode a sunflower AHASL1 protein that comprises an amino acid sequence that differs from the amino acid sequence of a wild-type sunflower AHASL1 by one or more amino acids. Each of the AHASL1 alleles of the present invention is known to confer on a sunflower plant increased resistance or tolerance to AHAS-inhibiting herbicides, particularly imidazolinone and sulfonylurea herbicides. The present invention further relates to methods of making these sunflower plants and to methods for controlling weeds or undesired vegetation growing in the vicinity of the sunflower plants of the present invention.

The present invention is based on the discovery that F1 hybrid sunflower plants that comprise a single copy of each of two different herbicide resistant alleles of the sunflower AHASL1 comprise commercially acceptable levels of resistance to AHAS-inhibiting herbicides. Thus, the present invention finds use in the production of hybrid sunflower plants by allowing a plant breeder to maintain, for example, a first sunflower line that is homozygous for a first herbicide resistant AHASL1 allele and a second sunflower line that is homozygous for a second herbicide resistant AHASL1 allele.

In certain embodiments of the invention, the methods involve the use of herbicide-tolerant or herbicide-resistant plants. By an "herbicide-tolerant" or "herbicide-resistant" plant, it is intended that a plant that is tolerant or resistant to at least one herbicide at a level that would normally kill, or inhibit the growth of, a normal or wild-type plant. In one embodiment of the invention, the herbicide-tolerant plants of the invention comprise a herbicide-tolerant or herbicide-resistant AHASL protein. By "herbicide-tolerant AHASL protein" or "herbicide-resistant AHASL protein", it is intended that such an AHASL protein displays higher AHAS activity, relative to the AHAS activity of a wild-type AHASL protein, when in the presence of at least one herbicide that is known to interfere with AHAS activity and at a concentration or level of the herbicide that is to known to inhibit the AHAS activity of the wild-type AHASL protein. Furthermore, the AHAS activity of such a herbicide-tolerant or herbicide-resistant AHASL protein may be referred to herein as "herbicide-tolerant" or "herbicide-resistant" AHAS activity.

For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Likewise, the terms "imidazolinone-resistant" and "imidazolinone-resistance" are used interchangeably and are intended to be of an equivalent meaning and an equivalent scope as the terms "imidazolinone-tolerant" and "imidazolinone-tolerance", respectively.

The present invention provides plants, plant tissues, plant cells, and host cells with increased resistance or tolerance to at least one herbicide, particularly an imidazolinone or sulfonylurea herbicide. The preferred amount or concentration of the herbicide is an "effective amount" or "effective concentration." By "effective amount" and "effective concentration" is intended an amount and concentration, respectively, that is sufficient to kill or inhibit the growth of a similar, wild-type plant, plant tissue, plant cell, or host cell, but that said amount does not kill or inhibit as severely the growth of the herbicide-resistant plants, plant tissues, plant cells, and host cells of the present invention. Typically, the effective amount or effective concentration of a herbicide is an amount or concentration that is routinely used in agricultural production systems to kill weeds of interest. Such an amount is known to, or can be easily be determined by, those of ordinary skill in the art.

In certain embodiments, the invention provides sunflower plants that comprise commercially acceptable levels of resistance or tolerance to an AHAS-inhibiting herbicide. Unless otherwise indicated herein or otherwise obvious from the context, sunflower plants that comprise such a level of resistance or tolerance to an AHAS-inhibiting herbicide are resistant to or tolerant of an application of an effective amount or effective concentration of at least one AHAS-inhibiting herbicide. As indicated above, the effective amount or concentration of a herbicide is an amount or concentration that is routinely used in agricultural production systems to kill a weed or weeds of interest and that such an amount is known to, or can be easily be determined by, those of ordinary skill in the art.

By "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or lacks herbicide-resistant characteristics that are different from those disclosed herein.

As used herein unless clearly indicated otherwise, the term "plant" is intended to mean a plant at any developmental stage, as well as any part or parts of a plant that may be attached to or separate from a whole intact plant. Such parts of a plant include, but are not limited to, organs, tissues, and cells of a plant. Examples of particular plant parts include a stem, a leaf, a root, an inflorescence, a flower, a floret, a fruit, a pedicle, a peduncle, a stamen, an anther, a stigma, a style, an ovary, a petal, a sepal, a carpel, a root tip, a root cap, a root hair, a leaf hair, a seed hair, a pollen grain, a microspore, a cotyledon, a hypocotyl, an epicotyl, xylem, phloem, parenchyma, endosperm, a companion cell, a guard cell, and any other known organs, tissues, and cells of a plant. Furthermore, it is recognized that a seed is a plant.

In one aspect, the invention provides sunflower plants comprising in its genome at least one copy of an AHASL1 A122T mutant allele and at least one copy of an AHASL1 A205T mutant allele. Such a sunflower plant comprises a commercially acceptable level of tolerance to at least one AHAS-inhibiting herbicide, particularly an imidazolinone herbicide. Such plants find use in agriculture, particularly in methods for controlling weeds involving the use of imidazolinone herbicides as described herein.

In another aspect, the invention provides sunflower plants comprising in its genome at least one copy of an AHASL1 A122T mutant allele and at least one copy of an AHASL1 P197L mutant allele. Such a sunflower plant comprises a commercially acceptable level of tolerance to at least one AHAS-inhibiting herbicide, particularly a sulfonylurea and/or an imidazolinone herbicide. Such plants find use in agriculture, particularly in methods for controlling weeds involving the use of imidazolinone and/or sulfonylurea herbicides as described herein.

The present invention involves the use of a sunflower plant comprising an AHASL1 gene that comprises the A122T mutation. Such an AHASL1 gene encodes an AHASL1 protein comprising the A122T amino acid substitution. The present invention does not depend on the use of a particular sunflower variety, line, or plant comprising an AHASL1 gene with the A122T mutation. Any sunflower plant comprising at least one allele of an AHASL1 gene with the A122T mutation can be used in the methods disclosed herein. In one embodiment of the invention, the AHASL1 gene with the A122T mutation comprises a polynucleotide comprising the nucleotide sequence set forth in SEQ ID NO: 19 or a nucleotide sequence encoding the amino acid the sequence set forth in SEQ ID NO: 20.

An example of a sunflower line comprising at least one copy of the AHASL1 A122T mutant allele is GM40 (see, WO 2007005581 and U.S. Provisional Patent Application Ser. No. 60/695,952; filed Jul. 1, 2005; both of which are herein incorporated by reference). A deposit of seeds of the GM40 sunflower was made under the Budapest Treaty with the Patent Depository of the American Type Culture Collection (ATCC), Manassas, Va. 20110 USA on May 17, 2005 and assigned ATCC Patent Deposit Number PTA-6716. The deposit of sunflower line GM40 was made for a term of at least 30 years and at least 5 years after the most recent request for the furnishing of a sample of the deposit is received by the ATCC. Additionally, Applicants have satisfied all the requirements of 37 C.F.R. §§1.801-1.809, including providing an indication of the viability of the sample. Applicants impose no restrictions on the availability of the deposited material from the ATCC after the issuance of a patent from this application. However, Applicants have no authority to wave any restrictions imposed by law on the transfer of biological material or its transportation in commerce. Applicants do not waive any infringement of Applicants' rights granted under this patent.

Another example of a sunflower line comprising at least one copy of the AHASL1 A122T mutant allele is GM1606 (see, WO 2007005581). A deposit of seeds of the sunflower GM1606 was made under the Budapest Treaty with the Patent Depository of the American Type Culture Collection (ATCC), Manassas, Va. 20110 USA on May 19, 2006 and assigned ATCC Patent Deposit Number PTA-7606. The deposit of sunflower GM1606 was made for a term of at least 30 years and at least 5 years after the most recent request for the furnishing of a sample of the deposit is received by the ATCC. Additionally, Applicants have satisfied all the requirements of 37 C.F.R. §§1.801-1.809, including providing an indication of the viability of the sample. Applicants impose no restrictions on the availability of the deposited material from the ATCC after the issuance of a patent from this application. However, Applicants have no authority to wave any restrictions imposed by law on the transfer of biological material or its transportation in commerce. Applicants do not waive any infringement of Applicants' rights granted under this patent.

The present invention involves the use of a sunflower plant comprising an AHASL1 gene that comprises the A205V mutation. Such an AHASL1 gene encodes an AHASL1 protein comprising the A205V amino acid substitution. The present invention does not depend on the use of a particular sunflower variety, line, or plant comprising an AHASL1 gene with the A205V mutation. Any sunflower plant comprising at least one allele of an AHASL1 gene with the A205V mutation can be used in the methods disclosed herein. In one embodiment of the invention, the AHASL1 gene with the A205V mutation comprises a polynucleotide comprising the nucleotide sequence set forth in SEQ ID NO: 23 or a nucleotide sequence encoding the amino acid the sequence set forth in SEQ ID NO: 24.

Sunflower plants comprising at least one allele of an AHASL1 gene with the A205V mutation are widely used in commercial sunflower production and are readily available. Any of such commercially availably sunflower plant varieties can be used in the methods disclosed herein. Such varieties are available from various commercial seed companies (e.g., Nidera S. A., Buenos Aires, Argentina; Dekalb Genetics Corporation, Dekalb, Ill., USA; Mycogen Seeds, Indianapolis, Ind., USA; Seeds 2000, Breckenridge, Minn., USA; Triumph Seed Company, Ralls, Tex., USA,) sources and include, but are not limited to, Paraíso 101CL, Paraíso 102CL, DKF38, -80CL, 8H429CL, 8H419CL, 8H386CL, 8H358CL, 629CL, 630,CL, 4682NS/CL, 4880NS/CL, Barracuda, Charger, Viper, 620CL, 650CL, and 660CL. In addition, seeds of sunflower plants comprising at least one allele of an AHASL1 gene with the A205V mutation are maintained by the National Center for Genetic Resources Preservation, Fort Collins, Colo., and can be obtained as accession numbers PI 633749 and PI 633750.

The present invention involves the use of a sunflower plant comprising an AHASL1 gene that comprises the P197L mutation. Such an AHASL1 gene encodes an AHASL1 protein comprising the P197L amino acid substitution. The present invention does not depend on the use of a particular sunflower variety, line, or plant comprising an AHASL1 gene with the P197L mutation. Any sunflower plant comprising at least one allele of an AHASL1 gene with the P197L mutation can be used in the methods disclosed herein. Sunflower plants comprising at least one allele of an AHASL1 gene with the P197L mutation have been disclosed in WO 2006024351 and U.S. National Stage patent application Ser. No. 11/659,007, international filing date Jul. 29, 2005; both of which are herein incorporated by reference. In one embodiment of the invention, AHASL1 gene with the P197L mutation comprises a polynucleotide comprising the nucleotide sequence set forth in SEQ ID NO: 21 or a nucleotide sequence encoding the amino acid the sequence set forth in SEQ ID NO: 22.

Three sunflower lines comprising at least one allele of an AHASL1 gene with the P197L mutation have been publicly released by The United States Department of Agriculture Research Service. The three lines are HA 469, RHA 470, and RHA 471. Seeds of each of the three lines can be obtained from Seedstocks Project, Department of Plant Sciences, Loftsgard Hall, N. Dak. State University, Fargo, N. Dak. 58105, US.

The present invention involves sunflower plants with mutations in the sunflower AHASL1 gene. These mutations give rise to sunflower AHASL1 proteins that comprise specific amino acid substitutions in their amino acid sequences when compared to the amino acid sequences of a wild-type sunflower AHASL1 protein. Such amino acid substitutions include, for example, the A122T, A205V, and P197L. By "A122T" is intended the substitution of a threonine for the alanine at the position of the sunflower AHASL1 protein that corresponds to the amino acid position 122 in the *Arabidopsis thaliana* AHASL1 protein. By "A205V" is intended the substitution of a valine for the alanine at the position of the sunflower AHASL1 protein that corresponds to the amino acid position 205 in the *Arabidopsis thaliana* AHASL1 protein. By "P197L" is intended the substitution of a leucine for the proline at the position of the sunflower AHASL1 protein that corresponds to the amino acid position 197 in the *Arabidopsis thaliana* AHASL1 protein.

Unless indicated otherwise or obvious from the context, the amino acid positions in the sunflower AHASL1 protein that are referred to herein are the corresponding positions in the well-studied *Arabidopsis thaliana* AHASL1 protein. The amino acid positions in the sunflower AHASL1 protein that correspond to *Arabidopsis thaliana* AHASL1 amino acid positions 122, 197, and 205 are 107, 182, and 190, respectively. See, WO 2007005581 (Table 4 therein) for additional information on the positions of know amino acid substitutions that confer herbicide resistance to AHASL proteins and their corresponding positions in the sunflower and *Arabidopsis thaliana* AHASL1 proteins.

The present invention provides AHASL proteins with amino acid substitutions at particular amino acid positions within conserved regions of the sunflower AHASL1 proteins disclosed herein. Furthermore, those of ordinary skill will recognize that such amino acid positions can vary depending on whether amino acids are added or removed from, for example, the N-terminal end of an amino acid sequence. Thus, the invention encompasses the amino acid substitutions at the recited position or equivalent position. By "equivalent position" is intended to mean a position that is within the same conserved region as the exemplified amino acid position. Such conserved regions are know in the art (see Table 4 in WO 20070055581) or can be determined by multiple sequence alignments or by other methods known in the art.

The present invention further provides a method for producing a hybrid sunflower plant that comprises resistance to at least one AHAS-inhibiting herbicide. The method involves the cross-pollination of a first sunflower plant with a second sunflower plant so as to produce hybrid sunflower seeds that can be sown and allowed to grow into a hybrid sunflower plant, particularly an F1 hybrid sunflower plant. The first sunflower plant comprises in its genome at least one copy of a first allele of an AHASL1 gene, and the second sunflower plant comprises in its genome at least one copy of a second allele of an AHASL1 gene. Preferably, the first sunflower plant is homozygous for the first allele, and the second sunflower plant is homozygous for the second allele. The first allele encodes a sunflower AHASL1 protein comprising the A122T amino acid substitution. The second allele encodes a sunflower AHASL1 protein comprising the A205V amino acid substitution or the P197L amino acid substitution.

The method for producing a hybrid sunflower plant can further involve harvesting a seed resulting from said crossing and selecting for at least one progeny sunflower plant from said crossing that comprises in its genome said first and said second alleles. Such a progeny can be selected by any method known in the art include PCR amplification of all or part of the AHASL1 gene to determine the alleles that are present in the plant. DNA for use in such a PCR amplification can be obtained from a portion of sunflower seed resulting from the crossing or a portion of a plant grown from such a seed. In Example 2 below, a preferred method of the invention for selecting the desired progeny plant that involves PCR amplification is provided. Alternatively, the progeny plant can be selected by evaluating the performance of the progeny plant in herbicide-resistance test under greenhouse or field conditions as described hereinbelow.

In one preferred embodiment of the invention, a hybrid sunflower plant of the invention is produced by crossing a first sunflower plant that is homozygous for the A205V AHASL1 allele to a second sunflower plant that homozygous of the AHASL1 A122T allele. All of the resulting hybrid seeds and hybrid plants grown from such seed are expected to comprise in their genomes one A205V AHASL1 allele and one AHASL1 A122T allele. In this preferred embodiment, either the first or second sunflower can be the pollen donor for the crossing.

In another preferred embodiment of the invention, a hybrid sunflower plant of the invention is produced by crossing a first sunflower plant that is homozygous for the P197L AHASL1 allele to a second sunflower plant that homozygous of the AHASL1 A122T allele. All of the resulting hybrid seeds and hybrid plants grown from such seed are expected to comprise in their genomes one P197L AHASL1 allele and one AHASL1 A122T allele. In this preferred embodiment, either the first or second sunflower can be the pollen donor for the crossing.

For the purposes of the present invention unless otherwise expressly indicated or apparent from the context, a "progeny plant" is any plant that is descended from at least one plant of the invention and includes, but is not limited to, first, second, third, fourth, fifth, sixth, seventh, eight, ninth, and tenth generation descendants of the plant of the invention. Preferably, such progeny or descendants comprise increased resistance to at least one imidazolinone herbicide when compared to a wild-type plant and such progeny or descendants further comprise at least one mutant AHASL1 allele selected from the group consisting of the A122T, A205V, and P197L alleles. Even more preferably, such progeny or descendants comprise increased resistance to at least one imidazolinone herbicide when compared to a wild-type plant and such progeny or descendants further comprise two different mutant AHASL1 alleles selected from the group consisting of the A122T, A205V, and P197L alleles.

In one embodiment of the invention, the sunflower plants of the invention comprise the A122T allele and produce seeds comprising an extractable seed oil that comprises at least 85% (w/w) oleic acid or 850 g of oleic acid/kg of oil.

Preferably, the % oleic acid content of sunflower seed oil of the present invention is determined by standard methods for the analysis of vegetable oils such as, for example, those methods described in Official Methods of Analysis of Association of the Official Analytical Chemists (1990) W. Horwitz, ed., 14th ed., Washington, D.C. and/or AOCS—American Oil Chemists' Society, Official and Tentative Methods of the American Oil Chemists' Society (1998) 5th ed, Chicago, Ill.

The present invention provides methods for enhancing the tolerance or resistance of a plant, plant tissue, plant cell, or other host cell to at least one herbicide that interferes with the activity of the AHAS enzyme. Preferably, such a herbicide is an imidazolinone herbicide, a sulfonylurea herbicide, a triazolopyrimidine herbicide, a pyrimidinyloxybenzoate herbicide, a sulfonylamino-carbonyltriazolinone herbicide, or mixture thereof. More preferably, such a herbicide is an imidazolinone herbicide, a sulfonylurea herbicide, or mixture thereof. For the present invention, the imidazolinone herbicides include, but are not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate, and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

For the present invention, the sulfonylurea herbicides include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, flazasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfilron, trifloxysulfuron, tritosulfuron, a derivative of any of the aforementioned herbicides, and a mixture of two or more of the aforementioned herbicides. The triazolopyrimidine herbicides of the invention include, but are not limited to, cloransulam, diclosulam, florasulam, flumetsulam, metosulam, and penoxsulam. The pyrimidinyloxybenzoate herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are closely related to the pyrimidinylthiobenzoate herbicides and are generalized under the heading of the latter name by the Weed Science Society of America. Accordingly, the herbicides of the present invention further include pyrimidinylthiobenzoate herbicides, including, but not limited to, the pyrimidinyloxybenzoate herbicides described above.

The herbicide-resistant sunflower plants of the invention find use in methods for controlling weeds. Thus, the present invention further provides a method for controlling weeds in the vicinity of a herbicide-resistant sunflower plant of the invention. The method comprises applying an effective amount of a herbicide to the weeds and to the herbicide-resistant sunflower plant, wherein the plant has increased resistance to at least one herbicide, particularly an imidazolinone or sulfonylurea herbicide, when compared to a wild-type sunflower plant.

In one embodiment, the present invention provides methods for controlling the parasitic weeds known as broomrape (*Orobanche* spp.) on infected sunflower plants. Such *Orobanche* spp. include, for example, *Orobanche cumana* and *Orobanche cernua*. The method comprises applying an effective amount of an imidazolinone herbicide to the weeds and to the herbicide-resistant sunflower plant of the present invention, particularly a sunflower plant comprising two copies of the AHASL1 A122T allele or a sunflower plant comprising one copy of the AHASL1 A122T allele and one copy of the A205V AHASL1 allele. In a preferred embodiment, the imidazolinone herbicide is imazapyr. Preferably, the AHAS-inhibiting herbicide is applied at a later vegetative stage and/or early reproductive stage. More preferably, the herbicide is applied at an early reproductive stage. Most preferably, the herbicide is applied at growth stage R1.

Unless indicated otherwise, the sunflower growth states referred to herein are the growth stages as defined in Schneiter and Miller (1981) *Crop Sci.* 21:901-903.

By providing sunflower plants having increased resistance to herbicides, particularly imidazolinone and sulfonylurea herbicides, a wide variety of formulations can be employed for protecting plants from weeds, so as to enhance plant growth and reduce competition for nutrients. A herbicide can be used by itself for pre-emergence, post-emergence, pre-planting and at planting control of weeds in areas surrounding the plants described herein or an imidazolinone herbicide formulation can be used that contains other additives. The herbicide can also be used as a seed treatment. Additives found in an imidazolinone or sulfonylurea herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, or the like.

The present invention provides non-transgenic and transgenic seeds with increased tolerance to at least one herbicide, particularly an AHAS-inhibiting herbicide, more particularly imidazolinone and sulfonylurea herbicides. Such seeds include, for example, non-transgenic sunflower seeds comprising the herbicide-tolerance characteristics of the sunflower plant S4897, the sunflower plant GM40, the sunflower plant GM1606, the sunflower plant with ATCC Patent Deposit Number PTA-6716, or the sunflower plant with ATCC Patent Deposit Number PTA-7606, and transgenic seeds comprising a polynucleotide molecule of the invention that encodes a herbicide-resistant AHASL protein.

The present invention provides methods that involve the use of at least one AHAS-inhibiting herbicide selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof. In these methods, the AHAS-inhibiting herbicide can be applied by any method known in the art including, but not limited to, seed treatment, soil treatment, and foliar treatment.

Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen and enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasolt, Polymin®), polyethers, polyurethanes, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a suitable gelling agent is carrageen (Satiagel®).

Powders, materials for spreading, and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the AHAS-inhibiting herbicide. In this case, the AHAS-inhibiting herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight.

The AHAS-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The AHAS-inhibiting herbicide may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.
   A) Water-soluble concentrates (SL, LS)
      Ten parts by weight of the AHAS-inhibiting herbicide are dissolved in 90 parts by weight of water or a water-soluble solvent. As an alternative, wetters or other auxiliaries are added. The AHAS-inhibiting herbicide dissolves upon dilution with water, whereby a formulation with 10% (w/w) of AHAS-inhibiting herbicide is obtained.

B) Dispersible concentrates (DC)

Twenty parts by weight of the AHAS-inhibiting herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of AHAS-inhibiting herbicide is obtained.

C) Emulsifiable concentrates (EC)

Fifteen parts by weight of the AHAS-inhibiting herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of AHAS-inhibiting herbicide is obtained.

D) Emulsions (EW, EO, ES)

Twenty-five parts by weight of the AHAS-inhibiting herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of AHAS-inhibiting herbicide is obtained.

E) Suspensions (SC, OD, FS)

In an agitated ball mill, 20 parts by weight of the AHAS-inhibiting herbicide are comminuted with addition of 10 parts by weight of dispersants, welters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained.

F) Water-dispersible granules and water-soluble granules (WG, SG)

Fifty parts by weight of the AHAS-inhibiting herbicide are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the AHAS-inhibiting herbicide, whereby a formulation with 50% (w/w) of AHAS-inhibiting herbicide is obtained.

G) Water-dispersible powders and water-soluble powders (WP, SP, SS, WS)

Seventy-five parts by weight of the AHAS-inhibiting herbicide are ground in a rotor-stator mill with addition of 25 parts by weight of dispersants, wetters and silica gel. Dilution with water gives a stable dispersion or solution of the AHAS-inhibiting herbicide, whereby a formulation with 75% (w/w) of AHAS-inhibiting herbicide is obtained.

I) Gel-Formulation (GF)

In an agitated ball mill, 20 parts by weight of the AHAS-inhibiting herbicide are comminuted with addition of 10 parts by weight of dispersants, 1 part by weight of a gelling agent wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained. This gel formulation is suitable for us as a seed treatment.

2. Products to be applied undiluted for foliar applications. For seed treatment purposes, such products may be applied to the seed diluted.

A) Dustable powders (DP, DS)

Five parts by weight of the AHAS-inhibiting herbicide are ground finely and mixed intimately with 95 parts by weight of finely divided kaolin. This gives a dustable product having 5% (w/w) of AHAS-inhibiting herbicide.

B) Granules (GR, FG, GG, MG)

One-half part by weight of the AHAS-inhibiting herbicide is ground finely and associated with 95.5 parts by weight of carriers, whereby a formulation with 0.5% (w/w) of AHAS-inhibiting herbicide is obtained. Current methods are extrusion, spray-drying or the fluidized bed. This gives granules to be applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

For seed treatment, seeds of the herbicide resistant plants according of the present invention are treated with herbicides, preferably herbicides selected from the group consisting of AHAS-inhibiting herbicides such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, and mixtures thereof, or with a formulation comprising a AHAS-inhibiting herbicide.

The term seed treatment comprises all suitable seed treatment techniques known in the art, such as seed dressing, seed coating, seed dusting, seed soaking, and seed pelleting.

In accordance with one variant of the present invention, a further subject of the invention is a method of treating soil by the application, in particular into the seed drill: either of a granular formulation containing the AHAS-inhibiting herbicide as a composition/formulation (e.g. a granular formulation, with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising at least one AHAS-inhibiting herbicide selected from the group consisting of amidosulfuron, azimsulfuron, bensulfuron, chlorimuron, chlorsulfuron, cinosulfuron, cyclosulfuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the AHAS-inhibiting herbicide or with a formulation comprising the AHAS-inhibiting herbicide is carried out by spraying or dusting the seeds before sowing of the plants and before emergence of the plants.

In the treatment of seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed. For specific crops such as lettuce the rate can be higher.

The present invention provides a method for combating undesired vegetation or controlling weeds comprising contacting the seeds of the resistant plants according to the present invention before sowing and/or after pregermination with an AHAS-inhibiting herbicide. The method can further comprise sowing the seeds, for example, in soil in a field or in a potting medium in greenhouse. The method finds particular use in combating undesired vegetation or controlling weeds in the immediate vicinity of the seed.

The control of undesired vegetation is understood as meaning the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria,* *Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. Other dicotyledonous weeds include, but are not limited to, parasitic plants that infect sunflowers, particularly, *Orobanche* spp. (broomrape), such as, for example, *Orobanche cumana* and *Orobanche cernua*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The sunflower plants of the present invention can be transformed with one or more genes of interest. The genes of interest of the invention vary depending on the desired outcome. For example, various changes in phenotype can be of interest including modifying the fatty acid composition in a plant, altering the amino acid content of a plant, altering a plant's insect and/or pathogen defense mechanisms, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment of the invention, the genes of interest include insect resistance genes such as, for example, *Bacillus thuringiensis* toxin protein genes (U.S. Pat. Nos. 5,366,892; 5,747,450; 5,736,514; 5,723,756; 5,593,881; and Geiser et al. (1986) Gene 48:109).

The present invention provides diagnostic methods for identifying the alleles of the AHASL1 gene in individual sunflower. Such diagnostic methods, which are described below, find use in methods for breeding commercial sunflower cultivars with increased resistance to imidazolinone herbicides. The following terms used herein in the description of these methods are defined below.

A "primer" is a single-stranded oligonucleotide, having a 5' end and a 3' end, that is capable of annealing to an annealing site on a target DNA strand, and the primer serves as an initiation point for DNA synthesis by a DNA polymerase, particularly in a polymerase chain reaction (PCR) amplification. Such a primer may or may not be fully complementary to its annealing site on the target DNA.

An "annealing" site on a strand of a target DNA is the site to which a primer is capable of annealing in the methods of the present invention.

Generally for the amplification of a fragment of a gene by PCR, a pair of primers that anneal to opposite strands of a double-stranded DNA molecule are employed. By standard convention and used herein unless otherwise indicated or apparent from the context, the "forward primer" anneals to the non-coding strand of the gene and the "reverse primer" primer anneals to the coding strand.

Throughout the specification, the terms "mutant allele," "mutant AHASL1 allele," or "mutant AHASL1 gene." Unless indicated otherwise herein or apparent from the context, these terms refer to a polynucleotide that encodes an imidazolinone-tolerant AHASL1 protein comprising a single amino acid substitution when compared to a wild-type AHASL1 protein. Such single amino acid substitutions include, for example, A122T, A205V, and P197L. Typically, such an amino acid substitution is the result of single nucleotide substitution in the AHASL1 coding sequence.

In contrast, unless indicated otherwise, the terms "wild-type allele," "wild-type AHASL1 allele," or "wild-type AHASL1 gene" allele refer to a polynucleotide that encodes an AHASL1 protein.

The invention involves the use of a number of primers for PCR amplification. These primers are described in detail below.

A "forward AHASL1 primer" is a primer that can be used in the methods of the invention involving the PCR amplification of a fragment of a sunflower AHASL1 allele, wherein the fragment extends in a 5' direction from the site of the mutation that gives rise to the A122T amino acid substitution. Preferably, the complement of the annealing site of the "forward AHASL1 primer" is on the 5' side of the (ACC)$_n$ repeat that is shown in FIG. 8.

A "reverse wild-type AHASL1 primer" is a reverse primer that can be used in the methods involving the PCR amplification of a fragment of an AHASL1 allele that does not comprise the mutation that gives rise to the A122T amino acid substitution. The annealing site of the reverse primer is shown in FIG. 8. The 3' terminal (or 3' end) nucleotide of the reverse wild-type AHASL1 primer anneals to the G that is at the site of the SNP in Hap1-Hap5 in FIG. 8. The 3' terminal nucleotide of the reverse wild-type AHASL1 primer is a C.

A "reverse mutant AHASL1 primer" is a reverse primer that can be used in the methods involving the PCR amplification of a fragment of a mutant AHASL1 allele comprising the mutation that gives rise to the A122T amino acid substitution. The annealing site of the reverse primer is shown in FIG. 8. The 3' terminal (or 3' end) nucleotide of the reverse mutant AHASL1 primer anneals to the A in Hap6 that is at the site of the SNP in FIG. 8. The 3' terminal nucleotide of the reverse wild-type AHASL1 primer is a T.

The present invention provides methods for genotyping sunflower AHASL1. The method involves obtaining genomic DNA from a sunflower plant and using the genomic DNA or sample or portion thereof as a template for a first polymerase chain reaction (PCR) amplification comprising the genomic DNA, polymerase, deoxyribonucleotide triphosphates, a forward AHASL1 primer and a reverse wild-type AHASL1 primer. The reverse wild-type AHASL1 primer comprises a nucleic acid molecule that anneals to a nucleotide sequence comprising the nucleotide sequence set forth in SEQ ID NO: 13, wherein the nucleotide that is at the 3' end nucleotide of said reverse wild-type AHASL1 primer is the complement of the nucleotide that is at position 1 of the nucleotide sequence set forth in SEQ ID NO: 13. The method further comprises using the genomic DNA or sample or portion thereof as a template for a second PCR amplification comprising said DNA, polymerase, deoxyribonucleotide triphosphates, said forward AHASL1 primer and a mutant reverse AHASL1 primer. The reverse mutant AHASL1 primer comprises a nucleic acid molecule that anneals to a nucleotide sequence comprising the nucleotide sequence set forth in SEQ ID NO: 14, wherein the nucleotide that is at the 3' end nucleotide of said reverse mutant AHASL1 primer is the complement of the nucleotide that is at position 1 of the nucleotide sequence set forth in SEQ ID NO: 14. The method further comprises detecting the products of said first and said second PCR amplifications.

The reverse wild-type AHASL1 and the reverse mutant AHASL1 primers of the invention anneal to a nucleotide sequence comprising the nucleotide sequence set forth in SEQ ID NO: 13 and 14, respectively, under conditions suitable for the PCR amplification of the portions of the AHASL1 genes or sunflower shown in FIG. 8. The reverse wild-type AHASL1 and the reverse mutant AHASL1 primers additionally have a 3' end nucleotide that consists of a nucleotide that is at the site of the mutation that gives rise to the A122T amino acid substitution. Each of the reverse primers can be but are not required to be fully complementary to their annealing sites and need not extend the full length of the annealing site. Furthermore, the reverse wild-type and mutant AHASL1 primers can comprise additional nucleotides on their 5' end beyond annealing sites. Such additional nucleotides may be but are not required to be fully or even partially complementary to a portion of the sunflower AHASL1 gene. The additional 5' nucleotides can include, for example, restriction enzyme recognition sequences. In one embodiment of the invention, the reverse wild-type AHASL1 and the reverse wild-type AHASL1 primers comprise the nucleotide sequences set forth in SEQ ID NO: 4 and SEQ ID NO: 5, respectively The methods for genotyping sunflower AHASL1 involve the use of a forward AHASL1 primer. Unlike the reverse wild-type AHASL1 and the reverse mutant AHASL1 primers that anneal at the site of the mutation that gives rise to the A122T amino acid substitution, the annealing site of the forward AHASL1 primer nucleotide corresponds to a region of the sunflower AHASL1 gene that is 5' of the (ACC)$_n$ region shown in FIG. 8 so that the haplotypes 1-6 can be distinguished by differences in the length (i.e., bp) of the resulting PCR products. The sequences of these haplotypes in the vicinity of the site of the A122T mutation are shown in FIG. 8. In one embodiment of the invention, the forward AHASL1 primer anneals to a nucleotide sequence comprising the complement of the nucleotide sequence set forth in SEQ ID NO:12. In a preferred embodiment of the invention, the forward AHASL1 primer comprises a nucleotide molecule comprising the nucleotide sequence set forth in SEQ ID NO:3, and in an even more preferred embodiment, the forward AHASL1 primer has the nucleotide sequence set forth in SEQ ID NO:3 with optionally additional nucleotides on the 5' end of the primer. Such additional nucleotides may be but are not required to be fully or even partially complementary to a portion of the sunflower AHASL1 gene. The additional 5' nucleotides can include, for example, restriction enzyme recognition sequences.

The present invention further provides a method for identifying AHASL1 alleles in a sunflower plant. The method involves obtaining genomic DNA from a sunflower plant and using the genomic DNA or sample or portion thereof in at least one PCR amplification. The PCR amplification involves using the genomic DNA as a template for a polymerase chain reaction amplification comprising the genomic DNA, polymerase, deoxyribonucleotide triphosphates, a first forward primer comprising the nucleotide sequence set forth in SEQ ID NO: 15, a first reverse primer comprising the nucleotide sequence set forth in SEQ ID NO: 16, a second forward primer comprising the nucleotide sequence set forth in SEQ ID NO: 17, and a second reverse primer comprising the nucleotide sequence set forth in SEQ ID NO: 18. The method further involves detecting the products of the PCR amplification.

Alternatively, two or even three separate PCR amplifications can be used in the methods of the invention. When two separate PCR amplifications are used, the first PCR amplification involves using the genomic DNA as a template for a first polymerase chain reaction amplification comprising the genomic DNA, polymerase, deoxyribonucleotide triphosphates, a first forward primer comprising the nucleotide sequence set forth in SEQ ID NO: 15, and a first reverse primer comprising the nucleotide sequence set forth in SEQ ID NO: 16. The second PCR amplification involves using the genomic DNA as a template for a second polymerase chain reaction amplification comprising the genomic DNA, polymerase, deoxyribonucleotide triphosphates, a second forward primer comprising the nucleotide sequence set forth in SEQ ID NO: 17, and a second reverse primer comprising the nucleotide sequence set forth in SEQ ID NO: 18. The first PCR amplification can optionally comprise a third primer comprising the nucleotide sequence set forth in SEQ ID NO: 18, and the second PCR amplification can optionally comprise a third primer comprising the nucleotide sequence set forth in SEQ ID NO: 15. The addition of such an optional primer to either one or both of the first and second PCR amplifications allows for the production of a control band that is amplified by the pair of primers comprising the nucleotide sequences set forth in SEQ ID NOS: 15 and 18. The method further involves detecting the products of the first and the second PCR amplifications.

When three separate PCR amplifications are used, the first and second PCR amplifications are the same as described above. The third PCR amplification involves using the genomic DNA as a template for a third polymerase chain reaction amplification comprising the genomic DNA, polymerase, deoxyribonucleotide triphosphates, the first forward primer comprising the nucleotide sequence set forth in SEQ ID NO: 15, and the second reverse primer comprising the nucleotide sequence set forth in SEQ ID NO: 18. The method further involves detecting the products of the first, the second, and the third PCR amplifications.

In one embodiment of the invention, the first forward primer has a nucleotide sequence consisting essentially of SEQ ID NO: 15, the first reverse primer has a nucleotide sequence consisting essentially of SEQ ID NO: 16, the second forward primer has a nucleotide sequence consisting essentially of SEQ ID NO: 17, and/or the second reverse primer has a nucleotide sequence consisting essentially of SEQ ID NO: 18. For the present invention, a primer "consisting essentially of" an exemplified sequence is intended to mean that the primer consists of the entire exemplified sequence but may additionally include nucleotides on the 5' end of the primer. Such additional nucleotides may but are not required to be fully or partially complementary to the target gene for amplification. Because DNA synthesis is initiated from the 3' end of a primer, such additional nucleotides do not change the start site for DNA synthesis when compared to a primer that is identical except for the additional nucleotides.

In a preferred embodiment of the invention, the first forward primer has a nucleotide sequence consisting of SEQ ID NO: 15, the first reverse primer has a nucleotide sequence consisting of SEQ ID NO: 16, the second forward primer has a nucleotide sequence consisting of SEQ ID NO: 17, and/or the second reverse primer has a nucleotide sequence consisting of SEQ ID NO: 18.

Unless otherwise indicated herein, "polymerase" refers to a DNA polymerase, particularly a DNA polymerase that is suitable for use in one or more of the PCR amplifications of the present invention.

In the methods of the invention, the results of PCR amplifications can be detected by, for example, agarose gel electrophoresis of the PCR products followed by ethidium-bromide staining of the DNA in the gel and visualization in the presence of UV light.

The methods of the invention involve the use of PCR for amplifying DNA. Oligonucleotide primers can be designed for use in PCR reactions to amplify corresponding DNA sequences from genomic DNA or cDNA extracted from any organism of interest. Methods for designing PCR primers are generally known in the art and are disclosed in Sambrook et al. (1989) *Molecular Cloning: A Laboratory Manual* (2d ed., Cold Spring Harbor Laboratory Press, Plainview, N.Y.); herein incorporated by reference. See also, Innis et al., eds. (1990) *PCR Protocols: A Guide to Methods and Applications* (Academic Press, New York); Innis and Gelfand, eds. (1995) *PCR Strategies* (Academic Press, New York); Innis and Gelfand, eds. (1999) *PCR Methods Manual* (Academic Press, New York); Dietmaier et al, eds. (2002) *Rapid Cycle Real Time PCR—Methods and Applications*, (Springer Verlag, New York); Theophilus and Raphley, eds. (2002) *PCR Mutation Detection Protocols* (Humana Press, New York); and Bartlett and Stirling, eds. (2003) *PCR Protocols* (Humana Press, New York); all of which are herein incorporated by reference. Other known methods of PCR that can be used in the methods of the invention include, but are not limited to, methods using paired primers, nested primers, single specific primers, degenerate primers, gene-specific primers, mixed DNA/RNA primers, vector-specific primers, partially-mismatched primers, and the like.

The use herein of the term "primer" "or "PCR primer" is not intended to limit the present invention to primers comprising DNA. Those of ordinary skill in the art will recognize that such primers can be comprised of, for example, deoxyribonucleotides, ribonucleotides, and combinations thereof. Such deoxyribonucleotides and ribonucleotides include both naturally occurring molecules and synthetic analogues.

While the invention does not depend on PCR primers of any particular number of nucleotides, it is recognized that the portion of a PCR primer that anneals to its complementary target on the template DNA will generally be between about 10 and 50 contiguous nucleotides, preferably 10, 11, 12, 13, 14, 15, 16, 17, 18, 19, 20, 21, 22, 23, 24, 25, 26, 27, 28, 29, 30, or more contiguous nucleotides. However, a PCR primer of the invention can further comprise on its 5' end additional nucleotides that are not intended to anneal to the target such as, for example, a DNA sequence comprising one or more restriction enzyme recognition sites.

The methods of the invention involve the use of DNA polymerases for PCR amplification of DNA. Any DNA polymerase known in the art that is capable of amplifying a target DNA by PCR may be used in the methods of the invention. The methods of the invention do not depend on a particular DNA polymerase for PCR amplification of DNA, only that such polymerases are capable of amplifying one or more of the plant AHASL genes or fragments thereof. Preferably, the DNA polymerases of the invention are thermostable DNA polymerases, including but not limited to: Taq polymerases; Pfu polymerases; thermostable DNA polymerases from *Thermococcus gorgonarious* which are also known as Tgo DNA polymerases; thermostable DNA polymerases from *Thermococcus litoralis* such as, for example, those that are known as Vent® DNA polymerases (Perler, F. et al. (1992) *Proc. Natl. Acad. Sci.* USA 89, 5577), thermostable DNA polymerases from *Pyrococcus* species GB-D such as, for example, those that are known as Deep Vent® DNA polymerases (Xu, M. et al. (1993) Cell 75, 1371-1377); and modified versions and mixtures thereof.

The methods of the invention involve the amplification of a target DNA sequence by PCR. In certain embodiments of the invention, the target DNA sequence will be amplified directly from a sample comprising genomic DNA isolated from at least one plant or part, organ, tissue, or cell thereof. Those of ordinary skill in the art will recognize that the amount or concentration of genomic DNA will depend on any number of factors including, but not limited to, the PCR conditions (e.g. annealing temperature, denaturation temperature, the number of cycles, primer concentrations, dNTP concentrations, and the like), the thermostable DNA polymerase, the sequence of the primers, and the sequence of the target. Typically, in the embodiments of the invention described herein, the concentration of genomic DNA is at least about 5 ng/μL to about 100 ng/μL.

In addition to PCR amplification, the methods of the invention can involve various techniques of molecular biology including, for example, DNA isolation, particularly genomic DNA isolation, digestion of DNA or PCR products by restriction enzymes and nucleases, DNA ligation, DNA sequencing, agarose gel electrophoresis, polyacrylamide gel electrophoresis, gel electrophoresis in any other suitable matrix for the electrophoretic separation of DNA, the detection of DNA by ethidium-bromide staining, and the like. Such techniques are generally known in the art and are disclosed, for example, in Sambrook et al. (1989) *Molecular Cloning: A Laboratory Manual* (2d ed., Cold Spring Harbor Laboratory Press, Plainview, N.Y.).

The methods of the invention involve the use of genomic DNA isolated from a plant. The methods of the invention do not depend on genomic DNA isolated by any particular method. Any method known in the art for isolating, or purifying, from a plant, genomic DNA, which can be used a source of template DNA for the PCR amplifications described above, can be employed in the methods of the invention. See, for example, Stein et al. ((2001) *Plant Breeding*, 12:354-356); Clark, ed. ((1997) *Plant Molecular Biology—A Laboratory Manual*, Springer-Verlag, New York, pp. 3-15); Miller et al., ((1988) *Nucleic Acids Research*, 16:1215); all of which are herein incorporated by reference. Preferably, such methods for isolating plant genomic DNA are suited, or can be adapted by one of ordinary skill in the art, for the isolation of genomic DNA from relatively large numbers of tissue samples of plants. In an embodiment of the invention, genomic DNA is isolated from sunflower plants using a DNeasy® kit according to the manufacturer's instructions (Qiagen Inc., Valencia, Calif., USA). In another embodiment, genomic DNA is isolated from sunflower plants using a MagneSil® kit according to the manufacturer's instructions (Promega Corp., Madison, Wis., USA).

For the methods of the present invention, genomic DNA can be isolated from whole plants or any part, organ, tissue, or cell thereof. For example, genomic DNA can be isolated from seedlings, leaves, stems, roots, inflorescences, seeds, embryos, tillers, coleoptiles, anthers, stigmas, cultured cells, and the like. Furthermore, the invention does not depend on the isolation of genomic DNA from plants or parts, organs, tissues, or cells thereof that are of any particular developmental stage. The methods can employ genomic DNA that is isolated from, for example, seedlings or mature plants, or any part, organ, tissue or cell thereof. Furthermore, the invention does not depend on plants that are grown under any particular conditions. The plants can be grown, for example, under field conditions, in a greenhouse, or a growth chamber, in culture, or even hydroponically in a greenhouse or growth chamber. Typically, the plants will be grown in conditions of light, temperature, nutrients, and moisture that favor the growth and development of the plants.

The methods of invention involve detecting the products of the PCR amplifications. Typically, the PCR products are detected by first separating the products in a substrate on the basis of molecular weight and then detecting each of the separated PCR products in the substrate. In a preferred embodiment of the invention, the PCR products are detected by agarose gel electrophoresis of the PCR products followed by ethidium-bromide staining of the DNA in the gel and visualization in the gel by florescence in the presence of UV light. However, any detection method suitable for separating polynucleotides can be used to detect the PCR products of the invention including, but not limited to, gel electrophoresis, high performance liquid chromatography, capillary electrophoresis, and the like. Substrates for such methods include, for example, agarose, polyacrylamide, diethylaminoethyl cellulose, hydroxyalkyl cellulose, sepharose, polyoxyethylene, and the like. The PCR amplifications of the invention can involve the use of one or more primers that are labeled, for example, radioactively, or with a fluorescent dye, a luminescent label, a paramagnetic label, or any other label suitable for the detection of nucleic acids. When the PCR amplifications involve one or more of such a labeled primers, the detection step can include the detection of the radioactive, fluorescent, luminescent, paramagnetic, or other label by any methods known in the art for detecting such a label.

The present invention also provides kits for performing the methods for genotyping sunflower AHASL1 as described herein. Such kits comprise primers of the present invention, particularly a forward AHASL1 primer, a reverse wild-type AHASL1 primer, and a reverse mutant AHASL1 primer as described above. Preferably, the forward AHASL1 primer comprises a nucleotide sequence that corresponds to a region of the sunflower AHASL1 gene that is 5' of the $(ACC)_n$ region shown in FIG. 8, the reverse wild-type AHASL1 primer anneals to a nucleotide sequence comprising the nucleotide sequence set forth in SEQ ID NO: 13, and the reverse mutant AHASL1 primer anneals to a nucleotide sequence comprising the nucleotide sequence set forth in SEQ ID NO: 14. More preferably, the forward AHASL1 primer comprises a nucleotide sequence that corresponds to a region of the sunflower AHASL1 gene that is 5' of the $(ACC)_n$ region shown in FIG. 8, the reverse wild-type AHASL1 primer anneals to a nucleotide sequence comprising the nucleotide sequence set forth in SEQ ID NO: 13, and the reverse mutant AHASL1 primer anneals to a nucleotide sequence comprising the nucleotide sequence set forth in SEQ ID NO: 14. More preferably, the forward AHASL1 primer, the reverse wild-type AHASL1 primer, and the reverse mutant AHASL1 primer comprise nucleotide molecules having the nucleotide sequences set forth SEQ ID NO: 3, SEQ ID NO: 4, and SEQ ID NO: 5, respectively. The kits of the invention can optionally comprise one or more of the following: a polymerase, deoxyribonucleotide triphosphates, and instructions for performing the method.

The present invention further provides kits performing the methods for identifying AHASL1 alleles in a sunflower plant. Such kits comprise primers of the present invention, particularly a first forward primer, a first reverse primer, and a second forward primer and a second reverse primer as described above. The first forward primer comprises the nucleotide sequence set forth in SEQ ID NO: 15, the first reverse primer comprises the nucleotide sequence set forth in SEQ ID NO: 16, the second forward primer comprises the nucleotide sequence set forth in SEQ ID NO: 17, and the second reverse primer comprising the nucleotide sequence set forth in SEQ ID NO: 18. The kits can optionally comprise one or more of the following: a polymerase, deoxyribonucleotide triphosphates, and instructions for performing the method.

In addition, the invention provides the primers used in the methods involving PCR amplification described herein. Such primers comprise a nucleotide sequence selected from the group consisting of the nucleotide sequences set forth in SEQ ID NOS: 3, 4, 5, 15, 16, 17, and 18.

The articles "a" and "an" are used herein to refer to one or more than one (i.e., to at least one) of the grammatical object of the article. By way of example, "an element" means one or more elements.

As used herein, the word "comprise," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

Example 1: Phenotypic Interactions of the Imidazolinone-Resistant Mutations in AHASL1 of Sunflower GM40 and GM1606 are mutation-derived lines of sunflower that show high levels of tolerance to imidazolinones due to a point mutation in codon 122 (*Arabidopsis thaliana* nomenclature) of AHASL1 (WO 2007005581 and U.S. Provisional Patent Application Ser. No. 60/695,952; filed Jul. 1, 2005). It was demonstrated that the A122T mutation and derived lines and hybrids homozygous for this mutation show a better tolerance to imazamox than the already known, commercially available, Clearfield sunflowers homozygous for the A205V mutation at AHASL1 (WO 2007005581). Both mutants show incomplete dominance over the wild type, susceptible allele, as in many other examples in the literature. This present invention is based on the discovery that the A122T mutation presents near complete dominance for resistance to imidazolinones over A205V in a range of herbicide applications from 0.5× to 6× of the commercial dose. The present invention provides heterozygous A122T/A205V sunflower plants that show the same tolerance level and pattern of response to increased doses of imidazolinones as do homozygous A122T sunflower plants. Thus, a higher level of tolerance to imidazolinones can be obtained by allelic substitution of A205V by A122T in only one of the parental lines of a Clearfield sunflower, which in turn permits a more rapid deployment of this new allele in the sunflower crop.

To determine the phenotypic interactions of the resistance gene A122T and the Imr1 gene (A205V) already described in IMI-R sunflowers (HA425), F1, F2 and BC1F1 populations from the cross GM40 (A122T)/HA425 (A205V) were evaluated at two herbicide applications rates (80 and 320 g. a. i. Ha$^{-1}$ of imazapyr). No susceptible plants were observed in the F2 and BC1F1 populations resulting from this cross when progeny were evaluated at the lower herbicide rate, indicating that the resistant genes in GM40 and HA425 are alleles of the same locus and that both of them show the same level of resistance to imidazolinones at 1× rate of herbicide application. When F2 and BC1F1 populations were scored at the higher herbicide rate (320 g. a. i. Ha-1), which discriminates both parents, segregation for susceptibility was observed. Only two phenotypic classes could be detected, a resistant class with plants without any injury or slight symptoms and a susceptible phenotype that was killed like the control line HA425. Observed segregation ratios over 450 F2 plants screened were not significantly different from a 3:1 segregation ratio. To confirm these results, F1 plants were backcrossed to HA425 and the resulting BC1F1 plants were screened at 320 g. a.i. ha$^{-1}$ of imazapyr. Observed segregation ratios gave a good fit to a 1:1 R:S ratio, confirming that the resistant gene in GM40 showed complete dominance over the resistant gene in HA425 and that both of them are alleles of the same locus, AHASL1.

To further confirm these results, a molecular marker approach was used. The AHASL1 gene in sunflower presents a simple sequence repeat (SSR) polymorphism which discriminates lines carrying the Imr1 allele from any other sunflower genotype (Kolkman et al. (2004) Theor. Appl. Genet. 109: 1147-1159). PCR amplification of the AHASL1 gene fragment containing this SSR using the primers p-AHAS18 and p-AHAS19 yielded a product of 321 bp for GM40 and BTK47 (original mutagenesis line) and a fragment of 312 bp for HA425. This length variant polymorphism detected in GM40 and HA425 was exploited to investigate the segregation in the F2 and BC1F1 populations derived from crossing both lines. Eighty plants from the F2 population and 50 plants from the BC1F1 population were chosen at random, sampled for DNA isolation, challenged with an imazapyr application rate of 320 g. a. i. ha$^{-1}$ and genotyped using this marker. In the F2 population, 22 plants were killed by the herbicide (S) and 58 showed no symptoms or a slight injury (R). The observed segregation ratio for resistance was not significantly different ($P<0.61$) from the expected segregation ratio for a completely dominant factor segregating in F2 (3R:1S). Observed segregation for the AHASL1 SSR marker (19 A/A: 39 A/B: 22 B/B) fits an expected segregation ratio for a codominant marker segregating in F2 (1:2:1, $P<0.87$). All the susceptible plants genotyped for the AHASL1 SSR were homozygous for the HA425 haplotype (B/B), whereas R-plants were either heterozygous (A/B) or homozygous for the GM40 haplotype (A/A) (Table 4, FIG. 1). The cosegregation of herbicide resistance phenotypes and AHASL1 haplotypes was further assessed on 50 BC1F1 progeny segregating for resistance. Observed segregation ratios for resistance fit a 1:1 ratio ($P<0.78$) as expected for the segregation of one locus in BC1. AHASL1 SSR haplotypes completely cosegregated with phenotypes for herbicide reaction, 23 A/B: 27 B/B. Susceptible progeny were homozygous for the HA425 haplotype (B/B), whereas resistant progeny were heterozygous for HA425 and GM40 haplotypes (A/B).

These results confirm that the resistant gene in GM40 is different from the resistance gene in HA425, that both of them are allelic variants of the locus AHASL1 and, finally, that the gene present in GM40 is completely dominant over the Imr1 allele.

Example 2: Response of Homozygous A122T/A122T and A205V/A205V and Heterozygous A122T/A205V Events to Imazapyr at the Whole Plant Level This experiment was conducted to quantify and contrast the imazapyr sensitivity of sunflower hybrids carrying the A122T and A205V mutations in homozygous (A122T/A122T or A205V/A205V) and heterozygous (A122T/A205V) states in different genetic backgrounds and at the whole plant level.

Materials

Seeds of the different sunflower lines (Table 1) were obtained under field conditions.

TABLE 1

Utilized Sunflower Materials, their
Genealogy, and Type of Mutation Event

| Code | Genealogy | Line (L) or Hybrid (H) | Mutation event (s) |
|---|---|---|---|
| L1 | | L | A205V |
| L2 | | L | A205V |
| H1 | L1 × L2 | H | A205V |
| L3 | cmsGM40 | L | A122T |
| L4 | | L | A122T |
| H2 | L3 × L4 | H | A122T |
| L5 | BTK 47 | L | susceptible |
| H3 | L3 × L2 | H | A205V + A122T |
| H4 | L1 × L4 | H | A205V + A122T |

Lines L1 and L2 are male sterile and restorer breeding lines, respectively, which carry the A205V allele in homozygous condition. L5, BTK 47, is a maintainer line which was utilized as initial material to develop the GM40 line. GM40 is the original line which carries the A122T mutation in the homozygous state (ATCC Patent Deposit Number PTA-6716; see WO 2007005581). L4 is a BC2F4 restorer line derived from the cross R701*3/GM40 using marker assisted backcrossing to select the most similar plant to the recurrent parent in each backcross generation. R701 is a susceptible restorer line with good combining ability. After two generations of backcrossing the most similar plant to R701 was selfed and its progeny was selected for imazapyr resistance. Homozygous A122T plants were selected among the resistant progeny by using a molecular marker diagnostic of the A122T mutation that is described hereinbelow. CMS GM40 is the male sterile version of GM40 which was developed from the BC1F1 generation from the cross cmsBTK47/*2 GM40 using the same diagnostic marker to distinguish homo and heterozygous plants for the A122T allele.

Methods

Diagnostic Marker for the A122T Mutation

An allele-specific PCR assay is described for high-throughput genotyping of sunflower plants carrying the A122T mutation in AHASL1. The assay permits one: (1) to detect the individuals that carry the mutation; (2) to determine the zygosity of these individuals; and (3) to distinguish resistant plants that carry this mutation from plants that contain the A205V mutation.

PCR primers were taken from those provided by Kolkman et al. ((2004) Theor. Appl. Genet. 109: 1147-1159) to amplify a fragment of the sunflower AHASL1 sequence that includes the A122T mutation and an insertion-deletion polymorphism ("INDEL") and that can be used to distinguish the sequence of A122T mutation from the sequence of the already known mutation A205V.

The names and sequences of these primers are:

```
                                          (SEQ ID NO: 1)
p-AHAS18 5'-ttcctccccgtttcgcattac-3'

(SEQ ID NO: 2)
p-AHAS19 5'-cgccgccctgttcgtgac-3'
```

The reaction mix was as follows: 1 U Taq DNA Polymerase, 70 ng genomic sunflower DNA, 25 μg BSA, and have a final concentration of 100 μM of each dNTP, 0.25 μM of each primer, 90 mM Tris-HCl pH8, 20 mM $(NH_4)_2SO_4$ and 2.5 mM $MgCl_2$. The PCR program consists in an initial denaturation step of 94° C. for 2 min, followed by 40 cycles of 30 sec at 94° C., 30 sec at 56° C. and 30 sec at 72° C., followed by a final elongation step at 72° C. for 10 min.

The predicted fragment size for BTK47 (or GM40) using the abovementioned primers is 321 bp and the predicted fragment size based on GenBank Accession No. AY541455 for the sunflower haplotype that carries the A205V mutation is 312 bp. FIG. 4 shows that the PCR reaction described permits to discriminate both A122T and A205V mutants based on the presence of an INDEL polymorphism between their sequences.

The amplified products were restricted and the resulting fragments were resolved in an agarose gel. Restriction reaction consists in 10 μl of the amplification product, BSA 1× (100 μg/ml), NEBuffer 3 1× (100 mM NaCl, 50 mM Tris HCl, 10 mM MgCl2, 1 mM ditiotreitol pH 7.9) and 2.5 U BmgB I. This mix was incubated at 37° C. for 3 hours. The predicted fragment size after restriction for wild type and A122T plants are the following:

The wild type will display fragments of 183+138 bp. GM40 (A122T): display fragments of 183+76+62 bp. Heterozygous individuals will display fragments of 183+138+76+62 bp. FIG. 5 shows that using this method fragments of the expected size are obtained and that it is possible to detect A122T carriers from wild-type plants and also, that it is possible to discriminate between homo and heterozygous individuals for the A122T mutation.

Herbicide Treatments

Seeds were sown in Petri dishes and, after germination, plantlets were transplanted to pots of 10 cm of diameter in a potting media consisting of equal parts of vermiculite, soil and sand. Plants were grown in a greenhouse under natural light conditions supplemented with 400 W sodium halide lamps to provide a 16 hr daylength. Day/night temperatures were 25 and 20° C., respectively. At the V2-V4 stage (Schneiter & Miller (1981) Crop Sci. 21:901-903) 10 plants of each genotype were randomly assigned to each treatment consisting of eight imazapyr doses (0, 40, 80, 160, 240, 320, 400 and 480 g ai/ha, corresponding to untreated, 0.5×, 1×, 2×, 3×, 4×, 5× and 6×, respectively), and a zero-time biomass determination. Experiment was arranged as a randomized block design with a full factorial (sunflower line× treatment) arrangement of treatments and 10 replications.

On the day of herbicide application ten plants of each genotype were cut at the cotyledonal node and dried at 60° C. for 48 hrs for zero-time dried weight determination.

The remaining plants were maintained for 14 days after imazapyr treatment (DAT) and their height, Phytotoxicity Index (PI) and above ground dry biomass were determined. Height was determined as the distance between the cotyledonal node and the apex of each plant. Above ground biomass data from each line were converted to biomass accumulation after application by subtracting the appropriate average zero-time biomass from each sample. Dry biomass data were converted to percentages of the untreated control plants within each line to allow direct comparisons between groups. PI is a phenotypic scale from 0 to 9 that was assessed for each plant by visual inspection. Plants without any symptoms were recorded as "0", increasing levels of stunting and chlorosis with respect to the untreated control plants were recorded as "1" to "4", increasing levels of leaf abnormalities and leaf necrosis were recorded from "5" to "8", and dead plants with total necrosis of the apex were recorded as "9".

Results

Height

Height reduction of the susceptible line was 85% at the lower rate of imazapyr application (0.5×). From 1× to 6× height reduction in this line was approximately 85% of the untreated control plants. Height of the sunflower lines and hybrid carrying the A205V mutation in homozygous condition did not differ from the untreated controls when a rate of 0.5× or 1× of imazapyr was applied. From 2× to 6×, these lines showed a significant reduction in height which reached 69.6%+/−3.9 of the untreated controls (Table 2 and FIG. 1). In contrast, sunflower lines carrying the A122T mutation in homozygous condition exhibited a reduced height reduction (from 0.1% to 18.8% of the untreated controls for 0.5× and 6× rate of imazapyr, respectively). Both groups of lines showed a significative difference between them for their response to an increase in herbicide rate from 2× to 6× (Table 2 and FIG. 1).

Figure 1:
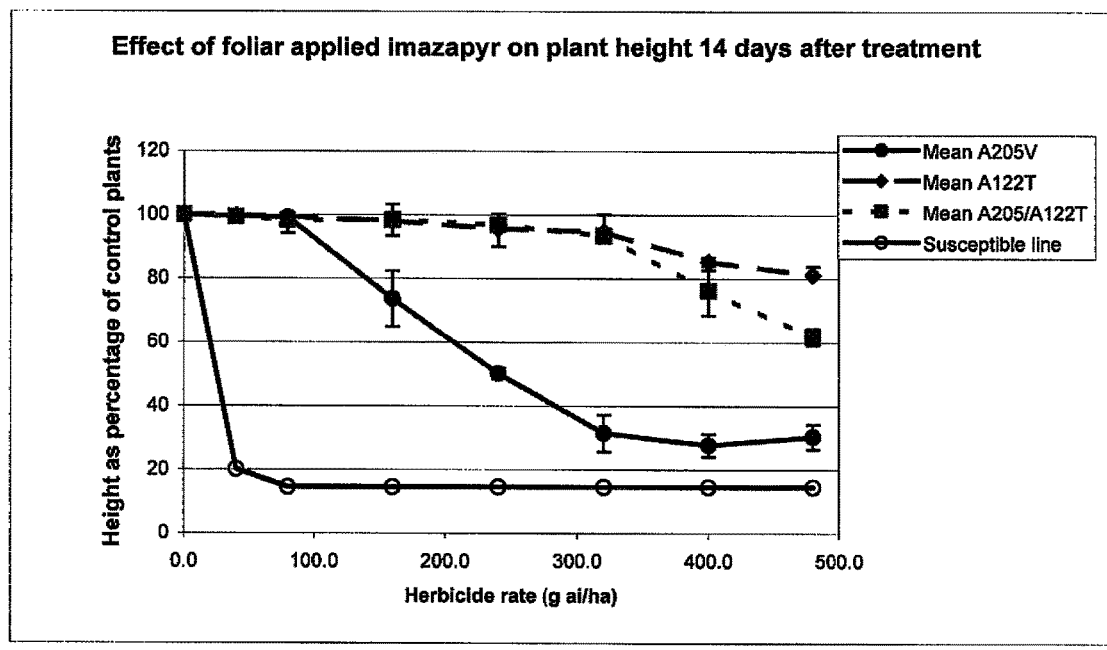
FIG. 1 is a graphical representation of the effect of the foliar application of imazapyr on plant height 14 days after treatment for homozygous materials for the mutation events A122T and A205V and heterozygous genotypes A205+A122T. Mean height (% of untreated plots) are represented by symbols and error bars represent the standard deviation of the means.

The materials with both mutant alleles at AHASL1 (heterozygotes A122T/A205V) showed a height reduction from 0.6% to 38.2%+/−2.7 of the untreated controls for 0.5× to 6× rate of herbicide application. This reduction in height for heterozygous materials did not differ from the reduction observed for homozygotes A122T/A122T but was lesser than that recorded for homozygotes A205V/A205V (FIG. 1). In fact, mean height reduction in heterozygous materials was not different than that observed in homozygous A122T/A122T plants at any doses of herbicide application, but was statistically different from that observed in homozygous A205V/A205V plants form 2× to 6× rates of herbicide application (Table 2).

Phytotoxicity Index

Figure 2:
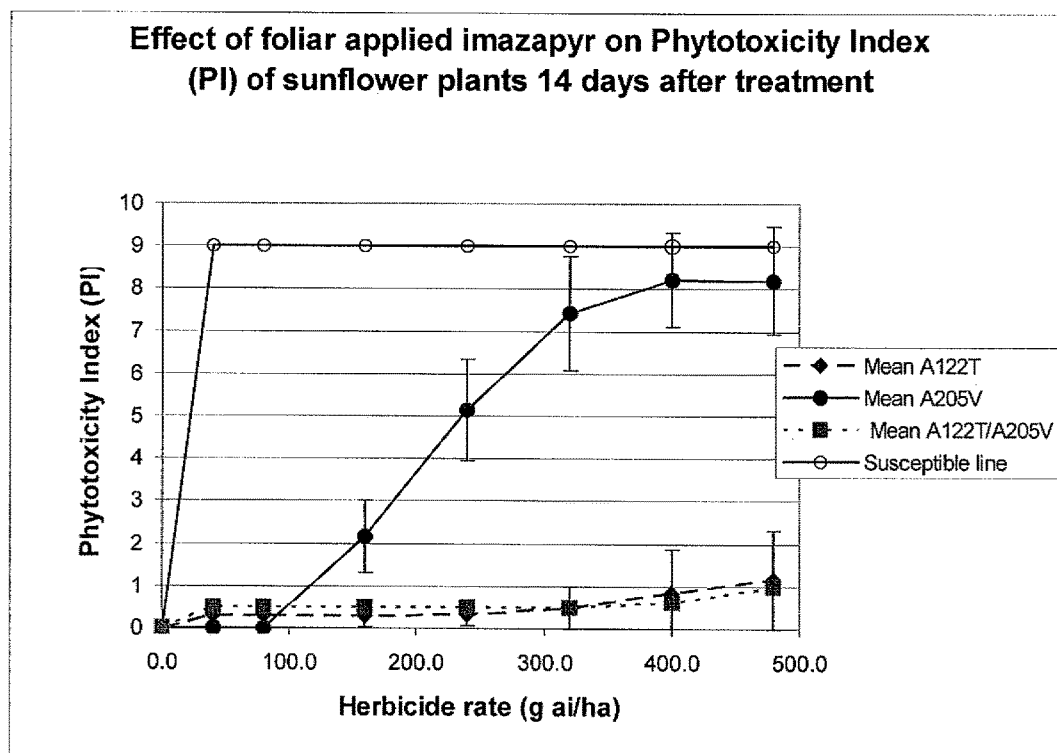
FIG. 2 is a graphical representation of the effect of the foliar application of imazapyr on Phytotoxicity Index (PI) 14 days after treatment for homozygous materials for the mutation events A122T and A205V and heterozygous genotypes A205+A122T. Mean PI are represented by symbols and error bars represent the standard deviation of the means.

Both mutants in homozygous condition showed great differences in their response to the increase in herbicide rate from 0.5× to 6× (FIG. 2). Sunflower lines carrying the A122T mutation in homozygous condition showed a slight reduction in leaf size and lighter green color than the control plants as the herbicide rate increased (Table 3). In contrast, plants carrying the A205V mutation did not show any injury at 0.5× or 1× of herbicide rate, but the level of injury (chlorosis, leaf deformation and leaf necrosis) increased quickly from 2× to 6× (Table 3). The two mutants in homozygous condition differed significantly from each other for the phytotoxicity index from 2× to 6× (Table 3). Heterozygous A122T/A205V materials showed the same pattern of response as the homozygous A122T/A122T materials. In fact, they showed only a lighter green color than the control plants at any rate of herbicide application and smaller leaf size than the control plants at 5× and 6× rates which determined only a PI of 1 at the higher dose (FIG. 2).

Above Ground Dry Weight Biomass

Figure 3:
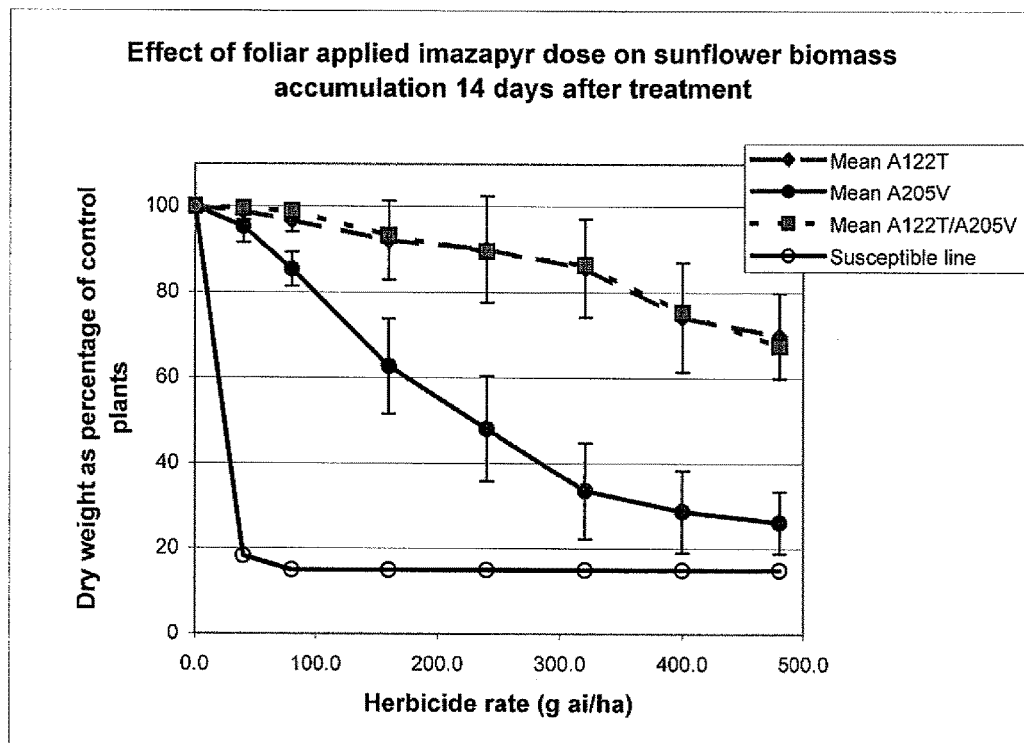
FIG. 3 is a graphical representation of the effect of the foliar application of imazapyr on biomass accumulation 14 days after treatment for homozygous materials for the mutation events A122T and A205V and heterozygous genotypes A205+A122T. Mean dry biomass (% of untreated plots) are represented by symbols and error bars represent the standard deviation of the means.

Dose response curves for dry weight of mutants A122T and A205V are shown in FIG. 3. Biomass weight of event A122T in homozygous condition was reduced with respect to control plants at 4×, 5× and 6× rates, and this reduction reached 25% for the higher dose. Meanwhile, dry weight of event A205V was reduced with respect to the control plants from 0.5× (40 g ai/ha) to 6×. Both mutants showed significant differences between them with respect to this variable from 0.5× to 6× (Table 4). Heterozygous A122T/A205V materials showed exactly the same trend as homozygous A122T materials (FIG. 3, Table 4). They showed a reduction in biomass weight from 0.3% to 33% for 0.5× to 6× rates of herbicide application which did not differ from that recorded for homozygous A122T individuals at any rate. However, heterozygous materials showed significant differences with respect to homozygous A205V individuals for dry matter accumulation from 3× to 6× rates of herbicide application (Table 4).

Conclusions

Heterozygous materials carrying both mutant alleles at the AHASL1 locus showed the same level of tolerance and pattern of response for plant height, phytotoxicity index and dry matter accumulation, to increasing rates of imazapyr application than homozygous A122T materials and this level of tolerance is better than that expressed by homozygous A205V materials.

TABLE 2

Effect of different doses of imazapyr on plant height 14 days after treatment for three sunflower genotypes carrying the A205V mutation event, three genotypes carrying the A122T mutation event, two genotypes carrying the A205V/A122T mutation event and one susceptible line.

| | WT | A205V | | | | | A122T | | | | |
|---|---|---|---|---|---|---|---|---|---|---|---|
| Dose | L5 | H1 | L1 | L2 | Mean | SD | H2 | L3 | L4 | Mean | SD |
| 0 | 100.00 | 100 | 100 | 100 | 100 | 0.0 | 100 | 100 | 100 | 100 | 0 |
| 0.5 | 20.14 | 99.5 | 100.0 | 99.2 | 99.6 | 0.4 | 99.2 | 100.4 | 100.0 | 99.9 | 0.6 |
| 1 | 14.58 | 99.5 | 100.0 | 98.1 | 99.2 | 1.0 | 98.6 | 99.9 | 100.0 | 99.5 | 0.8 |
| 2 | 14.58 | 78.6 | 78.9 | 63.6 | 73.7** | 8.8 | 100.3 | 92.0 | 101.8 | 98.0 | 5.3 |
| 3 | 14.58 | 48.4 | 50.0 | 51.9 | 50.1** | 1.8 | 99.6 | 90.5 | 97.0 | 95.7* | 4.7 |
| 4 | 14.58 | 28.9 | 38.1 | 27.5 | 31.5** | 5.8 | 101.0 | 90.8 | 92.1 | 94.6** | 5.6 |
| 5 | 14.58 | 25.3 | 31.8 | 26.0 | 27.7** | 3.6 | 87.0 | 84.4 | 84.8 | 85.4** | 1.4 |
| 6 | 14.58 | 27.1 | 34.7 | 29.3 | 30.4** | 3.9 | 79.6 | 84.4 | 79.8 | 81.2** | 2.7 |

| | A122T/A205V | | | | Difference between A205V vs | | Difference between A1222T vs | |
|---|---|---|---|---|---|---|---|---|
| Dose | H3 | H4 | Mean | SD | A205V/A122T | P-value | A205V/A122T | P-value |
| 0 | 100.0 | 100.0 | 100.0 | 0.0 | 0.00 | — | 0.00 | — |
| 0.5 | 98.7 | 100.0 | 99.4 | 0.5 | 0.21 | 0.803 | 0.49 | 0.584 |
| 1 | 97.0 | 99.6 | 98.3 | 0.9 | 0.89 | 0.613 | 1.21 | 0.513 |
| 2 | 96.7 | 100.0 | 98.3 | 1.2 | −24.63 | 0.031 | −0.32 | 0.933 |
| 3 | 93.8 | 100.0 | 96.9 | 2.2 | −46.79 | 0.026 | −1.22 | 0.790 |
| 4 | 92.0 | 95.0 | 93.5** | 1.1 | −62.01 | 0.001 | 1.15 | 0.770 |
| 5 | 65.4 | 87.2 | 76.3** | 7.7 | −48.59 | 0.130 | 9.12 | 0.556 |
| 6 | 58.0 | 65.5 | 61.8** | 2.7 | −31.39 | 0.027 | 19.49 | 0.082 |

*, **Means are statistically different from untreated controls at 0.05 and 0.01 significance level, respectively.

TABLE 3

Effect of different doses of imazapyr on Phytotoxicity Index 14 days after for three sunflower genotypes carrying the A205V mutation event, thre genotypes carrying the A122T mutation event, two genotypes carrying the A205V/A122T mutation event and one susceptible line.

| | WT | A205V | | | | | A122T | | | | | A122T/A205V | | | | Difference between A205V vs | P- | ifference between A1222T vs | P- |
|---|---|---|---|---|---|---|---|---|---|---|---|---|---|---|---|---|---|---|---|
| Dose | L5 | H1 | L1 | L2 | Mean | SD | H2 | L3 | L4 | Mean | SD | H3 | H4 | Mean | SD | A205V/A122T | value | A205V/A122T | value |
| 0 | 0 | 0 | 0 | 0 | 0 | 0 | 0 | 0 | 0 | 0 | 0 | 0.0 | 0.0 | 0.0 | 0.0 | 0.00 | — | 0.00 | — |
| 0.5 | 9 | 0 | 0 | 0 | 0 | 0 | 0.5 | 0.4 | 0.0 | 0.3 | 0.3 | 0.5 | 0.0 | 0.5 | 0.0 | −0.50 | ns | −0.21 | 0.300 |
| 1 | 9 | 0 | 0 | 0 | 0 | 0 | 0.5 | 0.4 | 0.0 | 0.3 | 0.3 | 0.5 | 0.0 | 0.5 | 0.0 | −0.50 | ns | −0.21 | 0.286 |
| 2 | 9 | 1.8 | 1.6 | 3.1 | 2.2* | 0.8 | 0.5 | 0.4 | 0.0 | 0.3 | 0.3 | 0.5 | 0.0 | 0.5 | 0.0 | 1.66 | 0.075 | −0.20 | 0.311 |
| 3 | 9 | 6.4 | 5.1 | 3.9 | 5.1** | 1.2 | 0.5 | 0.5 | 0.0 | 0.3 | 0.3 | 0.5 | 0.0 | 0.5 | 0.0 | 4.65 | 0.022 | −0.17 | 0.423 |
| 4 | 9 | 8.0 | 8.4 | 5.9 | 7.4** | 1.3 | 0.5 | 1.0 | 0.0 | 0.5 | 0.5 | 0.5 | 0.0 | 0.5 | 0.0 | 6.92 | 0.012 | 0.00 | 1.000 |
| 5 | 9 | 8.9 | 8.9 | 6.9 | 8.2** | 1.1 | 0.5 | 2.0 | 0.0 | 0.8 | 1.0 | 0.6 | 0.2 | 0.6 | 0.2 | 7.59 | 0.006 | 0.21 | 0.764 |
| 6 | 9 | 9.0 | 8.9 | 6.7 | 8.2** | 1.3 | 0.5 | 2.5 | 0.5 | 1.2 | 1.2 | 1.0 | 0.0 | 1.0 | 0.0 | 7.19 | 0.010 | 0.17 | 0.826 |

*, **Means are statistically different from untreated controls at 0.05 and 0.01 significance level, respectively.

TABLE 4

Effect of different doses of imazapyr on biomass accumulation 14 days after treatment for three sunflower genotypes carrying the A205V mutation event, three genotypes carrying the A122T mutation event, two genotypes carrying the A205V/A122T mutation event and one susceptible line

| | WT | A205V | | | | | A122T | | | | |
|---|---|---|---|---|---|---|---|---|---|---|---|
| Dose | L5 | H1 | L1 | L2 | Mean | SD | H2 | L3 | L4 | Mean | SD |
| 0 | 100.0 | 100 | 100 | 100 | 100 | 0.0 | 100 | 100 | 100 | 100 | 0 |
| 0.5 | 18.3 | 95.0 | 91.7 | 99.2 | 95.3* | 3.7 | 100 | 96.6 | 100.0 | 98.9 | 2.0 |
| 1 | 15.0 | 89.6 | 81.7 | 85.0 | 85.5** | 4.0 | 97.2 | 93.9 | 99.1 | 96.7* | 2.6 |
| 2 | 15.0 | 75.5 | 54.7 | 58.1 | 62.8** | 11.2 | 97.9 | 81.6 | 97.0 | 92.2** | 9.2 |
| 3 | 15.0 | 60.4 | 35.7 | 48.1 | 48.1** | 12.4 | 98.2 | 75.8 | 96.1 | 90.0** | 12.4 |
| 4 | 15.0 | 46.5 | 25.3 | 28.8 | 33.5** | 11.3 | 97.8 | 75.0 | 84.3 | 85.7** | 11.5 |
| 5 | 15.0 | 38.9 | 19.8 | 27.4 | 28.7** | 9.6 | 85.1 | 60.1 | 77.5 | 74.3** | 12.8 |
| 6 | 15.0 | 33.9 | 19.5 | 24.9 | 26.1** | 7.2 | 79.5 | 59.6 | 70.7 | 69.9** | 10.0 |

| | A122T/A205V | | | | Difference between A205V vs | P- | ifference between A1222T vs | P- |
|---|---|---|---|---|---|---|---|---|
| Dose | H3 | H4 | Mean | SD | A205V/A122T | value | A205V/A122T | value |
| 0 | 100 | 100 | 100.0 | 0.0 | 0.00 | — | 0.00 | — |
| 0.5 | 99.804 | 99.479 | 99.6 | 0.2 | −4.33 | 0.271 | −0.76 | 0.579 |
| 1 | 100.0 | 97.8 | 98.9 | 1.6 | −13.45 | 0.241 | −2.17 | 0.333 |
| 2 | 94.3 | 92.2 | 93.2** | 1.5 | −30.47 | 0.063 | −1.07 | 0.860 |
| 3 | 90.8 | 88.2 | 89.5** | 1.9 | −41.42 | 0.049 | 0.55 | 0.947 |
| 4 | 87.8 | 85.0 | 86.4** | 2.0 | −52.87 | 0.029 | −0.73 | 0.923 |
| 5 | 72.1 | 78.7 | 75.4** | 4.7 | −46.69 | 0.013 | −1.14 | 0.898 |
| 6 | 63.2 | 71.8 | 67.5** | 6.0 | −41.41 | 0.012 | 2.41 | 0.759 |

*, **Means are statistically different from untreated controls at 0.05 and 0.01 significance level, respectively.

Example 3: Herbicide Tolerance of Lines Homozygous and Heterozygous for A122T and A205V Versus Lines Heterozygous for Both Mutations (A122T/A205V) Under Field Conditions This experiment was conducted to compare the herbicide tolerance of sunflower hybrids and lines in different genotypes carrying the A122T and A205V mutations in homozygous (A122T/A122T or A205V/A205V), heterozygous (A122T/– or A205V/–) and double stacked heterozygous (A122T/A205V) states under field conditions.

Materials

The sunflower materials that were used are listed in Table 5.

TABLE 5

| Entry list | | | | | |
|---|---|---|---|---|---|
| Type of Material | Mut event | Zygosity | Product | Entry Description | Entry Number |
| WT × IMI restorer | A205V | hetero | hybrid | 1-hybrid | 1 |
| WT × IMI restorer | A205V | hetero | hybrid | 3-hybrid | 2 |

TABLE 5-continued

Entry list

| Type of Material | Mut event | Zygosity | Product | Entry Description | Entry Number |
|---|---|---|---|---|---|
| WT-CMS × IMI restorer | A205V | hetero | hybrid | 7-hybrid | 3 |
| IMI Restorer | A205V | homo | restorer | 4-line | 4 |
| IMI CMS × IMI restorer | A205V | homo | hybrid | 6-hybrid | 5 |
| WT × GM40 restorer | A122T | hetero | hybrid | 8-hybrid | 6 |
| WT × GM40 restorer | A122T | hetero | hybrid | 15-hybrid | 7 |
| WT × GM40 restorer | A122T | hetero | hybrid | 16-hybrid | 8 |
| GM40 restorer | A122T | homo | restorer | 9-line | 9 |
| GM40 CMS × GM40 restorer | A122T | homo | hybrid | 13-hybrid | 10 |
| GM40 CMS × GM40 restorer | A122T | homo | hybrid | 14-hybrid | 11 |
| IMI CMS × GM40 restorer | A205V/A122T | hetero/double | hybrid | 10-hybrid | 12 |
| GM40 CMS × IMI restorer | A205V/A122T | hetero/double | hybrid | 11-hybrid | 13 |
| IMI CMS × GM40 restorer | A205V/A122T | hetero/double | hybrid | 12-hybrid | 14 |
| WT | — | — | B line | 5-WT | 15 |

Methods

Seed from each entry in Table 5 were produced under optimum seed production conditions in South America during the 2005-2006 growing season. The field trial was conducted at one location in North Dakota, USA in 2006. The entries were organized in a randomized complete block using a split plot design consisting of 3 replications for each treatment combination. Factor A (Table 6) was the herbicide treatment, and factor B was the sunflower entry. The plot size was 4 rows×12 ft and the seeding rate was consistent with local agronomic practices.

TABLE 6

Factor A - Herbicide Treatment List

| Treatment No. | Treatment |
|---|---|
| 1 | Untreated |
| 2 | 50 g ai/ha imazamox + 0.25% (v/v) NIS |
| 3 | 100 g ai/ha imazamox + 0.25% (v/v) NIS |
| 4 | 200 g ai/ha imazamox + 0.25% (v/v) NIS |
| 5 | 160 g ai/ha imazapyr + 0.25% (v/v) NIS |

NIS = non-ionic surfactant
Spray volume: 10 gallons per acre (GPA) (or 100 liters/ha) for backpack sprayer or 20 GPA (or 200 liters/ha) for tractor mounted boom
Growth Stage at Herbicide Application: 2-4 leaves Entry 15 (WT Maintainer line) was left unsprayed in all treatment blocks.

Phytotoxicity ratings were assessed at 7 and 21 days following herbicide application. Phytotoxicity was recorded as the amount of plant damage (in percent), where a rating of '0' indicated no damage to the plants in the plot relative to the untreated plot. A rating of '100' indicated complete necrosis (death) of the plants in the plot relative to the untreated plot.

The data was subjected to an ANOVA analysis and the means from the 3 repetitions are presented in Table 7 (phytotoxicity at 7 days post-treatment) and Table 8 (phytotoxicity at 21 days post-treatment).

Results

At 160 g ai/ha of imazapyr there were no significant differences in phytotoxicity between the A205V/A122T double heterozygous entries and the homozygous A205V and A122T entries both at 7 days and 21 days after treatment (DAT). The phytotoxicity in the heterozygous A205V entries was significantly higher than the double heterozygous A205V/A122T and the homozygous entries for both the 7 and 21 DAT ratings (in the range of 20-43% for the heterozygous A205V entries for 21 DAT). The phytotoxicity in the heterozygous entries also increased from the time the 7 DAT evaluation was taken to the time the 21 DAT was taken. There was no significant increase in phytotoxicity from 7 DAT to 21 DAT for the A205V/A122T double heterozygous and A122T/A122T and A205V/A205V homozygous entries.

Three levels of imazamox, 50 g ai, 100 g ai and 200 g ai/ha, were tested on all entries (except entry 15). At 200 g ai/ha of imazamox, the heterozygous A205V/A122T lines (2-3% phytotoxicity at 21 DAT) demonstrated significantly less phytotoxicity than the homozygous A205V/A205V lines (15-22% phytotoxicity at 21 DAT) and equivalent phytotoxicity to the homozygous A122T/A122T lines (3-5% phytotoxicity at 21 DAT).

Discussion

The double heterozygous A205V/A122T entries demonstrated equivalent herbicide tolerance to the homozygous A122T/A122T entries and superior herbicide tolerance to the homozygous A205V/A205V entries, as demonstrated by the highest imazamox treatment level (200 g ai/ha).

The single treatment level of imazapyr, 160 g ai/ha, was not high enough to show significant differences in phytotoxicity between the double heterozygous A205V/A122T entries and the homozygous entries, yet it was sufficient to illustrate the higher tolerance obtained by stacking the two heterozygous A205V/A122T mutations together versus each heterozygous mutation on its own.

Based on the imazamox treatment data, the A122T mutation when stacked with the A205V mutation in the heterozygous state, provides stronger herbicide tolerance than the A205V mutation in the homozygous state.

The experiment described above disclose the interactions between two allele mutants of AHASL1 in sunflower. The mutation in codon 122 has significantly greater herbicide tolerance than any previously reported AHAS mutations in sunflower, whereas the mutation in codon 205 confers intermediate levels of resistance. As the allele 122 shows dominance over its allele 205, heterozygote genotypes carrying both mutants have the same level of tolerance as the homozygous 122.

Due to the increased herbicide tolerance, the present invention provides methods that allow for the development of new and highly efficacious herbicide products for sunflower production. Since the present invention provides sunflower plants with commercial levels of herbicide tolerance produced by making a single gene substitution in the present day Clearfield sunflower hybrids, which are A205V/A205V, the present invention finds use in increasing the breeding efficiency for the production of herbicide tolerant sunflower hybrids and also provides for a more rapid deployment of the A122T mutation in commercial sunflower hybrids.

TABLE 7

Phytotoxicity Ratings (% Crop Injury) recorded 7 Days after Treatment (DAT)

| Type of Material | Mut event | Zygosity | Product | Entry Description | 7 DAT 50 G IMAZAMOX | 7 DAT 100 G IMAZAMOX | 7 DAT 200 G IMAZAMOX | 7 DAT 160 G IMAZAPYR | 7 DAT UNTREATED |
|---|---|---|---|---|---|---|---|---|---|
| WT × IMI restorer | A205 | hetero | hybrid | 1-hybrid | 8.3 | 35.0 | 48.3 | 16.7 | 0.0 |
| WT × IMI restorer | A205 | hetero | hybrid | 3-hybrid | 11.7 | 46.7 | 60.0 | 35.0 | 0.0 |
| WT-CMS × IMI restorer | A205 | hetero | hybrid | 7-hybrid | 13.3 | 43.3 | 56.7 | 21.7 | 0.0 |
| IMI Restorer | A205 | homo | restorer | 4-line | 6.7 | 6.7 | 18.3 | 11.7 | 0.0 |
| IMI CMS × IMI restorer | A205 | homo | hybrid | 6-hybrid | 5.0 | 8.3 | 26.7 | 8.3 | 0.0 |
| WT × GM40 restorer | A122 | hetero | hybrid | 8-hybrid | 13.3 | 13.3 | 25.0 | 13.3 | 0.0 |
| WT × GM40 restorer | A122 | hetero | hybrid | 15-hybrid | 10.0 | 11.7 | 16.7 | 8.3 | 0.0 |
| WT × GM40 restorer | A122 | hetero | hybrid | 16-hybrid | 10.0 | 15.0 | 23.3 | 10.0 | 0.0 |
| GM40 restorer | A122 | homo | restorer | 9-line | 1.7 | 5.0 | 10.0 | 8.3 | 0.0 |
| GM40 CMS × GM40 restorer | A122 | homo | hybrid | 13-hybrid | 3.3 | 5.0 | 10.0 | 5.0 | 0.0 |
| GM40 CMS × GM40 restorer | A122 | homo | hybrid | 14-hybrid | 5.0 | 6.7 | 11.7 | 8.3 | 0.0 |
| IMI CMS × GM40 restorer | A205/ A122 | hetero/ double | hybrid | 10-hybrid | 3.3 | 3.3 | 10.0 | 3.3 | 0.0 |
| GM40 CMS × IMI restorer | A205/ A122 | hetero/ double | hybrid | 11-hybrid | 0.0 | 3.3 | 11.7 | 3.3 | 0.0 |
| IMI CMS × GM40 restorer | A205/ A122 | hetero/ double | hybrid | 12-hybrid | 10.0 | 10.0 | 11.7 | 5.0 | 0.0 |
| WT | — | — | B line | 5-WT | 0.0 | 0.0 | 0.0 | 0.0 | 0.0 |

LSD = 9.64
St Dev = 6.03
CV = 54.70
Grand Mean = 11.02

TABLE 8

Phytotoxicity Ratings (% Crop Injury) recorded 21 Days after Treatment (DAT)

| Type of Material | Mut event | Zygosity | Product | Entry Description | 21 DAT 50 G IMAZAMOX | 21 DAT 100 G IMAZAMOX | 21 DAT 200 G IMAZAMOX | 21 DAT 160 G IMAZAPYR | 21 DAT UNTREATED |
|---|---|---|---|---|---|---|---|---|---|
| WT × IMI restorer | A205 | hetero | hybrid | 1-hybrid | 6.7 | 25.0 | 73.3 | 20.0 | 0.0 |
| WT × IMI restorer | A205 | hetero | hybrid | 3-hybrid | 11.7 | 46.7 | 76.7 | 43.3 | 0.0 |
| WT-CMS × IMI restorer | A205 | hetero | hybrid | 7-hybrid | 3.3 | 40.0 | 78.3 | 36.7 | 0.0 |
| IMI Restorer | A205 | homo | restorer | 4-line | 5.0 | 6.7 | 15.0 | 6.7 | 0.0 |
| IMI CMS × IMI restorer | A205 | homo | hybrid | 6-hybrid | 0.0 | 3.3 | 21.7 | 3.3 | 0.0 |
| WT × GM40 restorer | A122 | hetero | hybrid | 8-hybrid | 6.7 | 11.7 | 28.3 | 11.7 | 0.0 |
| WT × GM40 restorer | A122 | hetero | hybrid | 15-hybrid | 6.7 | 11.7 | 30.0 | 21.7 | 0.0 |
| WT × GM40 restorer | A122 | hetero | hybrid | 16-hybrid | 6.7 | 16.7 | 31.7 | 23.3 | 0.0 |
| GM40 restorer | A122 | homo | restorer | 9-line | 0.0 | 0.0 | 3.3 | 5.0 | 0.0 |
| GM40 CMS × GM40 restorer | A122 | homo | hybrid | 13-hybrid | 0.0 | 1.7 | 3.3 | 1.7 | 0.0 |
| GM40 CMS × GM40 restorer | A122 | homo | hybrid | 14-hybrid | 0.0 | 3.3 | 5.0 | 3.3 | 0.0 |
| IMI CMS × GM40 restorer | A205/ A122 | hetero/ double | hybrid | 10-hybrid | 0.0 | 0.0 | 1.7 | 0.0 | 0.0 |
| GM40 CMS × IMI restorer | A205/ A122 | hetero/ double | hybrid | 11-hybrid | 0.0 | 0.0 | 3.3 | 0.0 | 0.0 |
| IMI CMS × GM40 restorer | A205/ A122 | hetero/ double | hybrid | 12-hybrid | 3.3 | 3.3 | 3.3 | 1.7 | 0.0 |
| WT | — | — | B line | 5-WT | 0.0 | 0.0 | 0.0 | 0.0 | 0.0 |

LSD = 8.89
St Dev = 5.55
CV = 56.78
Grand Mean = 9.78

Example 4: Herbicide Tolerance of Homozygous A122T/A122T or A205V/A205V and Heterozygous A122T/A205V Events to Foliar Applications of Imazapyr at Late Vegetative or Early Reproductive Stages of Plant Development for the Control of Broomrape

*Orobanche cumana* and *Orobanche cernua* (broomrape) are two parasitic plants that infect sunflowers in many production areas of the world. Both species infect sunflower plants sequentially from V6 to the flowering (R5) stage. It has been proposed to use an imidazolinone herbicide, such as imazethapyr, to control broomrape by applying the herbicide to A205-containing sunflower plants at the V10 to R1 stage of development (WO 1999065312). Using this approach, *Orobanche* control was successful and phytotoxicity was negligible.

Here we demonstrate that the tolerance of A122T/A122T or A122T/A205V hybrids is better than the tolerance of A205V homozygous plants when an imidazolinone herbicide, such as imazapyr, is applied at a 2× application rate during the early reproductive stages of development (R1). In this report, we demonstrate the usefulness of A122T/A122T and A122T/A205V for *Orobanche* control in sunflowers.

Materials

The lines H1, H2 and H3 are as described in Table 9. The hybrid H5 is an F1 originating from a cross between L3×R701, and the hybrid H6 is an F1 originating from a cross between L1×R701.

Methods

Seeds from each entry were produced under optimum seed production conditions in Laguna Blanca (Formosa, Argentina) in 2005. The field trial was conducted at one location in Venado Tuerto (Santa Fe, Argentina) in 2006. The entries were organized in a randomized complete block design consisting of 3 replications for each treatment combination. Factor A was the ontogenetic stage of sunflower development (V8 and R1) and factor B was the sunflower entry. The plot size was 5 rows×6 meters, with plants distributed every 25 cm within each row. At the V8 or R1 stage, 160 g ai/ha imazapyr+0.25% (v/v) NIS was applied with a spray volume of 100 liters/ha using a backpack sprayer.

Phytotoxicity ratings were assessed at 14 days and 21 days after herbicide application. Phytotoxicity was recorded as the amount of plant damage, where a rating of "0" indicated no damage to the plants in the plot relative to the untreated control plots. A rating of 1 to 15 indicated an increasing level of chlorosis in the plot, where "15" indicated a generalized yellowish of the plot. Ratings of "20" to "49" indicated an increasing level of stunting, deformations and necrosis. A rating of "50", indicated death (complete necrosis) of the plants.

The data were subjected to an ANOVA analysis. Means of each entry were compared using the LSD test at the 0.01 probability level.

Results

The mean Phytotoxicity Index (PI) scored at 14 and 21 days after treatment (DAT) is presented in Tables 9 and 10.

Nearly all of the hybrids showed slight symptoms of chlorosis when sprayed at the V8 stage of plant development. The only exception was the heterozygous 122/WT hybrid which demonstrated a complete yellowing at 14 DAT (Table 9). This yellowing disappeared at 21 DAT (Table 10). Also, at 21 DAT, there were no differences between the lines with respect to PI (Table 10).

On the other hand, when the hybrids were sprayed at the R1 stage of plant development and assessed at 14 DAT, two well defined groups of materials were recognized. One group only showed chlorosis symptoms (PI less than 11.7) while the second group showed chlorosis symptoms along with stunting and deformation (PI greater than 35). The first group was composed of lines carrying at least one allele A122T (i.e.: hybrids A122T/A122T, A122T/A205V and A122/WT), and the second group consisted of hybrids carrying the A205V mutation event in both the homozygous and heterozygous state (A205V/A205V, A205V/WT). Differences in PI between both groups were highly significant ($p<0.01$; Table 9). At 21 DAT, however, the A122/WT hybrid increased its PI score (from 11.7 to 23.3), while, the A122T/A122T and A122T/A205V hybrids decreased their PI scores from 2.3-4.3 to 1.7-0.7. Differences between these last two hybrids and the A122T/WT hybrid were highly significant at 21 DAT (Table 10). The lines containing A205/A205V and A205V/WT also showed very high PI scores with many plants showing symptoms of apex burn and damage to the growing points (Table 10).

Conclusion

The results indicate that the hybrids A205V/A205V or A205V/WT cannot be sprayed with imazapyr after V8 because they showed increased phytotoxicity and severe damage after application. The hybrids A122T/A122T and A122T/A205V showed only slight symptoms of chlorosis after imazapyr application. This confirmed that the A122T/A122T and A122T/A205V sunflower plants demonstrated a better level of tolerance to imidazolinone herbicides when applied at the R1 stage, than the A205V/A205V or A205V/WT material. In summary, lines containing the A122T/A122T and A122T/A205V stack can be used to control *Orobanche* with imazapyr by applying the herbicide at the R1 (late vegetative or early reproductive) stage of plant development.

TABLE 9

Mean Phytotoxicity Index scored at 14 days after treatment (DAT) with Imazapyr (160 gr ai/ha) applied at two different stages of plant development (V8 and R1) for the mutation events A122T and A205V and heterozygous genotypes A122/A205, A122/WT and A205/WT. Different letters indicate significant differences at $p < 0.01$.

Evaluation at 14 DAT

| Genotype | AHASL1 allele/s | Without Treatment | V8 | | R1 | |
|---|---|---|---|---|---|---|
| H2 (L3 * L4) | 122/122 | 0 | 5 | ab | 2.3 | a |
| H1 (L1 * L2) | 205/205 | 0 | 6 | ab | 35 | b |
| H3 (L3 * L2) | 122/205 | 0 | 3 | a | 4.3 | a |
| H5 (L3 × WT) | 122/Wild type | 0 | 15 | b | 11.7 | a |
| H6 (L1 * WT) | 205/wild type | 0 | 5 | ab | 40 | b |

LSD-value ($p < 0.01$) = 10.04

Residual Mean Square = 20.0

Genotype Mean Square = 476.22 ($p < 2.2e^{-16}$)

TABLE 10

Mean Phytotoxicity Index scored at 21 days after treatment (DAT) with Imazapyr (160 g ai/ha) applied at two different stages of plant development (V8 and R1) for the mutation events A122T and A205V and heterozygous genotypes A122/A205, A122/WT and A205/WT. Different letters indicate significant differences at p < 0.01.
Evaluation at 21 DAT

| Genotype | AHASL1 allele/s | without treatment | V8 | | R1 | |
|---|---|---|---|---|---|---|
| H2 (L3 * L4) | 122/122 | 0 | 1 | a | 1.7 | a |
| H1 (L1 * L2) | 205/205 | 0 | 3 | a | 37.7 | bc |
| H3 (L3 * L2) | 122/205 | 0 | 0 | a | 0.7 | a |
| H5 (L3 × WT) | 122/Wild type | 0 | 5 | a | 23.3 | b |
| H6 (L1 * WT) | 205/wild type | 0 | 5 | a | 48.3 | C |

LSD-value (p < 0.01) = 16.39
Residual Mean Square = 53.3
Genotype Mean Square = 806.33 (p < $2.2e^{-16}$)

Example 5: Response of Homozygous A122T/A122T or P197L/P197L and Heterozygous A122T/P197L Events to a Sulphonylurea Herbicide at the Whole Plant Level Resistance to sulphonylureas in sunflower was discovered in wild *Helianthus* populations from Kansas (USA, (Al-Khatib et al. (1998) *Weed Sci.* 46:403-407). The gene for resistance (Ar-kan) has been introgressed from a wild population into elite inbred lines for the purpose of developing and deploying herbicide resistant cultivars and hybrids (Al-Khatib and Miller (2000) *Crop Sci.* 40:869; Miller and Al-Khatib (2002) 42:988-989; Miller and Al-Khatib (2004) *Crop Sci.* 44:1037-1038). It has been demonstrated that AHASL1 from sulphonylurea resistant genotypes harbors a C-to-T mutation in codon 197 that leads to a change from Pro to Leu at this position (Kolkman et al. (2004) *Theor. Appl. Genet.* 109: 1147-1159).

Metsulfuron methyl (Methyl 2 E[C[(4-Methoxy-6-methyl-1,3,5-Triazifl-2-yl)aminolcarbonyl]amino]sulfonyl.] benzoate]) is a sulfonylurea herbicide registered for use on wheat and barley and on non-cropland sites such as right of way (EPA Pesticide Fact Sheet Metsulfuron methyl (1986) Collection of pesticide chemistry, US Government Printing Office 461-221/24041).

The objective of this study was to quantify and contrast the metsulfuron sensitivity of sunflower hybrids carrying the A122T and P197L mutations in homozygous (A122T/A122T or P197L/P197L) and heterozygous (A122T/P197L) states at the whole plant level under greenhouse conditions.

Materials

The following materials were used: B770, GM1606, GM40, L4, cms GM40×L4, cms GM40×BTSu-R1 and BTSu-R1. B770 is a susceptible sunflower line that was used as the parental source for the mutagenesis line GM1606. GM1606 is homozygous for the A122T mutation, and GM1606 and B770 are isolines which only differ at the AHASL1 locus. GM40, L4, and cmsGM40×L4 were described above. BTSu-R1 is a restorer line developed in our lab and obtained by pedigree selection from the composite population SURES-2, that was released by Miller and Al-Khatib (2004) *Crop Sci.* 44:1037-1038.

Methods

Seeds were sown in Petri dishes and, after germination, plantlets were transplanted into 10 cm pots containing potting media consisting of equal parts of vermiculite, soil, and sand. Plants were grown in the greenhouse under natural light conditions supplemented with 400 W sodium halide lamps to provide a 16 hr daylength. Day/night temperatures were 25 and 20° C., respectively. At the V2-V4 stage (Schneiter & Miller, 1981) 20 plants of each genotype were randomly assigned to each treatment consisting of three metsulfuron methyl doses (0 or no treatment, 5 g ai/ha or a 1× rate, and 10 g ai/ha or a 2× rate). A zero-time biomass determination was also conducted. The experiment was arranged as a randomized complete block design (RCBD) with a full factorial arrangement of treatments and 20 replications (sunflower line×treatment).

For the zero-time dried weight determination, ten plants of each genotype were cut at the cotyledonal node on the day of herbicide application and dried at 60° C. for 48 hr. The rest of the plants were maintained for 14 days after herbicide treatment (DAT) and their height, Phytotoxicity Index (PI) and above ground dry biomass were recorded. Height was determined as the distance between the cotyledonal node and the apex of each plant. The above ground biomass data for each line was converted to biomass accumulation after application by subtracting the appropriate average zero-time biomass from each sample. Height and dry biomass were converted to a percentage of the untreated control for each line to allow direct comparisons between groups. PI is a phenotypic scale from 0 to 9 that assesses phytotoxicity for each plant by visual inspection. Plants without any symptoms were recorded as "0". Increasing levels of stunting and chlorosis, with respect to the untreated control plants, were recorded in the range of "1 to 4". Increasing levels of leaf abnormalities and leaf necrosis were recorded in the range of"5 to 8". Dead plants with total necrosis of the apex were recorded as a "9".

The data was subjected to an ANOVA and the means were compared by an LSD test.

Results

Height, dry matter accumulation, and PI of the wild type and A122/A122T homozygous plants reflected the great sensitivity of conventional sunflower and the mutant event A122T to sulphonylureas at both application rates (Table 11). In contrast, the mutation event P197L presented a greater level of tolerance, with nearly 80% of the height of the untreated controls at both herbicide rates. Likewise, dry matter accumulation for this event was 88% and 77% at 1× and 2× metsulfuron rates, respectively. Finally, PI of the P197L/P197L homozygous line was 0 and 0.1 at both herbicide rates, reflecting that plants had virtually no phytotoxic symptoms (Table 11).

The stacked hybrid A122T/P197L showed the same pattern of tolerance as the homozygous P197 line and presented a better performance than all of the homozygous A122T materials for all variables analyzed (Table 11). To illustrate this, the A122T/P197L line, when treated with 1× metsulfuron, showed the same PI and height reduction as the homozygous P197L resistant line. At the 2× metsulfuron rate, A122T/P197L demonstrated the same accumulation of dry matter as the P197L homozygous line. The heterozygous P197L/A122T hybrid differed significantly from the resistant line P197L for the following parameters: DMA at 1× (74.4 vs 88.1, respectively), PH (62 vs 80.9%), and PI at 2× (1 vs 0.1). However, the magnitude of these differences was very low when compared to the differences observed between the A122T/P197L heterozygous material and all of the homozygous A122T and wild type lines.

Conclusion

Based on these results, the double heterozygous A122T/P197L demonstrated superior metsulfuron resistance than the homozygous A122T/A122T and wild type materials, and almost the same level of tolerance as the P197L/P197L homozygous line.

TABLE 11

Mean Height Reduction (PH), Dry Matter accumulation (DMA) and
Phytotoxicity Index (PI) of homozygous A122T/A122T, P197L/P197L,
heterozygous P197L/A122T and wild type materials after foliar
application of two rates of metsulfuron.

|  |  | Metsulfuron rate | | | | | |
|---|---|---|---|---|---|---|---|
|  | AHAS | 1X (5 g ai./ha) | | | 2X (10 g ai./ha) | | |
| Genetic material | Genotype | PH | DMA | PI | PH | DMA | PI |
| B770 | WT | 21.73$^{a*}$ | 28.43$^b$ | 8.50$^{bc}$ | 18.20$^a$ | 28.77$^b$ | 9.00$^d$ |
| GM1606 | A122T/A122T | 21.55$^a$ | 30.39$^b$ | 8.70$^d$ | 21.70$^a$ | 20.45$^a$ | 9.00$^d$ |
| GM40 | A122T/A122T | 21.39$^a$ | 25.73$^{ab}$ | 9.00$^d$ | 21.17$^a$ | 20.69$^a$ | 9.00$^d$ |
| L4 | A122T/A122T | 19.47$^a$ | 25.40$^{ab}$ | 8.25$^b$ | 18.73$^a$ | 18.80$^a$ | 8.5$^c$ |
| cmsGM40xL4 | A122T/A122T | 22.45$^a$ | 19.90$^a$ | 8.67$^d$ | 20.56$^a$ | 18.23$^a$ | 8.82$^{cd}$ |
| cmsGM40xBTSu-R1 | A122T/P197L | 77.04$^b$ | 74.36$^c$ | 0.00$^c$ | 61.99$^b$ | 72.66$^c$ | 1.00$^b$ |
| BTSu-R1 | P197L/P197L | 79.01$^b$ | 88.10$^d$ | 0.00$^c$ | 80.85$^c$ | 76.69$^c$ | 0.10$^b$ |
| LSD-value (p < 0.01) |  | 4.87 | 8.29 | 0.33 | 5.45 | 6.97 | 0.38 |
| Residual MS |  | 20.00 | 58.00 | 0.09 | 25.00 | 41.00 | 0.12 |
| Genotype MS |  | 754.3*** | 257.90*** | 3908.9*** | 528.28*** | 339.05*** | 2680*** |

*Different letters indicate significant differences at p < 0.01 probability level.

Example 6: Diagnostic PCR Markers for the Herbicide-Resistance Alleles of the AHASL1 Locus in Sunflower A single nucleotide polymorphism (SNP) assay is provided for high-throughput genotyping of sunflower plants carrying the AHASL1 sunflower mutation described herein above and in U.S. Provisional Patent Application No. 60/695,952, filed Jul. 1, 2005). The assay permits (1) the detection of individuals carrying the A122T mutation, (2) the determination of zygosity of the A122T mutation in these individuals, and (3) in the case of heterozygosis, the detection of both the A122T mutation along with other stacked AHAS resistant allele(s) (A205V or P197L) which are present in the plant.

1) PCR Primers and Amplification Conditions

PCR primers were developed based on the DNA sequences disclosed herein and in the abovementioned patent application. The name and sequences of these primers are as follows:

```
Forward conserved primer
p-AHAS NIDF
                                   (SEQ ID NO: 3)
5'-TGT TCT CTC CGA CTC TAA A-3'

Reverse "Wild Type" primer
AHAS 122 TWT
                                   (SEQ ID NO: 4)
5'-TGG TGG ATC TCC ATT GAG TC-3'

Reverse "Mutant" primer
AHAS 122 TMU
                                   (SEQ ID NO: 5)
5'-TGG TGG ATC TCC ATT GAG TT-3'
```

The reaction mix was as follows: 1 U Taq DNA Polymerase (Biotools, 10.047), 70 ng genomic sunflower DNA, 25 micrograms BSA, and have a final concentration of 100 µM of each dNTP, 0.25 µM of each primer p-AHAS NIDF/AHAS122TWT or p-AHAS NIDF/AHAS 122 TMU, 90 mM Tris-HCl pH8, 20 mM $(NH4)_2SO4$ and 2.5 mM $MgCl_2$.

The PCR program consists in an initial denaturation step of 94° C. for 2 min, followed by 45 cycles of 30 sec at 94° C., 30 sec at 55° C. and 30 sec at 72° C., followed by a final elongation step at 72° C. for 10 min.

2) Detecting Plants Carrying the A122T Mutation and their Zygosity

In order to detect the individuals that carry the described mutation, p-AHAS NIDF/AHAS 122 TMU primer combination were used. Individuals having at least one copy (i.e., homo and heterozygote individuals) of the A122T allele yield a fragment of 195 bp. Wild-type individuals, or individuals having any other haplotypes for AHASL1 yield no fragment with this primer combination (see FIG. 6, and Table 12). In conclusion, this primer combination is diagnostic for the A122T mutation.

The primer combination p-AHAS NIDF/AHAS 122 TWT was used (a) to confirm the specificity of the previous result, because the A122T allele should not produce an amplification product with this primer combination, and (b) to determine which is the other allele present in each plant (if different from A122T) (see FIG. 7, and Table 12).

When the primer combination p-AHAS NIDF/AHAS 122 TWT was used, wild-type individuals, A205V and P197L mutants yielded a specific fragment (Table 12); whereas A122T homozygotes yielded no amplification product.

The products amplified in 1) are resolved in a 4% agarose gel (Methaphor Agarose).

The expected size of PCR products from various sunflower haplotypes (Hap) at the AHAHL1 gene are provided in Table 12. An alignment of the sequences of Hap1-Hap6 is provided in FIG. 8 and includes the location of annealing sites of the p-AHAS NIDF, AHAS122TWT, and AHAS 122 TMU primers described above as well as the site of the A122T mutation and the $(ACC)_n$ region, which gives rise to the size differences of the PCR products among the various haplotypes.

TABLE 12

Expected sizes of amplification products obtained
with the pair of primers p-AHAS NIDF/AHAS122TWT
and p-AHAS NIDF/AHAS 122 TMU.

| Haplotype[1,2] |  | Obtained Fragments p-AHAS NIDF/ AHAS122TWT | Obtained Fragments p-AHAS NIDF/ AHAS 122 TMU |
|---|---|---|---|
| Homozygotes |  |  |  |
| Hap 6 (A122T) | CLHaPlus | null | 195 bp |
| Hap 1 | Cultivated lines | 195 bp | Null |

TABLE 12-continued

Expected sizes of amplification products obtained
with the pair of primers p-AHAS NIDF/AHAS122TWT
and p-AHAS NIDF/AHAS 122 TMU.

| Haplotype[1,2] | | Obtained Fragments p-AHAS NIDF/ AHAS122TWT | Obtained Fragments p-AHAS NIDF/ AHAS 122 TMU |
|---|---|---|---|
| Hap 2 | Cultivated lines | 192 bp | Null |
| Hap 4 | Cultivated lines | 186 bp | Null |
| Hap 5 (A205V) | IMISUN derived lines | 186 bp | Null |
| Hap 3 (P197L) | SURES derived lines | 204 bp | Null |
| Heterozygotes | | | |
| Hap6/Hap1 | | 195 bp | 195 bp |
| Hap6/Hap2 | | 192 bp | 195 bp |
| Hap6/Hap4 | | 186 bp | 195 bp |
| Hap6/Hap 5 | | 186 bp | 195 bp |
| Hap6/Hap 3 | | 204 bp | 195 bp |
| Hap3/Hap1 | | 204/195 bp | Null |
| Hap3/Hap2 | | 204/192 bp | Null |
| Hap3/Hap5 | | 204/186 bp | Null |
| Hap3/Hap4 | | 204/186 bp | Null |
| Hap5/Hap1 | | 186/195 bp | Null |
| Hap5/Hap2 | | 186/192 bp | Null |
| Hap5/Hap4 | | 186/186 bp | Null |

[1]Haplotypes (Hap) 1 to 5 correspond to those provided in Kolkman et al. (2004) Theor. Appl. Genet. 109: 1147-1159).
[2]Type of AHASL1 mutation, if any, noted in parenthesis.

Example 7: Allele Specific Polymerase Chain Reaction for Detection of Sunflower AHASL1 A122T Allele In order to facilitate the breeding of CLEARFIELD sunflower, the following SNP assay for the detection of the sunflower AHASL1 A122T allele was developed. The IMI-tolerant varieties used for assay development and validation include numerous conventional and herbicide-tolerant varieties. This assay uses allele-specific polymerase chain reaction (PCR) to detect and determine the zygosity of the sunflower AHASL1 A122T allele. A single round of amplification with four primers provides the products necessary to detect the three possible states of zygosity: wild-type, heterozygous, and mutant (A122T/A122T). Because AHASL1 and AHASL2 loci are identical in the region containing the mutation, a set of primers were designed to specifically amplify the AHASL1 locus (see below HA122CF and HA122CR). In addition, allele-specific primers were designed to anneal/extend specifically from the single nucleotide "G" to "A" responsible for the respective codon change from alanine to threonine. The wild-type allele specific primer is a reverse primer. Thus, the terminal base is "C" as depicted below. A 794 base pair control band formed by HA122CF and HA122CR, is produced regardless of base(s) at the mutation site and serves as a positive control (FIG. 9).

The diagnostic band for the wild-type condition, formed by the amplification of primers HA122CF and HA122 wt, yields a fragment of 258 base pairs (FIG. 9). This primer contains a deliberate mismatch 4 bases upstream of the actual mutation which serves to generate increased specificity for the wild-type samples. The diagnostic band for the mutant condition yields a fragment of 576 base pairs (FIG. 9). A 576 base pair product is formed from the amplification of HA122mut and HA122CR and indicates presence of the mutant allele. The mutant specific primer contains a deliberate mismatch 3 bases upstream of the actual mutation which serves to generate increased specificity for the mutant samples. Therefore, a sample that is heterozygous for the mutation will yield three bands upon visualization by agarose gel electrophoresis, the control band and both of the diagnostic bands. A homozygous sample will show two bands. The gel pattern is dependent upon the base call in codon 122. The PCR primers are provided below.

```
Common forward primer (HA122CF):
                                (SEQ ID NO: 15)
5'GTTTCGCATTACCCATCACT3'

Wild-type specific primer (HA122wt):
                                (SEQ ID NO: 16)
5'GGTGGATCTCCATTAACGC3'

Mutant specific primers (HA122mut):
                                (SEQ ID NO: 17)
5' GCCTACCCCGGCTGCA3'

Common reverse primer (HA122CR):
                                (SEQ ID NO: 18)
5' CAAAACCGGCCTCTTCGC3'
```

Example 8: High Oleic Imidazolinone Resistant Sunflower Lines Expressing the A122T Trait Sunflower plants were produced that express the AHASL1 A122T mutant allele (also know as the CLHA-plus trait), which confers high levels of resistance to imidazolinones herbicides on a sunflower plant, and that produce seeds comprising an extractable seed oil that comprises at least 85% oleic acid. These sunflower plants were obtained by conventional breeding methodologies, through crossing an IMI-resistant line derived from GM40 with a High Oleic (HO) line (VB141) and selecting for both traits in F2 and later generations of inbreeding using molecular markers. GM40 and another sunflower line comprising at least one copy of the AHASL1 A122T mutant allele, GM1606, are described above and in WO 2007005581. Seeds of GM40 and GM1606 have been deposited with the ATCC and assigned ATCC Patent Deposit Numbers PTA-6716 and PTA-7606, respectively.

Materials

Lines BTI-OL-M1511, BTI-OL-M1709 and BTI-OL-2201 are three experimental sunflower lines selected for their high oleic content and their tolerance to imidazolinones. VB141, HA445 and OB712 are high oleic lines, B770 and BTK112 are two conventional lines, and GM40 is a A122T conventional line.

Methods

Fatty acid composition of the seeds: all the plants were grown under field conditions in Laguna Blanca (Formosa, Argentina) following a Complete Randomized Block Design with 3 replications. Ten grams of seeds from each replication were used for the analysis. Fatty acid composition of each sample was determined by gas chromatography following standard procedures. Mean values across the 3 replications for each material are provided in Table 16.

Tolerance to imidazolinones: Seeds of the nine lines were sown in pots under greenhouse conditions. At least 20 plantlets of each line were sprayed at V4 stage (Schneiter & Miller, 1981) with Imazapyr at a dose of 160 gr/ha. Fourteen days after treatment each plant was scored phenotypically using a Phytotoxicity Index (PI). PI is a phenotypic scale from 0 to 9 that was assessed for each plant by visual inspection. Plants without any symptoms were recorded as "0", increasing levels of stunting and yellowing with respect to the untreated control plants were recorded as "1" to "4", increasing levels of leaf abnormalities and leaf necrosis were recorded from "5" to "8", dead plants with total necrosis of the apex were recorded as "9".

Results

High oleic lines showed a range of oleic acid content in the seeds from 85.79 to 88.97%, conventional materials, on the other hand, showed a much lesser content (range: 18.62 to 24.2%). Lines BTI-OL-M1511, BTI-OL-M1709 and BTI-OL-2201 showed a concentration of oleic acid in the seeds from 89.58 to 90.83, similar to that obtained for the HO lines (Table 16).

Lines HA445, VB141, OB712, B770 and BTK112 were killed by the herbicide treatment, whereas lines BTI-OL-M1511, BTI-OL-M1709 and BTI-OL-2201 showed a resistance level similar to that observed in the resistant line GM40 (Table 17).

In conclusion, lines BTI-OL-M1511, BTI-OL-M1709 and BTI-OL-2201 combine a high level of resistance to imidazolinones and a high level of oleic acid in their seeds.

Materials and Methods

A sunflower line, BTK47, specifically selected for lack of an E-factor (imr1 imr1/imr2 imr2) was subjected to EMS seed mutagenesis. An $M_{2:4}$ line which survived imazapyr field selection, was selected for subsequent crossing and enzyme activity studies. This line was named GM40.

Field Evaluation of the A122T Trait

The A122T mutant allele was introgressed into different maintainer, restorer and sterile inbred lines. Homozygous A122T inbreds were crossed with either wild-type (WT) inbreds (containing no herbicide tolerance mutation), homozygous A122T inbreds, or homozygous A205V inbreds to produce different F1 mutant allele zygosity combinations (Table 18). These entries, along with several regionally adapted CLEARFIELD® A205V commercial variety checks, were field tested for imidazolinone tolerance at numerous locations in North America, South America and Europe from 2005 to 2008 (Table 19).

TABLE 13

Fatty acid composition of seeds of 9 sunflower lines (each value is the mean of 3 replications).

| Oil Profile | Lines | | | | | | | | |
|---|---|---|---|---|---|---|---|---|---|
| | BTI-OL-M1511 | BTI-OL-M1709 | BTI-OL-2201 | VB141 | HA445 | OB712 | GM40 | B770 | BTK112 |
| Myristic Acid (C14:0) | 0.018 | 0.023 | 0.02 | 0.014 | 0.01 | 0.02 | 0.09 | 0.08 | 0.1 |
| Palmitic Acid (C16:0) | 3.58 | 3.77 | 4.75 | 3.55 | 3.49 | 3.7 | 6.47 | 6.04 | 6.73 |
| Stearic Acid (C18:0) | 1.13 | 1.68 | 0.18 | 1.82 | 3.2 | 1.85 | 4.71 | 4.71 | 4.48 |
| Oleic Acid (C18:1) | 90.83 | 89.58 | 89.81 | 88.97 | 85.79 | 87.58 | 21.24 | 24.2 | 18.62 |
| Linoleic Acid (C18:2) | 2.86 | 3.07 | 3.65 | 3.91 | 5.63 | 5.15 | 65.85 | 63.41 | 68.25 |
| Linolenic Acid (C18:3) | 0.16 | 0.16 | 0.16 | 0.16 | 0.15 | 0.21 | 0.16 | 0.16 | 0.16 |
| Arachidic Acid (C20:0) | 0.09 | 0.14 | 0.09 | 0.2 | 0.21 | 0.17 | 0.21 | 0.26 | 0.23 |
| Gadoleic Acid (C20:1) | 0.24 | 0.31 | 0.33 | 0.26 | 0.17 | 0.24 | 0.04 | 0.1 | 0.07 |
| Behenic Acid (C22:0) | 0.76 | 0.88 | 0.72 | 0.78 | 1.13 | 0.82 | 0.96 | 0.85 | 0.9 |
| Lignoceric Acid (C24:0) | 0.24 | 0.3 | 0.28 | 0.3 | 0.25 | 0.28 | 0.19 | 0.18 | 0.27 |
| Sum | 99.9 | 99.9 | 100.0 | 100.0 | 100.0 | 100.0 | 99.9 | 100.0 | 99.8 |

TABLE 14

Mean Phytotoxicity Index of 9 sunflower lines (each value is the mean of 20 replications).

| Phytotoxicity Index | Lines | | | | | | | | |
|---|---|---|---|---|---|---|---|---|---|
| | BTI-OL-M1511 | BTI-OL-M1709 | BTI-OL-2201 | VB141 | HA445 | OB712 | GM40 | B770 | BTK112 |
| PI | 0.5 | 0.2 | 0.2 | 8.5 | 8.8 | 9 | 0.2 | 8.7 | 9 |

Example 9: Field Evaluations and AHAS Activity Evaluations for A122T/A122T, A205V/A205V and A122T/A205V Events Field evaluations were conducted across several locations to determine the relative imidazolinone tolerance levels of sunflower plants that are A122T/A122T, A122T/A205V, or A205V/A205V for the AHASL1 gene. Sunflower plants from each of the different genotypes were challenged with different doses of imazamox and imazapyr under a range of environmental conditions. In addition, in vitro AHAS activity was determined in the presence of increasing levels of herbicides for sunflower plants from each of the three sunflower genotypes.

TABLE 15

Entry List for Herbicide Tolerance Field Evaluations (2007)

| Entry | Line Description | AHASL1 Allele Zygosity |
|---|---|---|
| 1 | GM40 | A122T Homozygous |
| 2 | cmsGM40 × R733 | A122T Homozygous |
| 3 | cmsBTK47 × R731 | A122T Heterozygous |
| 4 | IA9 × R733 | A22T/A205V |
| 5 | IA9 × RHA426 | A205V Homozygous |
| 6 | B7imi (IMISUN1) | A205V Homozygous |
| 7 | cmsB7 × RHA426 | A205V Heterozygous |
| 8 | B7 | WT |

TABLE 16

Location List for Herbicide Tolerance
Field Evaluations (2005-2007)

| Year | Country | Nearest Town Location, State or Province |
|---|---|---|
| 2005 | USA | Velva North Dakota |
| 2005/2006 | Argentina (AR) | Venado Tuerto, Santa Fe |
| 2006 | USA | Velva North Dakota |
| 2006/2007 | Argentina | Venado Tuerto, Santa Fe |
| 2006/2007 | Argentina | Balcarce, Buenos Aires |
| 2007 | Argentina | Laguna Blanca, Formosa |
| 2007 | USA | Velva North Dakota |
| 2007 | USA | Hickson, North Dakota |
| 2007 | France (FR) | Angers |
| 2007 | France | Saintes |
| 2007/2008 | Argentina | Venado Tuerto, Santa Fe |
| 2007/2008 | Argentina | San Jeronimo, Santa Fe |
| 2007/2008 | Argentina | Balcarce, Buenos Aires |

The entries at each location in 2007 and 2007/2008 were arranged in a randomized two factorial split plot design consisting of 3 replications for each treatment combination. Factor A was the herbicide treatment (Table 20), and factor B was the sunflower entry (Table 18). The plot size was 2 rows×7 m and the seeding rate was consistent with local agronomic practices. The herbicide treatment was applied at the 2-4 leaf stage with a tractor mounted boom (20 gallons/acre or 200 liters/ha). Treatment 2 was only applied at 2 locations in France.

TABLE 17

Imidazolinone Treatment List for Herbicide
Tolerance Field Evaluations (2007)

| Treatment Number | Herbicide Treatment | Herbicide Product Formulation |
|---|---|---|
| 1 | Untreated | |
| 2 | 50 g ai/ha imazamox + 0.25% (v/v) NIS* | Beyond 120 g/l LC |
| 3 | 100 g ai/ha imazamox + 0.25% (v/v) NIS* | Beyond 120 g/l LC |
| 4 | 200 g ai/ha imazamox + 0.25% (v/v) NIS* | Beyond 120 g/l LC |
| 5 | 160 g ai/ha imazapyr + 0.25% (v/v) NIS* | Arsenal 240 g ai/L |
| 6 | 320 g ai/ha imazapyr + 0.25% (v/v) NIS* | Arsenal 240 g ai/L |

*NIS = non-ionic surfactant = Induce 90SC (90%)

Crop injury (% phytotoxicity) ratings were evaluated at 6-10 days after treatment and at 16-21 days after treatment. Percent phytotoxicity was recorded as the average amount of plant damage in a given plot, where a rating of '0%' indicated no damage to plants relative to the untreated plot. A rating of 10% to 40% indicated increasing levels of chlorosis (where 40 would be complete yellowing of the leaves). A rating of 50% or higher indicated that the plants demonstrated complete yellowing as well as increasing levels of leaf necrosis. A rating of '100%' indicated complete necrosis (death) of the plants.

The emergence, days to flower, days to end of flower and maturity were also assessed for each plot at each location (data not shown). The data were subjected to an ANOVA analysis.

Enzyme Assay for AHAS Activity

Twelve greenhouse grown sunflower plants from each of the lines depicted in Table 21 were bulked and subjected to an AHAS enzyme activity assay via the method of Singh et al. (1988) *Anal. Biochem.* 171:173-179. Each activity assay was repeated twice. Due to the large number of samples, the experiment was split into two sets (Table 21).

TABLE 18

Line Descriptions and Corresponding
AHASL1 Mutation Allele Zygosities

| Set | Line Description | ABASL1 Allele Zygosity |
|---|---|---|
| 1 | cmsGM40 × R733 | A122T Homozygous |
| 1 | IA9 × R733 | A122T/A205V Heterozygous |
| 1 | IA9 × RHA426 | A205V Homozygous |
| 1 | B7 | WT |
| 2 | GM40 | A122T Homozygous |
| 2 | cmsBTK47 × R731 | A122T Heterozygous |
| 2 | B7imi (IMISUN1) | A205V Homozygous |
| 2 | cmsB7 × RHA426 | A205V Heterozygous |
| 2 | B7 | WT |

Young, actively growing leaves, from four week old plantlets, were ground in a mortar and pestle with liquid $N_2$ and extracted with a buffer composed of 100 mM pyruvate, 200 mM $KH_2PO_4$, 20 mM $MgCl_2$, 2 mM thiamine pyrophosphate and 20 µM flavin adenine dinucleotide. Plant extracts were then spun through a 10 mL Zeba™ desalt spin column (Pierce #89893) as per the manufacturer's recommendation. The inhibition assay was performed as described by Singh et al. (1988) *Anal. Biochem.* 171:173-179. Assays were conducted in a 96-well format. Fifty µl of inhibitor was added to each well containing 50 µl of soluble protein extract to give final concentrations of 0.78, 1.56, 3.125, 6.25, 12.5, 25, 50 and 100 µM imazamox or 0.78, 1.56, 3.125, 6.25, 12.5, 25, 50 and 100 µM imazapyr. Zero herbicide controls were also included for each line. Reactions were processed as outlined by Singh et al. (1988) *Anal. Biochem.* 171:173-179. Absorbance was measured at 530 nm. AHAS activity, expressed as the mean of the absorbance values for each treatment, was presented as a percentage of the mean of the zero-herbicide controls.

Results and Discussion

In herbicide tolerant crops, the crop injury phenotype can be attributed to the interaction between genotype and environment (GxE). The environmental component for herbicide tolerance is a sum of abiotic (i.e. weather, soil) and biotic factors (i.e. insect, disease and weed pressure) coupled with the effect of the herbicide dose. An example of this environmental effect is seen in FIG. 10, where the variation in phytotoxicity of the same genotype grown in four different locations (Velva, N. Dak., USA; Angers, FR; Saintes FR; Formosa, AR) at the same dose rate (200 g ai/ha imazamox) is demonstrated. The genotypic factor in a herbicide tolerant (HT) plant is the sum of the HT gene(s) plus the remaining genetic background, and the interaction between the two.

To assess HT genes for their relative tolerance level, two approaches were used. The first approach measured herbicide injury under a range of environmental stringencies (locations and years in combination with different herbicide doses), and the second approach tested the target enzyme (in vitro) with increasing levels of herbicide. Using the first approach, we quantified the environmental factor associated with this trait, by calculating the mean phytotoxicity index (PI) of the current commercial, regionally adapted, A205V checks at 6-10 days after herbicide treatment. PI values for different hybrids carrying the A122T mutation were plotted against the mean PI values of the A205V checks to evaluate the relative resistance level of the new mutation across a range of environmental components (FIGS. 11 and 12). As can be seen in the x axis of FIGS. 11 and 12, the combination of locations with herbicide doses produced a diverse array of environmental conditions, which ranged in PI mean values from 5.9 to 78 for the imazamox treatments; and 2 to 100 for the imazapyr treatments. The y=x line represented the mean PI value for the A205V checks across all environmental components.

The results obtained after imazamox treatments are shown in FIG. 11. The A122T homozygous hybrids showed an increase in PI as the environmental component became more severe. However, the slope of the regression line (b=0.149±0.0667, P<0.0375) indicated that the level of crop injury as a function of environmental stringency increased at a lower rate than the A205V checks. The hybrids which combined the A122T mutation with the A205V allele in a heterozygous state, showed a similar response to environmental stringency (b=0.39±0.05, P<0.0001) as the A122T hybrids in a homozygous state. On the other hand, the hybrids containing the A122T mutation in a heterozygous state (A122T/WT) demonstrated higher crop injury ratings than the A205V checks at lower levels of environmental stringency, as shown by the higher y-intercept value of the regression line (a=15.3±2.67). When the severity of the environmental component was increased, these A122T heterozygous hybrids showed a better performance than the A205V checks, as was shown by the slope of its linear equation (b=0.45±0.062, P<0.0001). The same applies for FIG. 12 when the same entries, in the same environments, were challenged with imazapyr.

The environmental stringencies with imazapyr treatment can be summarized by the regressions summarized in the legend for each genotype in FIG. 12.

To substantiate the herbicide tolerance effect observed in the field, the same herbicide tolerance gene combinations were subjected to AHAS enzyme inhibition studies. These studies were conducted on the bulk of 12 individuals from each entry in Table 18. The mean of two replications are represented in FIG. 13 for the first experiment (Set 1, Table 21) and in FIG. 14 for the second experiment (Set 2, Table 21). An untreated control sample was included to provide a baseline for 100% AHAS enzyme activity. The AHAS activity in the A122T homozygous hybrid treated with 100 µM imazamox was 69% of the untreated control, and for the 100 µM imazapyr it was 64% of the untreated control (FIG. 13). The activity of the AHAS enzyme in the A122T/A205V heterozygous hybrid was 59% and 60% for the extracts treated with 100 µM imazamox and 100 µM imazapyr respectively (FIG. 13). The A205V homozygous hybrids line, which is the current commercial A205V product, demonstrated AHAS activities of 36% of untreated control and 42% of untreated control at 100 µM imazamox and 100 µM imazapyr respectively (FIG. 13), lower than the activities of both the A122T homozygous hybrid and the A122T/A205V heterozygous hybrid.

In the second set of data, the A205V homozygous hybrids performed almost identically to the A122T heterozygous hybrids (FIG. 14). Both type of hybrids demonstrated AHAS activities of 30% at 50 µM imazamox, while the A205V hybrid had 26% activity at 100 µM imazamox and the A122T heterozygous hybird had 30% activity at 100 µM imazamox. In contrast, the AHAS enzyme extract from the A122T homozygous hybrid demonstrated the least amount of inhibition with increasing levels of imazamox, demonstrating activities of 63% and 60%, relative to the untreated control, at 50 µM and 100 µM imazamox respectively (FIG. 14). The WT line (B7) was genotypically identical in both experimental sets and demonstrated a variance of 6% activity at the 100 µM imazamox level between the two experiments (17% AHAS activity relative to the untreated control in Set 1 (FIG. 13) and 11% AHAS activity relative to the untreated control in Set 2 (FIG. 14).

Based on field and AHAS enzyme activity data, it was determined that the novel A122T mutation provides superior herbicide tolerance to imidazolinones versus the current A205V mutation. Commercial levels of herbicide resistance in A205V sunflowers require the combination of two genetic factors in a homozygous state due to the moderate level of resistance conferred by Imr1. In contrast, by using the A122T mutation alone, the Imr2 enhancer (or gene by genotype interaction) is no longer necessary to achieve commercial levels of tolerance. Most importantly, the results demonstrate that A122T can be used either as a homozygous single gene HT trait or as a heterozygous stack together with the A205V HT trait, providing enhanced levels of tolerance, greater flexibility in weed control and facilitating the deployment of this new mutation in the CLEARFIELD Production System.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. A method for genotyping a sunflower acetohydroxyacid synthase large subunit 1 (AHASL1) gene, said method comprising:
   (a) obtaining DNA from a sunflower plant;
   (b) using the DNA of step (a) as a template for a first polymerase chain reaction (PCR) amplification comprising said DNA, polymerase, deoxyribonucleotide triphosphates, a forward AHASL1 primer, and a reverse wild-type AHASL1 primer comprising the nucleotide sequence of SEQ ID NO:4,
   (c) using the DNA of (a) as a template for a second PCR amplification comprising said DNA, polymerase, deoxyribonucleotide triphosphates, the forward AHASL1 primer, and a reverse mutant AHASL1 primer comprising the nucleotide sequence of SEQ ID NO:5; and
   (d) detecting products of said first PCR amplification and said second PCR amplification.

2. The method of claim 1, wherein said forward AHASL1 primer comprises the nucleotide sequence of SEQ ID NO:3.

3. The method of claim 1, wherein said first PCR amplification and said second PCR amplification are performed in separate reactions.

4. The method of claim 1, wherein said first PCR amplification and said second PCR amplification are performed in the same reaction.

5. A kit for genotyping a sunflower acetohydroxyacid synthase large subunit 1 (AHASL1) gene, said kit comprising (a) a forward AHASL1 primer,
   (b) a reverse wild-type AHASL1 primer comprising the nucleotide sequence of SEQ ID NO:4, and
   (c) a reverse mutant AHASL1 primer comprising a nucleotide sequence of SEQ ID NO:5.

6. The kit of claim 5, further comprising deoxyribonucleotide triphosphates and a polymerase capable of catalyzing the PCR amplification of a fragment of a sunflower AHASL1 gene having an A122T allele; or a fragment of a wild-type sunflower AHASL1 gene.

7. The kit of claim 5, wherein said forward AHASL1 primer comprises the nucleotide sequence of SEQ ID NO:3.

8. A method for genotyping a sunflower acetohydroxyacid synthase large subunit 1 (AHASL1) gene, said method comprising:
   (a) obtaining DNA from a sunflower plant;
   (b) using said DNA as a template for a first polymerase chain reaction (PCR) amplification comprising said DNA, polymerase, deoxyribonucleotide triphosphates, a first forward AHASL1 primer comprising the nucleotide sequence of SEQ ID NO:15, and a first reverse AHASL1 primer comprising the nucleotide sequence of SEQ ID NO:16;
   (c) using said DNA as a template for a second PCR amplification comprising said DNA, polymerase, deoxyribonucleotide triphosphates, a second forward AHASL1 primer comprising the nucleotide sequence of SEQ ID NO:17, and a second reverse AHASL1 primer comprising the nucleotide sequence of SEQ ID NO:18; and (d) detecting products of said first PCR amplification and said second PCR amplification.

9. The method of claim 8, wherein said first PCR amplification and said second PCR amplification are performed in separate reactions.

10. The method of claim 8, wherein said first PCR amplification and said second PCR amplification are performed in the same reaction.

11. A kit for genotyping a sunflower acetohydroxyacid synthase large subunit 1 (AHASL1) gene, said kit comprising:
   (a) a first forward AHASL1 primer comprising the nucleotide sequence of SEQ ID NO:15, and
   a first reverse AHASL1 primer comprising the nucleotide sequence of SEQ ID NO:16; and
   (b) a second forward AHASL1 primer comprising the nucleotide sequence of SEQ ID NO:17, and
   a second reverse AHASL1 primer comprising the nucleotide sequence of SEQ ID NO:18.

12. The kit of claim 11, further comprising deoxyribonucleotide triphosphates and a polymerase capable of catalyzing the PCR amplification of:
   a fragment of a sunflower AHASL1 gene having an A122T allele or
   a fragment of a wild type sunflower AHASL1 gene.

* * * * *

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: PCR Primer

<400> SEQUENCE: 1 ttcctcccc gtttcgcatt ac                                              22

<210> SEQ ID NO 2

```
<211> LENGTH: 18
<212> TYPE: DNA
<213> ORGANISM: Artificial Sequence
<220> FEATURE:
<223> OTHER INFORMATION: PCR Primer

<400> SEQUENCE: 2
cgccgccctg ttcgtgac                                                     18

<210> SEQ ID NO 3
<211> LENGTH: 18
<212> TYPE: DNA
<213> ORGANISM: Artificial Sequence
<220> FEATURE:
<223> OTHER INFORMATION: PCR Primer

<400> SEQUENCE: 3
tgttctctcc gactctaa                                                     18

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
tggtggatct ccattgagtc                                                   20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
tggtggatct ccattgagtt                                                   20

<210> SEQ ID NO 6
<211> LENGTH: 195
<212> TYPE: DNA
<213> ORGANISM: Helianthus annuus
<220> FEATURE:
<221> NAME/KEY: misc_feature
<222> LOCATION: (1)...(195)
<223> OTHER INFORMATION: Hap1

<400> SEQUENCE: 6
tgttctctcc gactccaaat ccaccaccac caccaccacc accactcaac gaccgttacc        60
ggtgcagcct tttgtctccc gttacgcgcc agatcaaccg agaaaaggcg cagacgtgtt       120
ggtggaagct ctggaacggg aaggtgtcac cgacgtcttc gcctacccccg gcggcgcgtc      180 aatggagatc cacca                                                       195

<210> SEQ ID NO 7
<211> LENGTH: 192
<212> TYPE: DNA
<213> ORGANISM: Helianthus annuus
<220> FEATURE:
<221> NAME/KEY: misc_feature
<222> LOCATION: (1)...(192)
<223> OTHER INFORMATION: Hap2

<400> SEQUENCE: 7
tgttctctcc gactccaaat ccaccaccac caccaccacc actcaaccac cgttacaggc        60
```

```
gcagccttttt gtctcccggt acgcgccaga tcaaccgaga aaaggcgcag acgtgttggt    120
ggaagctctg gaacgggaag gtgtcaccga cgtcttcgcc tacccggcg gcgcgtcaat     180 ggagatccac ca                                                        192
```

<210> SEQ ID NO 8
<211> LENGTH: 204
<212> TYPE: DNA
<213> ORGANISM: Helianthus annuus
<220> FEATURE:
<221> NAME/KEY: misc_feature
<222> LOCATION: (1)...(204)
<223> OTHER INFORMATION: Hap3

<400> SEQUENCE: 8

```
tgttctctcc gactccaaat ccaccaccac caccaccacc accaccacca ccactcaacc    60
accgttacag gcgcagcctt tgtctcccg ttacgcgcct gatcaaccga gaaaaggcgc     120
agacgtgttg gtggaagctc tggaacggga aggtgtcacc gacgtcttcg cctacccgg     180 cggcgcgtca atggagatcc acca                                           204
```

<210> SEQ ID NO 9
<211> LENGTH: 186
<212> TYPE: DNA
<213> ORGANISM: Helianthus annuus
<220> FEATURE:
<221> NAME/KEY: misc_feature
<222> LOCATION: (1)...(186)
<223> OTHER INFORMATION: Hap4

<400> SEQUENCE: 9

```
tgttctctcc gactccaaat ccaccaccac caccactcaa ccaccgttac aggcgcagcc    60
ttttgtctcc cgttacgcgc cagatcaacc gagaaaaggc gcagacgtgt tggtggaagc    120
tctggaacgg gaaggtgtca ccgacgtctt cgcctacccc ggcggcgcgt caatggagat    180
ccacca                                                               186
```

<210> SEQ ID NO 10
<211> LENGTH: 186
<212> TYPE: DNA
<213> ORGANISM: Helianthus annuus
<220> FEATURE:
<221> NAME/KEY: misc_feature
<222> LOCATION: (1)...(186)
<223> OTHER INFORMATION: Hap5

<400> SEQUENCE: 10

```
tgttctctcc gactccaaat ccaccaccac caccactcaa ccaccgttac aggcgcagcc    60
ttttgtctcc cgttacgcgc cagatcaacc gagaaaaggc gcagacgtgt tggtggaagc    120
tctagaacgg gaaggtgtca ccgacgtctt cgcctacccc ggcggcgcgt caatggagat    180
ccacca                                                               186
```

<210> SEQ ID NO 11
<211> LENGTH: 195
<212> TYPE: DNA
<213> ORGANISM: Helianthus annuus
<220> FEATURE:
<221> NAME/KEY: misc_feature
<222> LOCATION: (1)...(195)
<223> OTHER INFORMATION: Hap6

<400> SEQUENCE: 11

```
tgttctctcc gactccaaat ccaccaccac caccaccacc accactcaac gaccgttacc    60
ggtgcagcct tttgtctccc gttacgcgcc agatcaaccg agaaaaggcg cagacgtgtt   120
ggtggaagct ctggaacggg aaggtgtcac cgacgtcttc gcctaccccg gcggcacgtc   180
aatggagatc cacca                                                    195
```

```
<210> SEQ ID NO 12
<211> LENGTH: 19
<212> TYPE: DNA
<213> ORGANISM: Helianthus annuus

<400> SEQUENCE: 12
tgttctctcc gactccaaa                                                 19

<210> SEQ ID NO 13
<211> LENGTH: 20
<212> TYPE: DNA
<213> ORGANISM: Helianthus annuus
<220> FEATURE:
<221> NAME/KEY: allele
<222> LOCATION: (1)...(20)
<223> OTHER INFORMATION: wild-type allele

<400> SEQUENCE: 13
gcgtcaatgg agatccacca                                                20

<210> SEQ ID NO 14
<211> LENGTH: 20
<212> TYPE: DNA
<213> ORGANISM: Helianthus annuus
<220> FEATURE:
<221> NAME/KEY: allele
<222> LOCATION: (1)...(10)
<223> OTHER INFORMATION: mutant allele; position 1 site of SNP

<400> SEQUENCE: 14
acgtcaatgg agatccacca                                                20

<210> SEQ ID NO 15
<211> LENGTH: 20
<212> TYPE: DNA
<213> ORGANISM: Artificial Sequence
<220> FEATURE:
<223> OTHER INFORMATION: PCR Primer HA122CF

<400> SEQUENCE: 15
gtttcgcatt acccatcact                                                20

<210> SEQ ID NO 16
<211> LENGTH: 19
<212> TYPE: DNA
<213> ORGANISM: Artificial Sequence
<220> FEATURE:
<223> OTHER INFORMATION: PCR Primer HA122wt

<400> SEQUENCE: 16
ggtggatctc cattaacgc                                                 19

<210> SEQ ID NO 17
<211> LENGTH: 16
<212> TYPE: DNA
<213> ORGANISM: Artificial Sequence
<220> FEATURE:
<223> OTHER INFORMATION: PCR Primer HA122mut

<400> SEQUENCE: 17
```

```
gcctaccccg gctgca                                                    16

<210> SEQ ID NO 18
<211> LENGTH: 18
<212> TYPE: DNA
<213> ORGANISM: Artificial Sequence
<220> FEATURE:
<223> OTHER INFORMATION: PCR Primer HA122CR

<400> SEQUENCE: 18
caaaaccggc tcttcgc                                                   18

<210> SEQ ID NO 19
<211> LENGTH: 1178
<212> TYPE: DNA
<213> ORGANISM: Helianthus annuus
<220> FEATURE:
<221> NAME/KEY: CDS
<222> LOCATION: (3)...(1178)

<400> SEQUENCE: 19 tc ttc gcc tac ccc ggc ggc acg tca atg gag atc cac caa gct ctc        47
   Phe Ala Tyr Pro Gly Gly Thr Ser Met Glu Ile His Gln Ala Leu
    1               5                  10                  15 acg cgc tca agc act atc cgc aat gtg ctc ccc cgt cac gaa cag ggc       95
Thr Arg Ser Ser Thr Ile Arg Asn Val Leu Pro Arg His Glu Gln Gly
                 20                  25                  30 ggc gtg ttc gcc gcc gaa ggc tac gcg cgc gcc tcc ggt ctt ccc ggc      143
Gly Val Phe Ala Ala Glu Gly Tyr Ala Arg Ala Ser Gly Leu Pro Gly
             35                  40                  45 gtg tgt atc gcc act tcc ggt ccc gga gct acg aac cta gtt agt ggt      191
Val Cys Ile Ala Thr Ser Gly Pro Gly Ala Thr Asn Leu Val Ser Gly
         50                  55                  60 ctt gct gac gcg ctg tta gac agt gtc ccc atg gtg gca atc acc ggt      239
Leu Ala Asp Ala Leu Leu Asp Ser Val Pro Met Val Ala Ile Thr Gly
     65                  70                  75 caa gtt ccc cgg aga atg atc gga acc gat gcg ttt caa gaa acc cca      287
Gln Val Pro Arg Arg Met Ile Gly Thr Asp Ala Phe Gln Glu Thr Pro
 80                  85                  90                  95 att gtt gag gta aca cgt tcg atc act aaa cat aat tat ctt gtg ttg      335
Ile Val Glu Val Thr Arg Ser Ile Thr Lys His Asn Tyr Leu Val Leu
                100                 105                 110 gat gtt gag gat att ccc aga att gtt cgt gag gct ttt tat ctt gcg      383
Asp Val Glu Asp Ile Pro Arg Ile Val Arg Glu Ala Phe Tyr Leu Ala
            115                 120                 125 agt tcg ggt cga ccc ggc ccg gtt ttg ata gat gta ccg aaa gat ata      431
Ser Ser Gly Arg Pro Gly Pro Val Leu Ile Asp Val Pro Lys Asp Ile
        130                 135                 140 cag caa cag tta gtg gtg ccg aaa tgg gat gaa ccg atg agg tta ccg      479
Gln Gln Gln Leu Val Val Pro Lys Trp Asp Glu Pro Met Arg Leu Pro
145                 150                 155 ggt tat ttg tct aga atg ccg aag cct caa tat gat ggg cat ttg gaa      527
Gly Tyr Leu Ser Arg Met Pro Lys Pro Gln Tyr Asp Gly His Leu Glu
160                 165                 170                 175 cag att gtt agg ttg gtg ggg gaa gcg aag agg ccg gtt ttg tat gtg      575
Gln Ile Val Arg Leu Val Gly Glu Ala Lys Arg Pro Val Leu Tyr Val
                180                 185                 190 ggt ggt ggg tgt ttg aat tcg gat gat gag ttg agg cgg ttt gtg gag      623
Gly Gly Gly Cys Leu Asn Ser Asp Asp Glu Leu Arg Arg Phe Val Glu
            195                 200                 205 ctt acg ggg att ccg gtt gcg agt act ttg atg ggg ctc gga gcg tac      671
Leu Thr Gly Ile Pro Val Ala Ser Thr Leu Met Gly Leu Gly Ala Tyr
```

|  |  |  |  |  |  |  |  |  |  |  |  |  |  |
|---|---|---|---|---|---|---|---|---|---|---|---|---|---|
| Leu | Thr | Gly 210 | Ile | Pro | Val | Ala 215 | Ser | Thr | Leu | Met 220 | Gly | Leu | Gly | Ala | Tyr |

```
cct gct tcg agt gat ttg tcg ctt cat atg ctt ggg atg cat ggt acg      719
Pro Ala Ser Ser Asp Leu Ser Leu His Met Leu Gly Met His Gly Thr
    225                 230                 235 gtt tat gcg aat tat gcg gtt gat aag agt gat ttg ttg ctt gcg ttt      767
Val Tyr Ala Asn Tyr Ala Val Asp Lys Ser Asp Leu Leu Leu Ala Phe
240                 245                 250                 255 ggg gtg cgg ttt gat gat cgt gtg acg ggg aag ctt gag gcg ttt gct      815
Gly Val Arg Phe Asp Asp Arg Val Thr Gly Lys Leu Glu Ala Phe Ala
                260                 265                 270 agt agg gcg aag att gtt cat att gat att gat cct gct gaa att ggg      863
Ser Arg Ala Lys Ile Val His Ile Asp Ile Asp Pro Ala Glu Ile Gly
            275                 280                 285 aag aat aag cag cct cat gtg tcg att tgt ggt gat att aag gtc gcg      911
Lys Asn Lys Gln Pro His Val Ser Ile Cys Gly Asp Ile Lys Val Ala
        290                 295                 300 tta cag ggt ttg aac aag att ttg gag gaa aag aat tcg gtg act aat      959
Leu Gln Gly Leu Asn Lys Ile Leu Glu Glu Lys Asn Ser Val Thr Asn
305                 310                 315 ctt gat ttt tcg acc tgg aga aag gaa ttg gat gaa caa aaa atg aag     1007
Leu Asp Phe Ser Thr Trp Arg Lys Glu Leu Asp Glu Gln Lys Met Lys
320                 325                 330                 335 ttc ccg ttg agc ttt aaa acg ttt ggc gaa gcg att cct cca cag tat     1055
Phe Pro Leu Ser Phe Lys Thr Phe Gly Glu Ala Ile Pro Pro Gln Tyr
                340                 345                 350 gct att caa gtt ctt gat gag tta acg ggc ggg aat gca att att agc     1103
Ala Ile Gln Val Leu Asp Glu Leu Thr Gly Gly Asn Ala Ile Ile Ser
            355                 360                 365 acc ggt gtc ggg caa cat cag atg tgg gct gct cag ttt tac aaa tac     1151
Thr Gly Val Gly Gln His Gln Met Trp Ala Ala Gln Phe Tyr Lys Tyr
        370                 375                 380 aac aaa cct aga caa tgg ctg acg tcg                                  1178
Asn Lys Pro Arg Gln Trp Leu Thr Ser
    385                 390
```

<210> SEQ ID NO 20
<211> LENGTH: 392
<212> TYPE: PRT
<213> ORGANISM: Helianthus annuus

<400> SEQUENCE: 20

```
Phe Ala Tyr Pro Gly Gly Thr Ser Met Glu Ile His Gln Ala Leu Thr
1               5                   10                  15

Arg Ser Ser Thr Ile Arg Asn Val Leu Pro Arg His Glu Gln Gly Gly
            20                  25                  30

Val Phe Ala Ala Glu Gly Tyr Ala Arg Ala Ser Gly Leu Pro Gly Val
        35                  40                  45

Cys Ile Ala Thr Ser Gly Pro Gly Ala Thr Asn Leu Val Ser Gly Leu
    50                  55                  60

Ala Asp Ala Leu Leu Asp Ser Val Pro Met Val Ala Ile Thr Gly Gln
65                  70                  75                  80

Val Pro Arg Arg Met Ile Gly Thr Asp Ala Phe Gln Glu Thr Pro Ile
                85                  90                  95

Val Glu Val Thr Arg Ser Ile Thr Lys His Asn Tyr Leu Val Leu Asp
            100                 105                 110

Val Glu Asp Ile Pro Arg Ile Val Arg Glu Ala Phe Tyr Leu Ala Ser
        115                 120                 125
```

-continued

```
Ser Gly Arg Pro Gly Pro Val Leu Ile Asp Val Pro Lys Asp Ile Gln
130                 135                 140

Gln Gln Leu Val Val Pro Lys Trp Asp Glu Pro Met Arg Leu Pro Gly
145                 150                 155                 160

Tyr Leu Ser Arg Met Pro Lys Pro Gln Tyr Asp Gly His Leu Glu Gln
                165                 170                 175

Ile Val Arg Leu Val Gly Glu Ala Lys Arg Pro Val Leu Tyr Val Gly
            180                 185                 190

Gly Gly Cys Leu Asn Ser Asp Asp Glu Leu Arg Arg Phe Val Glu Leu
        195                 200                 205

Thr Gly Ile Pro Val Ala Ser Thr Leu Met Gly Leu Gly Ala Tyr Pro
    210                 215                 220

Ala Ser Ser Asp Leu Ser Leu His Met Leu Gly Met His Gly Thr Val
225                 230                 235                 240

Tyr Ala Asn Tyr Ala Val Asp Lys Ser Asp Leu Leu Leu Ala Phe Gly
                245                 250                 255

Val Arg Phe Asp Asp Arg Val Thr Gly Lys Leu Glu Ala Phe Ala Ser
            260                 265                 270

Arg Ala Lys Ile Val His Ile Asp Ile Asp Pro Ala Glu Ile Gly Lys
        275                 280                 285

Asn Lys Gln Pro His Val Ser Ile Cys Gly Asp Ile Lys Val Ala Leu
    290                 295                 300

Gln Gly Leu Asn Lys Ile Leu Glu Glu Lys Asn Ser Val Thr Asn Leu
305                 310                 315                 320

Asp Phe Ser Thr Trp Arg Lys Glu Leu Asp Glu Gln Lys Met Lys Phe
                325                 330                 335

Pro Leu Ser Phe Lys Thr Phe Gly Glu Ala Ile Pro Pro Gln Tyr Ala
            340                 345                 350

Ile Gln Val Leu Asp Glu Leu Thr Gly Gly Asn Ala Ile Ile Ser Thr
        355                 360                 365

Gly Val Gly Gln His Gln Met Trp Ala Ala Gln Phe Tyr Lys Tyr Asn
    370                 375                 380

Lys Pro Arg Gln Trp Leu Thr Ser
385                 390
```

```
<210> SEQ ID NO 21
<211> LENGTH: 1716
<212> TYPE: DNA
<213> ORGANISM: Helianthus annuus
<220> FEATURE:
<221> NAME/KEY: CDS
<222> LOCATION: (1)...(1716)

<400> SEQUENCE: 21
```

```
gca gac gtg ttg gtg gaa gct ctg gaa cgg gaa ggt gtc acc gac gtc    48
Ala Asp Val Leu Val Glu Ala Leu Glu Arg Glu Gly Val Thr Asp Val
 1               5                   10                  15 ttc gcc tac ccc ggc ggc gcg tca atg gag atc cac caa gct ctc acg    96
Phe Ala Tyr Pro Gly Gly Ala Ser Met Glu Ile His Gln Ala Leu Thr
                20                  25                  30 cgc tca agc act atc cgc aat gtg ctc ccc cgt cac gaa cag ggc ggc   144
Arg Ser Ser Thr Ile Arg Asn Val Leu Pro Arg His Glu Gln Gly Gly
            35                  40                  45 gtg ttc gcc gcc gaa ggc tac gcg cgc gcc tcc ggt ctt ccc ggc gtg   192
Val Phe Ala Ala Glu Gly Tyr Ala Arg Ala Ser Gly Leu Pro Gly Val
        50                  55                  60 tgt atc gcc act tcc ggt ccc gga gct acg aac cta gtt agt ggt ctt   240
```

```
                Cys Ile Ala Thr Ser Gly Pro Gly Ala Thr Asn Leu Val Ser Gly Leu
                 65                  70                  75                  80 gct gac gcg ctg tta gac agt gtc ccc atg gtg gca atc acc ggt caa         288
Ala Asp Ala Leu Leu Asp Ser Val Pro Met Val Ala Ile Thr Gly Gln
                 85                  90                  95 gtt ctc cgg aga atg atc gga acc gat gcg ttt caa gaa acc cca att         336
Val Leu Arg Arg Met Ile Gly Thr Asp Ala Phe Gln Glu Thr Pro Ile
            100                 105                 110 gtt gag gta aca cgt tcg atc act aaa cat aat tat ctt gtg ttg gat         384
Val Glu Val Thr Arg Ser Ile Thr Lys His Asn Tyr Leu Val Leu Asp
            115                 120                 125 gtt gag gat att ccc aga att gtt cgt gag gct ttt tat ctt gcg agt         432
Val Glu Asp Ile Pro Arg Ile Val Arg Glu Ala Phe Tyr Leu Ala Ser
        130                 135                 140 tcg ggt cga ccc ggc ccg gtt ttg ata gat gta ccg aaa gat ata cag         480
Ser Gly Arg Pro Gly Pro Val Leu Ile Asp Val Pro Lys Asp Ile Gln
145                 150                 155                 160 caa cag tta gtg gtg ccg aaa tgg gat gaa ccg atg agg tta ccg ggt         528
Gln Gln Leu Val Val Pro Lys Trp Asp Glu Pro Met Arg Leu Pro Gly
                165                 170                 175 tat ttg tct aga atg ccg aag cct caa tat gat ggg cat ttg gaa cag         576
Tyr Leu Ser Arg Met Pro Lys Pro Gln Tyr Asp Gly His Leu Glu Gln
            180                 185                 190 att gtt agg ttg gtg ggg gaa gcg aag agg ccg gtt ttg tat gtg ggt         624
Ile Val Arg Leu Val Gly Glu Ala Lys Arg Pro Val Leu Tyr Val Gly
            195                 200                 205 ggt ggg tgt ttg aat tcg gat gat gag ttg agg cgg ttt gtg gag ctt         672
Gly Gly Cys Leu Asn Ser Asp Asp Glu Leu Arg Arg Phe Val Glu Leu
        210                 215                 220 acg ggg att ccg gtt gcg agt act ttg atg ggg ctc gga gcg tac cct         720
Thr Gly Ile Pro Val Ala Ser Thr Leu Met Gly Leu Gly Ala Tyr Pro
225                 230                 235                 240 gct tcg agt gat ttg tcg ctt cat atg ctt ggg atg cat ggt acg gtt         768
Ala Ser Ser Asp Leu Ser Leu His Met Leu Gly Met His Gly Thr Val
                245                 250                 255 tat gcg aat tat gcg gtt gat aag agt gat ttg ttg ctt gcg ttt ggg         816
Tyr Ala Asn Tyr Ala Val Asp Lys Ser Asp Leu Leu Leu Ala Phe Gly
            260                 265                 270 gtg cgg ttt gat gat cgt gtg acg ggg aag ctt gag gcg ttt gct agt         864
Val Arg Phe Asp Asp Arg Val Thr Gly Lys Leu Glu Ala Phe Ala Ser
            275                 280                 285 agg gcg aag att gtt cat att gat att gat cct gct gaa att ggg aag         912
Arg Ala Lys Ile Val His Ile Asp Ile Asp Pro Ala Glu Ile Gly Lys
        290                 295                 300 aat aag cag cct cat gtg tcg att tgt ggt gat att aag gtc gcg tta         960
Asn Lys Gln Pro His Val Ser Ile Cys Gly Asp Ile Lys Val Ala Leu
305                 310                 315                 320 cag ggt ttg aac aag att ttg gag gaa aag aat tcg gtg act aat ctt        1008
Gln Gly Leu Asn Lys Ile Leu Glu Glu Lys Asn Ser Val Thr Asn Leu
                325                 330                 335 gat ttt tcg acc tgg aga aag gaa ttg gat gaa caa aaa atg aag ttc        1056
Asp Phe Ser Thr Trp Arg Lys Glu Leu Asp Glu Gln Lys Met Lys Phe
            340                 345                 350 ccg ttg agc ttt aaa acg ttt ggc gaa gcg att cct cca cag tat gct        1104
Pro Leu Ser Phe Lys Thr Phe Gly Glu Ala Ile Pro Pro Gln Tyr Ala
            355                 360                 365 att caa gtt ctt gat gag tta acg ggc ggg aat gca att att agc acc        1152
Ile Gln Val Leu Asp Glu Leu Thr Gly Gly Asn Ala Ile Ile Ser Thr
        370                 375                 380
```

```
ggt gtc ggg caa cat cag atg tgg gct gct cag ttt tac aaa tac aac     1200
Gly Val Gly Gln His Gln Met Trp Ala Ala Gln Phe Tyr Lys Tyr Asn
385                 390                 395                 400 aaa cct aga caa tgg ctg acg tcg ggc ggg cta ggg gca atg ggt ttc     1248
Lys Pro Arg Gln Trp Leu Thr Ser Gly Gly Leu Gly Ala Met Gly Phe
            405                 410                 415 ggc ctg ccc gct gct atc ggg gcg gcc gtt gca aga cct gat gcg gta     1296
Gly Leu Pro Ala Ala Ile Gly Ala Ala Val Ala Arg Pro Asp Ala Val
        420                 425                 430 gta gtt gac atc gac ggt gac gga agc ttt atg atg aat gtt caa gag     1344
Val Val Asp Ile Asp Gly Asp Gly Ser Phe Met Met Asn Val Gln Glu
    435                 440                 445 tta gcc aca atc cgt gtt gaa aat ctg ccg gtt aag att tta tta ctt     1392
Leu Ala Thr Ile Arg Val Glu Asn Leu Pro Val Lys Ile Leu Leu Leu
450                 455                 460 aac aac cag cat ttg ggt atg gtg gtt cag tgg gag gat cgg ttt tac     1440
Asn Asn Gln His Leu Gly Met Val Val Gln Trp Glu Asp Arg Phe Tyr
465                 470                 475                 480 aag gcg aat cgg gct cat acc tac tta gga aac ccg tca aaa gag tcg     1488
Lys Ala Asn Arg Ala His Thr Tyr Leu Gly Asn Pro Ser Lys Glu Ser
            485                 490                 495 gaa ata ttc cct aac atg gtg aag ttt gct gaa gcc tgt gat atc ccg     1536
Glu Ile Phe Pro Asn Met Val Lys Phe Ala Glu Ala Cys Asp Ile Pro
        500                 505                 510 gct gct cga gtg acc caa aag gcg gat cta cga gca gct att cag aag     1584
Ala Ala Arg Val Thr Gln Lys Ala Asp Leu Arg Ala Ala Ile Gln Lys
    515                 520                 525 atg ttg gat aca ccc ggg cct tac ttg ttg gat gtg att gtg ccg cat     1632
Met Leu Asp Thr Pro Gly Pro Tyr Leu Leu Asp Val Ile Val Pro His
530                 535                 540 caa gaa cac gtg ttg ccc atg atc ccg gct ggc gga ggt ttc tcg gat     1680
Gln Glu His Val Leu Pro Met Ile Pro Ala Gly Gly Gly Phe Ser Asp
545                 550                 555                 560 gtg atc acc gag ggt gat ggc aga acg aaa tat tga                    1716
Val Ile Thr Glu Gly Asp Gly Arg Thr Lys Tyr *
            565                 570

<210> SEQ ID NO 22
<211> LENGTH: 571
<212> TYPE: PRT
<213> ORGANISM: Helianthus annuus

<400> SEQUENCE: 22

Ala Asp Val Leu Val Glu Ala Leu Glu Arg Glu Gly Val Thr Asp Val
1               5                   10                  15

Phe Ala Tyr Pro Gly Gly Ala Ser Met Glu Ile His Gln Ala Leu Thr
            20                  25                  30

Arg Ser Ser Thr Ile Arg Asn Val Leu Pro Arg His Glu Gln Gly Gly
        35                  40                  45

Val Phe Ala Ala Glu Gly Tyr Ala Arg Ala Ser Gly Leu Pro Gly Val
    50                  55                  60

Cys Ile Ala Thr Ser Gly Pro Gly Ala Thr Asn Leu Val Ser Gly Leu
65                  70                  75                  80

Ala Asp Ala Leu Leu Asp Ser Val Pro Met Val Ala Ile Thr Gly Gln
            85                  90                  95

Val Leu Arg Arg Met Ile Gly Thr Asp Ala Phe Gln Glu Thr Pro Ile
        100                 105                 110

Val Glu Val Thr Arg Ser Ile Thr Lys His Asn Tyr Leu Val Leu Asp
    115                 120                 125
```

```
Val Glu Asp Ile Pro Arg Ile Val Arg Glu Ala Phe Tyr Leu Ala Ser
130                 135                 140

Ser Gly Arg Pro Gly Pro Val Leu Ile Asp Val Pro Lys Asp Ile Gln
145                 150                 155                 160

Gln Gln Leu Val Val Pro Lys Trp Asp Glu Pro Met Arg Leu Pro Gly
                165                 170                 175

Tyr Leu Ser Arg Met Pro Lys Pro Gln Tyr Asp Gly His Leu Glu Gln
                180                 185                 190

Ile Val Arg Leu Val Gly Glu Ala Lys Arg Pro Val Leu Tyr Val Gly
                195                 200                 205

Gly Gly Cys Leu Asn Ser Asp Asp Glu Leu Arg Arg Phe Val Glu Leu
210                 215                 220

Thr Gly Ile Pro Val Ala Ser Thr Leu Met Gly Leu Gly Ala Tyr Pro
225                 230                 235                 240

Ala Ser Ser Asp Leu Ser Leu His Met Leu Gly Met His Gly Thr Val
                245                 250                 255

Tyr Ala Asn Tyr Ala Val Asp Lys Ser Asp Leu Leu Leu Ala Phe Gly
                260                 265                 270

Val Arg Phe Asp Asp Arg Val Thr Gly Lys Leu Glu Ala Phe Ala Ser
                275                 280                 285

Arg Ala Lys Ile Val His Ile Asp Ile Asp Pro Ala Glu Ile Gly Lys
                290                 295                 300

Asn Lys Gln Pro His Val Ser Ile Cys Gly Asp Ile Lys Val Ala Leu
305                 310                 315                 320

Gln Gly Leu Asn Lys Ile Leu Glu Glu Lys Asn Ser Val Thr Asn Leu
                325                 330                 335

Asp Phe Ser Thr Trp Arg Lys Glu Leu Asp Glu Gln Lys Met Lys Phe
                340                 345                 350

Pro Leu Ser Phe Lys Thr Phe Gly Glu Ala Ile Pro Pro Gln Tyr Ala
                355                 360                 365

Ile Gln Val Leu Asp Glu Leu Thr Gly Gly Asn Ala Ile Ile Ser Thr
370                 375                 380

Gly Val Gly Gln His Gln Met Trp Ala Ala Gln Phe Tyr Lys Tyr Asn
385                 390                 395                 400

Lys Pro Arg Gln Trp Leu Thr Ser Gly Gly Leu Gly Ala Met Gly Phe
                405                 410                 415

Gly Leu Pro Ala Ala Ile Gly Ala Ala Val Ala Arg Pro Asp Ala Val
                420                 425                 430

Val Val Asp Ile Asp Gly Asp Gly Ser Phe Met Met Asn Val Gln Glu
                435                 440                 445

Leu Ala Thr Ile Arg Val Glu Asn Leu Pro Val Lys Ile Leu Leu Leu
450                 455                 460

Asn Asn Gln His Leu Gly Met Val Val Gln Trp Glu Asp Arg Phe Tyr
465                 470                 475                 480

Lys Ala Asn Arg Ala His Thr Tyr Leu Gly Asn Pro Ser Lys Glu Ser
                485                 490                 495

Glu Ile Phe Pro Asn Met Val Lys Phe Ala Glu Ala Cys Asp Ile Pro
                500                 505                 510

Ala Ala Arg Val Thr Gln Lys Ala Asp Leu Arg Ala Ala Ile Gln Lys
                515                 520                 525

Met Leu Asp Thr Pro Gly Pro Tyr Leu Leu Asp Val Ile Val Pro His
530                 535                 540
```

```
Gln Glu His Val Leu Pro Met Ile Pro Ala Gly Gly Phe Ser Asp
545                 550                 555                 560

Val Ile Thr Glu Gly Asp Gly Arg Thr Lys Tyr
                565                 570

<210> SEQ ID NO 23
<211> LENGTH: 1716
<212> TYPE: DNA
<213> ORGANISM: Helianthus annuus
<220> FEATURE:
<221> NAME/KEY: CDS
<222> LOCATION: (1)...(1716)

<400> SEQUENCE: 23
```

| | | | | | | | | | | | | | | | | |
|---|---|---|---|---|---|---|---|---|---|---|---|---|---|---|---|---|
| gca | gac | gtg | ttg | gtg | gaa | gct | cta | gaa | cgg | gaa | ggt | gtc | acc | gac | gtc | 48 |
| Ala | Asp | Val | Leu | Val | Glu | Ala | Leu | Glu | Arg | Glu | Gly | Val | Thr | Asp | Val | |
| 1 | | | | 5 | | | | | 10 | | | | | 15 | | |
| ttc | gcc | tac | ccc | ggc | ggc | gcg | tca | atg | gag | atc | cac | caa | gct | ctc | acg | 96 |
| Phe | Ala | Tyr | Pro | Gly | Gly | Ala | Ser | Met | Glu | Ile | His | Gln | Ala | Leu | Thr | |
| | | | | 20 | | | | | 25 | | | | | 30 | | |
| cgc | tca | aac | acc | atc | cgc | aat | gtc | ctc | ccc | cgt | cac | gaa | cag | ggc | ggc | 144 |
| Arg | Ser | Asn | Thr | Ile | Arg | Asn | Val | Leu | Pro | Arg | His | Glu | Gln | Gly | Gly | |
| | | | 35 | | | | | 40 | | | | | 45 | | | |
| gtg | ttc | gcc | gca | gaa | ggc | tac | gca | cgc | gcc | tcc | ggt | ctt | ccc | ggc | gtg | 192 |
| Val | Phe | Ala | Ala | Glu | Gly | Tyr | Ala | Arg | Ala | Ser | Gly | Leu | Pro | Gly | Val | |
| | 50 | | | | | 55 | | | | | 60 | | | | | |
| tgt | atc | gcc | act | tcc | ggt | ccc | gga | gct | acg | aac | cta | gtt | agt | ggt | ctt | 240 |
| Cys | Ile | Ala | Thr | Ser | Gly | Pro | Gly | Ala | Thr | Asn | Leu | Val | Ser | Gly | Leu | |
| 65 | | | | | 70 | | | | | 75 | | | | | 80 | |
| gct | gac | gcg | ttg | tta | gac | agt | gtc | ccc | atg | gtg | gca | atc | acc | ggt | caa | 288 |
| Ala | Asp | Ala | Leu | Leu | Asp | Ser | Val | Pro | Met | Val | Ala | Ile | Thr | Gly | Gln | |
| | | | | 85 | | | | | 90 | | | | | 95 | | |
| gtt | ccc | cgg | aga | atg | atc | gga | acc | gat | gtg | ttt | caa | gaa | acc | cca | att | 336 |
| Val | Pro | Arg | Arg | Met | Ile | Gly | Thr | Asp | Val | Phe | Gln | Glu | Thr | Pro | Ile | |
| | | | | 100 | | | | | 105 | | | | | 110 | | |
| gtt | gag | gta | aca | cgt | tcg | att | act | aaa | cat | aat | tat | ctt | gtg | ttg | gat | 384 |
| Val | Glu | Val | Thr | Arg | Ser | Ile | Thr | Lys | His | Asn | Tyr | Leu | Val | Leu | Asp | |
| | | | 115 | | | | | 120 | | | | | 125 | | | |
| gtt | gag | gat | att | ccc | aga | att | gtt | cgt | gag | gct | ttt | tat | ctt | gcg | agt | 432 |
| Val | Glu | Asp | Ile | Pro | Arg | Ile | Val | Arg | Glu | Ala | Phe | Tyr | Leu | Ala | Ser | |
| | 130 | | | | | 135 | | | | | 140 | | | | | |
| tcg | ggt | cga | ccc | ggc | ccg | gtt | ttg | ata | gat | gta | ccg | aaa | gat | ata | cag | 480 |
| Ser | Gly | Arg | Pro | Gly | Pro | Val | Leu | Ile | Asp | Val | Pro | Lys | Asp | Ile | Gln | |
| 145 | | | | | 150 | | | | | 155 | | | | | 160 | |
| caa | cag | tta | gtg | gtg | cca | aaa | tgg | gat | gaa | ccg | atg | agg | tta | ccg | ggt | 528 |
| Gln | Gln | Leu | Val | Val | Pro | Lys | Trp | Asp | Glu | Pro | Met | Arg | Leu | Pro | Gly | |
| | | | | 165 | | | | | 170 | | | | | 175 | | |
| tat | ttg | tct | aga | atg | cca | aag | cct | caa | tat | gat | ggc | cat | ttg | gaa | cag | 576 |
| Tyr | Leu | Ser | Arg | Met | Pro | Lys | Pro | Gln | Tyr | Asp | Gly | His | Leu | Glu | Gln | |
| | | | | 180 | | | | | 185 | | | | | 190 | | |
| att | gtt | agg | ttg | gtg | ggg | gaa | gcg | aaa | agg | ccg | gtt | ttg | tat | gtg | ggt | 624 |
| Ile | Val | Arg | Leu | Val | Gly | Glu | Ala | Lys | Arg | Pro | Val | Leu | Tyr | Val | Gly | |
| | | | 195 | | | | | 200 | | | | | 205 | | | |
| ggt | ggg | tgt | ttg | aat | tcg | gat | gat | gag | ttg | agg | cgg | ttt | gtg | gag | ctt | 672 |
| Gly | Gly | Cys | Leu | Asn | Ser | Asp | Asp | Glu | Leu | Arg | Arg | Phe | Val | Glu | Leu | |
| | 210 | | | | | 215 | | | | | 220 | | | | | |
| acg | ggg | att | ccg | gtt | gca | agt | act | ttg | atg | ggg | ctc | gga | gcg | tac | cct | 720 |
| Thr | Gly | Ile | Pro | Val | Ala | Ser | Thr | Leu | Met | Gly | Leu | Gly | Ala | Tyr | Pro | |
| 225 | | | | | 230 | | | | | 235 | | | | | 240 | |
| gct | tcg | agt | gat | ttg | tcg | ctt | cat | atg | ctt | ggg | atg | cat | ggg | act | gtc | 768 |
| Ala | Ser | Ser | Asp | Leu | Ser | Leu | His | Met | Leu | Gly | Met | His | Gly | Thr | Val | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 245 |     |     |     |     | 250 |     |     |     |     |     | 255 |     |     |      |
| tat | gcg | aat | tat | gcg | gtt | gat | aag | agt | gat | ttg | ttg | ctt | gcg | ttt | ggg | 816  |
| Tyr | Ala | Asn | Tyr | Ala | Val | Asp | Lys | Ser | Asp | Leu | Leu | Leu | Ala | Phe | Gly |      |
|     |     | 260 |     |     |     |     | 265 |     |     |     |     | 270 |     |     |     |      |
| gtg | cgg | ttt | gat | gac | cgt | gtg | acg | ggg | aag | ctt | gag | gcg | ttt | gct | agt | 864  |
| Val | Arg | Phe | Asp | Asp | Arg | Val | Thr | Gly | Lys | Leu | Glu | Ala | Phe | Ala | Ser |      |
|     |     | 275 |     |     |     |     | 280 |     |     |     |     | 285 |     |     |     |      |
| agg | gcg | aag | att | gtt | cat | att | gat | att | gat | ccg | gct | gaa | att | ggg | aag | 912  |
| Arg | Ala | Lys | Ile | Val | His | Ile | Asp | Ile | Asp | Pro | Ala | Glu | Ile | Gly | Lys |      |
|     | 290 |     |     |     |     | 295 |     |     |     |     | 300 |     |     |     |     |      |
| aat | aaa | cag | ccg | cat | gtg | tcg | att | tgt | ggg | gat | att | aag | gtc | gcg | tta | 960  |
| Asn | Lys | Gln | Pro | His | Val | Ser | Ile | Cys | Gly | Asp | Ile | Lys | Val | Ala | Leu |      |
| 305 |     |     |     |     | 310 |     |     |     |     | 315 |     |     |     |     | 320 |      |
| cag | ggt | ttg | aac | aag | att | ttg | gag | gaa | aag | aat | tcg | gtg | act | aat | ctt | 1008 |
| Gln | Gly | Leu | Asn | Lys | Ile | Leu | Glu | Glu | Lys | Asn | Ser | Val | Thr | Asn | Leu |      |
|     |     |     |     | 325 |     |     |     |     | 330 |     |     |     |     | 335 |     |      |
| gat | ttt | tcg | aac | tgg | aga | aag | gaa | ttg | gat | gaa | caa | aaa | gtg | aag | ttt | 1056 |
| Asp | Phe | Ser | Asn | Trp | Arg | Lys | Glu | Leu | Asp | Glu | Gln | Lys | Val | Lys | Phe |      |
|     |     |     | 340 |     |     |     |     | 345 |     |     |     |     | 350 |     |     |      |
| ccg | ttg | agc | ttt | aaa | acg | ttt | ggc | gaa | gcg | att | cct | cca | cag | cat | gct | 1104 |
| Pro | Leu | Ser | Phe | Lys | Thr | Phe | Gly | Glu | Ala | Ile | Pro | Pro | Gln | His | Ala |      |
|     |     | 355 |     |     |     |     | 360 |     |     |     |     | 365 |     |     |     |      |
| att | caa | gtt | ctt | gat | gag | tta | acg | ggc | ggg | aat | gca | att | att | agc | acc | 1152 |
| Ile | Gln | Val | Leu | Asp | Glu | Leu | Thr | Gly | Gly | Asn | Ala | Ile | Ile | Ser | Thr |      |
|     | 370 |     |     |     |     | 375 |     |     |     |     | 380 |     |     |     |     |      |
| ggg | gtc | ggg | caa | cat | cag | atg | tgg | gct | gct | cag | ttt | tac | aaa | tac | aac | 1200 |
| Gly | Val | Gly | Gln | His | Gln | Met | Trp | Ala | Ala | Gln | Phe | Tyr | Lys | Tyr | Asn |      |
| 385 |     |     |     |     | 390 |     |     |     |     | 395 |     |     |     |     | 400 |      |
| aaa | cct | aga | caa | tgg | ctg | acg | tcg | ggc | ggg | cta | ggg | gca | atg | ggt | ttt | 1248 |
| Lys | Pro | Arg | Gln | Trp | Leu | Thr | Ser | Gly | Gly | Leu | Gly | Ala | Met | Gly | Phe |      |
|     |     |     |     | 405 |     |     |     |     | 410 |     |     |     |     | 415 |     |      |
| ggg | ctg | ccc | gct | gct | atc | ggg | gcg | gcc | gtt | gca | aga | cct | gat | gcg | gta | 1296 |
| Gly | Leu | Pro | Ala | Ala | Ile | Gly | Ala | Ala | Val | Ala | Arg | Pro | Asp | Ala | Val |      |
|     |     |     | 420 |     |     |     |     | 425 |     |     |     |     | 430 |     |     |      |
| gta | gtt | gac | atc | gac | ggt | gac | gga | agc | ttt | atg | atg | aat | gtt | caa | gag | 1344 |
| Val | Val | Asp | Ile | Asp | Gly | Asp | Gly | Ser | Phe | Met | Met | Asn | Val | Gln | Glu |      |
|     |     | 435 |     |     |     |     | 440 |     |     |     |     | 445 |     |     |     |      |
| tta | gcc | aca | atc | cgt | gtt | gaa | aat | ctg | ccg | gtt | aag | att | tta | tta | ctt | 1392 |
| Leu | Ala | Thr | Ile | Arg | Val | Glu | Asn | Leu | Pro | Val | Lys | Ile | Leu | Leu | Leu |      |
|     | 450 |     |     |     |     | 455 |     |     |     |     | 460 |     |     |     |     |      |
| aat | aat | cag | cat | ttg | ggt | atg | gtg | gtt | cag | tgg | gag | gat | cgg | ttt | tac | 1440 |
| Asn | Asn | Gln | His | Leu | Gly | Met | Val | Val | Gln | Trp | Glu | Asp | Arg | Phe | Tyr |      |
| 465 |     |     |     |     | 470 |     |     |     |     | 475 |     |     |     |     | 480 |      |
| aag | gcg | aat | agg | gct | cat | acc | tac | tta | gga | aac | ccg | tca | aaa | gag | tcg | 1488 |
| Lys | Ala | Asn | Arg | Ala | His | Thr | Tyr | Leu | Gly | Asn | Pro | Ser | Lys | Glu | Ser |      |
|     |     |     |     | 485 |     |     |     |     | 490 |     |     |     |     | 495 |     |      |
| gaa | ata | ttc | cct | aac | atg | gtg | aag | ttt | gct | gaa | gcc | tgt | gat | atc | ccg | 1536 |
| Glu | Ile | Phe | Pro | Asn | Met | Val | Lys | Phe | Ala | Glu | Ala | Cys | Asp | Ile | Pro |      |
|     |     |     | 500 |     |     |     |     | 505 |     |     |     |     | 510 |     |     |      |
| gct | gct | cga | gtg | acc | caa | aag | gcg | gat | cta | cga | gca | gct | att | cag | aag | 1584 |
| Ala | Ala | Arg | Val | Thr | Gln | Lys | Ala | Asp | Leu | Arg | Ala | Ala | Ile | Gln | Lys |      |
|     |     | 515 |     |     |     |     | 520 |     |     |     |     | 525 |     |     |     |      |
| atg | ttg | gat | aca | ccc | ggg | cct | tac | ttg | ttg | gat | gtg | att | gtg | ccg | cat | 1632 |
| Met | Leu | Asp | Thr | Pro | Gly | Pro | Tyr | Leu | Leu | Asp | Val | Ile | Val | Pro | His |      |
|     | 530 |     |     |     |     | 535 |     |     |     |     | 540 |     |     |     |     |      |
| caa | gaa | cac | gtg | ttg | ccc | atg | atc | ccg | gct | ggc | gga | ggt | ttc | tcg | gat | 1680 |
| Gln | Glu | His | Val | Leu | Pro | Met | Ile | Pro | Ala | Gly | Gly | Gly | Phe | Ser | Asp |      |
| 545 |     |     |     |     | 550 |     |     |     |     | 555 |     |     |     |     | 560 |      |
| gtg | atc | acc | gag | ggt | gat | ggc | aga | acg | aaa | tat | tga |     |     |     |     | 1716 |
| Val | Ile | Thr | Glu | Gly | Asp | Gly | Arg | Thr | Lys | Tyr |     |     |     |     |     |      |

```
Val Ile Thr Glu Gly Asp Gly Arg Thr Lys Tyr  *
                565                 570

<210> SEQ ID NO 24
<211> LENGTH: 571
<212> TYPE: PRT
<213> ORGANISM: Helianthus annuus

<400> SEQUENCE: 24

Ala Asp Val Leu Val Glu Ala Leu Glu Arg Glu Gly Val Thr Asp Val
  1               5                  10                  15

Phe Ala Tyr Pro Gly Gly Ala Ser Met Glu Ile His Gln Ala Leu Thr
             20                  25                  30

Arg Ser Asn Thr Ile Arg Asn Val Leu Pro Arg His Glu Gln Gly Gly
         35                  40                  45

Val Phe Ala Ala Glu Gly Tyr Ala Arg Ala Ser Gly Leu Pro Gly Val
     50                  55                  60

Cys Ile Ala Thr Ser Gly Pro Gly Ala Thr Asn Leu Val Ser Gly Leu
 65                  70                  75                  80

Ala Asp Ala Leu Leu Asp Ser Val Pro Met Val Ala Ile Thr Gly Gln
                 85                  90                  95

Val Pro Arg Arg Met Ile Gly Thr Asp Val Phe Gln Glu Thr Pro Ile
            100                 105                 110

Val Glu Val Thr Arg Ser Ile Thr Lys His Asn Tyr Leu Val Leu Asp
        115                 120                 125

Val Glu Asp Ile Pro Arg Ile Val Arg Glu Ala Phe Tyr Leu Ala Ser
    130                 135                 140

Ser Gly Arg Pro Gly Pro Val Leu Ile Asp Val Pro Lys Asp Ile Gln
145                 150                 155                 160

Gln Gln Leu Val Val Pro Lys Trp Asp Glu Pro Met Arg Leu Pro Gly
                165                 170                 175

Tyr Leu Ser Arg Met Pro Lys Pro Gln Tyr Asp Gly His Leu Glu Gln
            180                 185                 190

Ile Val Arg Leu Val Gly Glu Ala Lys Arg Pro Val Leu Tyr Val Gly
        195                 200                 205

Gly Gly Cys Leu Asn Ser Asp Asp Glu Leu Arg Arg Phe Val Glu Leu
    210                 215                 220

Thr Gly Ile Pro Val Ala Ser Thr Leu Met Gly Leu Gly Ala Tyr Pro
225                 230                 235                 240

Ala Ser Ser Asp Leu Ser Leu His Met Leu Gly Met His Gly Thr Val
                245                 250                 255

Tyr Ala Asn Tyr Ala Val Asp Lys Ser Asp Leu Leu Leu Ala Phe Gly
            260                 265                 270

Val Arg Phe Asp Asp Arg Val Thr Gly Lys Leu Glu Ala Phe Ala Ser
        275                 280                 285

Arg Ala Lys Ile Val His Ile Asp Ile Asp Pro Ala Glu Ile Gly Lys
    290                 295                 300

Asn Lys Gln Pro His Val Ser Ile Cys Gly Asp Ile Lys Val Ala Leu
305                 310                 315                 320

Gln Gly Leu Asn Lys Ile Leu Glu Glu Lys Asn Ser Val Thr Asn Leu
                325                 330                 335

Asp Phe Ser Asn Trp Arg Lys Glu Leu Asp Glu Gln Lys Val Lys Phe
            340                 345                 350

Pro Leu Ser Phe Lys Thr Phe Gly Glu Ala Ile Pro Pro Gln His Ala
        355                 360                 365
```

-continued

```
Ile Gln Val Leu Asp Glu Leu Thr Gly Gly Asn Ala Ile Ile Ser Thr
        370                 375                 380

Gly Val Gly Gln His Gln Met Trp Ala Ala Gln Phe Tyr Lys Tyr Asn
385                 390                 395                 400

Lys Pro Arg Gln Trp Leu Thr Ser Gly Gly Leu Gly Ala Met Gly Phe
                405                 410                 415

Gly Leu Pro Ala Ala Ile Gly Ala Ala Val Ala Arg Pro Asp Ala Val
                420                 425                 430

Val Val Asp Ile Asp Gly Asp Gly Ser Phe Met Met Asn Val Gln Glu
            435                 440                 445

Leu Ala Thr Ile Arg Val Glu Asn Leu Pro Val Lys Ile Leu Leu Leu
        450                 455                 460

Asn Asn Gln His Leu Gly Met Val Val Gln Trp Glu Asp Arg Phe Tyr
465                 470                 475                 480

Lys Ala Asn Arg Ala His Thr Tyr Leu Gly Asn Pro Ser Lys Glu Ser
                485                 490                 495

Glu Ile Phe Pro Asn Met Val Lys Phe Ala Glu Ala Cys Asp Ile Pro
                500                 505                 510

Ala Ala Arg Val Thr Gln Lys Ala Asp Leu Arg Ala Ala Ile Gln Lys
            515                 520                 525

Met Leu Asp Thr Pro Gly Pro Tyr Leu Leu Asp Val Ile Val Pro His
        530                 535                 540

Gln Glu His Val Leu Pro Met Ile Pro Ala Gly Gly Phe Ser Asp
545                 550                 555                 560

Val Ile Thr Glu Gly Asp Gly Arg Thr Lys Tyr
                565                 570
```